(12) United States Patent
Joh et al.

(10) Patent No.: US 12,295,605 B2
(45) Date of Patent: May 13, 2025

(54) SURGICAL INSTRUMENT

(71) Applicant: LIVSMED INC., Seongnam-si (KR)

(72) Inventors: Joonhee Joh, Seongnam-si (KR); Jung Joo Lee, Seongnam-si (KR); Heejin Kim, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 18/757,158

(22) Filed: Jun. 27, 2024

(65) Prior Publication Data
US 2024/0341795 A1 Oct. 17, 2024

Related U.S. Application Data

(63) Continuation of application No. PCT/KR2022/021611, filed on Dec. 29, 2022.

(30) Foreign Application Priority Data

Dec. 29, 2021 (KR) .................. 10-2021-0191638

(51) Int. Cl.
*A61B 17/29* (2006.01)
*A61B 17/00* (2006.01)

(52) U.S. Cl.
CPC .............................. *A61B 17/2909* (2013.01); *A61B 2017/00477* (2013.01); *A61B 2017/00862* (2013.01); *A61B 2017/2912* (2013.01); *A61B 2017/292* (2013.01); *A61B 2017/2925* (2013.01); *A61B 2017/2929* (2013.01); *A61B 2017/294* (2013.01)

(58) Field of Classification Search
CPC ...... A61B 17/2909; A61B 2017/00477; A61B 2017/00862; A61B 2017/2912; A61B 2017/292; A61B 2017/2925; A61B 2017/2929; A61B 2017/294
See application file for complete search history.

(56) References Cited

U.S. PATENT DOCUMENTS 9,737,298 B2 8/2017 Lewis, Jr. et al.
2022/0039817 A1* 2/2022 Lee ..................... A61B 17/295

FOREIGN PATENT DOCUMENTS

| CN | 113598897 A | 11/2021 |
|---|---|---|
| JP | 2005-502398 A | 1/2005 |
| KR | 10-2018-0073608 A | 7/2018 |
| KR | 10-2118721 B1 | 6/2020 |

* cited by examiner

*Primary Examiner* — Brooke Labranche
(74) *Attorney, Agent, or Firm* — Bridgeway IP Law Group, PLLC; Sang Ho Lee; Hyun Woo Shin

(57) ABSTRACT

The present invention relates to a surgical instrument, and, specifically, to a surgical instrument which can be manually or automatically operated in order to be used in a laparoscopic surgery or various surgeries, and which comprises a lock device capable of locking or unlocking for at least one motion.

14 Claims, 28 Drawing Sheets

SURGICAL INSTRUMENT

CROSS-REFERENCE TO RELATED APPLICATION

This application is a continuation application of International Application No. PCT/KR2022/021611, filed on Dec. 29, 2022, and claims priority to Korean Application No. 10-2021-0191638, filed on Dec. 29, 2021 in the Korean Intellectual Property Office, the entire disclosures of which are incorporated herein by reference.

TECHNICAL FIELD

The present disclosure relates to a surgical instrument, and more particularly, to a surgical instrument that is operable manually or automatically to be used in laparoscopic surgery or other various surgeries, and includes a locking device that may lock and/or unlock at least one motion.

BACKGROUND ART

In medical terms, a surgery refers to curing an illness by incising, opening, or manipulating the skin, mucous membranes, or other tissues using medical instruments. In particular, an open surgery and the like, which incise and open a skin at a surgical site to treat, remodel, or remove organs in the surgical site, cause problems such as bleeding, side effects, patient's pain, scar, etc. Therefore, recently, a surgery performed by forming predetermined holes in a skin and inserting only a medical instrument, such as a laparoscope, surgical instrument, or microsurgical microscope, into the holes or a surgery using a robot, now come into the spotlight as an alternative.

A surgical instrument is a tool that a doctor uses to operate a surgical site by manipulating an end tool disposed on one end of a shaft, which passes through a hole drilled in a skin, either by a hand through a predetermined manipulation part or by using a robotic arm. The end tool disposed at the surgical instrument is manipulated to perform motions, such as rotation, gripping, cutting, etc. through a predetermined structure.

However, there is a need for the surgical instrument to be maintained in a specific posture, that is, in a locked state while a surgery is performed using the surgical instrument, even if a user does not apply force to the surgical instrument. For example, in a state where a patient's tissue is gripped with a first surgical instrument, if a doctor wants to suture the gripped patient's tissue by using a second surgical instrument, there is a need for the first surgical instrument to be locked in the state of gripping the patient's tissue.

The aforementioned background technology is technical information possessed by the inventor for derivation of the present disclosure or acquired by the inventor during the derivation of the present disclosure, and is not necessarily prior art disclosed to the public before the application of the present disclosure.

DESCRIPTION OF EMBODIMENTS

Technical Problem

The present disclosure is directed to providing a surgical instrument, which is operable manually or automatically to be used in laparoscopic surgery or other various surgeries, and includes a locking device that may lock and/or unlock at least one motion.

Solution to Problem

According to an aspect of the present disclosure, there is provided a surgical instrument that includes an end tool having one or more jaws and rotatable in two or more directions, a manipulation part to control rotation of the end tool in the two or more directions, a power transmission part including one or more jaw wires connected to the manipulation part to transmit rotation of the manipulation part to the jaws, and a connection part extending in a first direction (X-axis), and having one end portion coupled to the end tool and another end coupled to the manipulation part, such that the manipulation part and the end tool are connected to each other, wherein the manipulation part includes a pitch manipulation part to control a pitch motion of the end tool, and a locking member formed to be coupled to the pitch manipulation part, to lock or unlock a pitch motion of the pitch manipulation part according to whether or not the locking member is coupled to the pitch manipulation part.

In the present disclosure, the locking member may include a locking body part fixedly coupled to the pitch manipulation part, and a locking part formed to be coupled to the locking body part.

In the present disclosure, the locking part may be coupled to the locking body part when the locking part is located at a first position, to restrict movement of the locking body part, and the locking part may be spaced apart from the locking body part to a certain extent when the locking part is located at a second position, to allow rotation of the locking body part.

In the present disclosure, the locking body part may be formed in a gear shape including a plurality of first coupling parts, and the locking part may be formed in a hook shape to be coupled to the first coupling part.

In the present disclosure, the surgical instrument may further include a locking control part that controls a position of the locking part so that the locking part is located at any one of the first position or the second position.

In the present disclosure, the locking control part may be configured to perform a linear reciprocating motion with respect to the locking body part, and the locking control part may press the locking part while moving in one direction, such that the locking part moves in a direction of being spaced away from the locking body part.

In the present disclosure, a width of the locking control part may increase along the one direction.

In the present disclosure, the locking control part may press the locking part in such a direction that the locking part is away from the locking body part while moving in the one direction.

In the present disclosure, a first elastic member may be interposed between the locking control part and the locking body part to apply a predetermined elastic force to the locking control part so that the locking part is located at either the first position or the second position.

In the present disclosure, the pitch manipulation part may be axially coupled to the connection part, and the locking member may control whether the pitch manipulation part rotates with respect to the connection part.

According to another embodiment of the present disclosure, there is provided a surgical instrument that includes an end tool having one or more jaws and rotatable in two or more directions, a manipulation part to control rotation of the end tool in the two or more directions, a power transmission part including one or more jaw wires connected to the manipulation part to transmit rotation of the manipulation part to the jaws, and a connection part extending in a first direction (X-axis), and having one end portion coupled to the end tool and another end coupled to the manipulation part, such that the manipulation part and the end tool are connected to each other, wherein the manipulation part includes a yaw manipulation part to control a yaw motion of the end tool, and a locking member formed to be coupled to the yaw manipulation part, to lock or unlock a yaw motion of the yaw manipulation part according to whether or not the locking member is coupled to the pitch manipulation part.

In the present disclosure, the locking member may include a locking body part fixedly coupled to the yaw manipulation part, and a locking part formed to be coupled to the locking body part.

In the present disclosure, the locking part may be coupled to the locking body part when the locking part is located at a first position, to restrict movement of the locking body part, and the locking part may be spaced apart from the locking body part to a certain extent when the locking part is located at a second position, to allow rotation of the locking body part.

In the present disclosure, the locking body part may be formed in a gear shape including a plurality of first coupling parts, and the locking part may be formed in a hook shape to be coupled to the first coupling part.

In the present disclosure, the surgical instrument may further include a locking control part that controls a position of the locking part so that the locking part is located at any one of the first position or the second position.

In the present disclosure, the locking control part may be configured to perform a linear reciprocating motion with respect to the locking body part, and the locking control part may press the locking part while moving in one direction, such that the locking part moves away from the locking body part.

In the present disclosure, a width of the locking control part may increase along the one direction.

In the present disclosure, the locking control part may press the locking part in such a direction that the locking part is away from the locking body part while moving in the one direction.

In the present disclosure, a first elastic member may be interposed between the locking control part and the locking body part to apply a predetermined elastic force to the locking control part so that the locking part is located at either the first position or the second position.

In the present disclosure, the yaw manipulation part may be axially coupled to the connection part, and the locking member may control whether the yaw manipulation part rotates with respect to the connection part.

Other aspects, features, and advantages in addition to those described above will become apparent from the following drawings, claims, and detailed description of the invention.

Advantageous Effects of Disclosure

According to the present disclosure, at least one motion can be locked and/or unlocked, so that convenience of a surgical operator can be improved, and accuracy, reliability, and speed of surgery can be improved.

MODE OF DISCLOSURE

Figure 1:
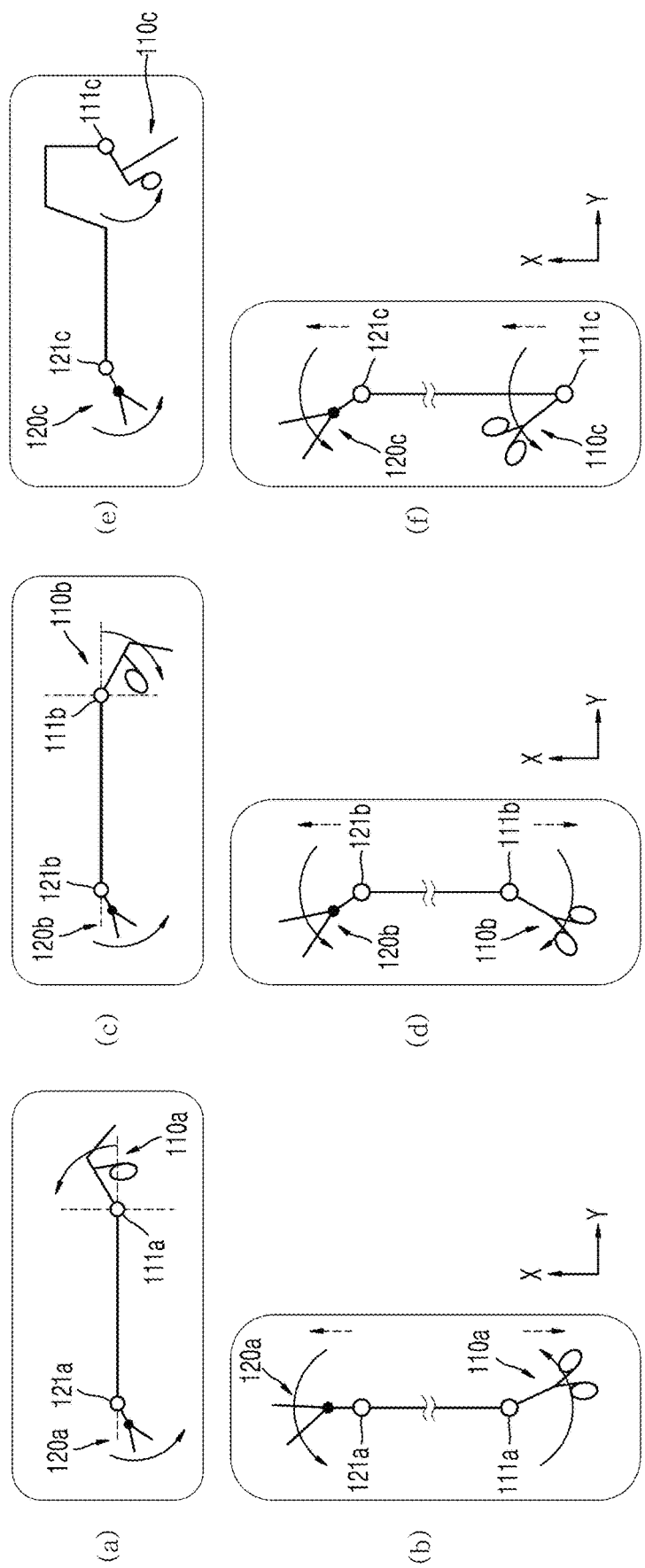
FIG. 1 illustrates: (a) a conceptual diagram of a pitch motion of the related art surgical instrument and (b) a conceptual diagram of a yaw motion thereof; (c) a conceptual diagram of a pitch motion of another related art surgical instrument and (d) a conceptual diagram of a yaw motion thereof; and (e) a conceptual diagram of a pitch motion of a surgical instrument according to the present disclosure, and (f) a conceptual diagram of a yaw motion thereof.

While the present disclosure is susceptible to various modifications and alternative forms, specific embodiments thereof are shown by way of example in the drawings and will herein be described in detail. However, it should be understood that there is no intent to limit the present disclosure to the particular forms disclosed herein, rather, the present disclosure should be construed to cover various modifications, equivalents, and alternatives of embodiments of the present disclosure. In describing the present disclosure, detailed description of known related arts will be omitted when it is determined that the gist of the present disclosure may be unnecessarily obscured.

Although terms such as "first," "second," and the like may be used to describe various components, such components should not be limited to the above terms The terms are only used to distinguish one component from another.

The terms used herein are for the purpose of describing particular embodiments only and are not intended to be limiting to the present disclosure. Singular forms are intended to include plural forms as well, unless the context clearly indicates otherwise. In the present application, it will be further understood that the terms "comprise," "comprising," "include," and/or "including", when used in this specification, specify the presence of stated features, integers, steps, operations, elements, components and/or groups thereof but do not preclude the presence or addition of one or more other features, integers, steps, operations, elements, components and/or groups thereof.

Hereinafter, the embodiments of the present disclosure will be described below in detail with reference to the accompanying drawings, and when the embodiments of the present disclosure are described with reference to the drawings, the same or corresponding components are given the same reference numerals, and repetitive descriptions thereof will be omitted.

Further, in describing the various embodiments of the present disclosure, it is to be understood that each embodiment is not intended to be interpreted or implemented independently, and that the technical ideas described in each embodiment may be interpreted or implemented in combination with other embodiments described separately.

In a surgical instrument according to the present disclosure, when a manipulation part is rotated in one direction for at least any one of pitch, yaw, and actuation motions, an end tool is rotated in intuitively the same direction as a direction in which the manipulation part is moved.

FIG. 1(a) is a conceptual diagram of a pitch motion of a conventional surgical instrument, and FIG. 1(b) is a conceptual diagram of a yaw motion thereof.

Referring to FIG. 1(a), in performing a pitch motion of a conventional surgical instrument, in a state in which an end tool 120a is formed in front of a rotation center 121a of the end tool, and a manipulation part 110a is formed at the rear of a rotation center 111a of the manipulation part, when the manipulation part 110a is rotated in a clockwise direction, the end tool 120a is also rotated in the clockwise direction, and when the manipulation part 120a is rotated in a counterclockwise direction, the end tool 120a is also rotated in the counterclockwise direction. Referring to FIG. 1(b), in performing a yaw motion of the conventional surgical instrument, in a state in which the end tool 120a is formed in front of the rotation center 121a of the end tool, and the manipulation part 110a is formed at the rear of the rotation center 111a of the manipulation part, when the manipulation part 110a is rotated in the clockwise direction, the end tool 120a is also rotated in the clockwise direction, and when the manipulation part 120a is rotated in the counterclockwise direction, the end tool 120a is also rotated in the counterclockwise direction. In this case, in view of left and right directions of a user, when the user moves the manipulation part 110a to the left, the end tool 120a is moved to the right, and when the user moves the manipulation part 110a to the right, the end tool 120a is moved to the left. As a result, a manipulation direction of the user and an operation direction of the end tool are opposite to each other, which may cause the user to make a mistake, and user's manipulation may not be easy.

FIG. 1(c) is a conceptual diagram of a pitch motion of another conventional surgical instrument, and FIG. 1(d) is a conceptual diagram of a yaw motion thereof.

Referring to FIG. 1(c), in the conventional surgical instrument, which is partially formed in a mirror symmetrical shape, in performing a pitch motion, in a state in which an end tool 120b is formed in front of a rotation center 121b of the end tool, and a manipulation part 110b is formed at the rear of a rotation center 111b of the manipulation part, when the manipulation part 110b is rotated in the clockwise direction, the end tool 120b is rotated in the counterclockwise direction, and when the manipulation part 110b is rotated in the counterclockwise direction, the end tool 120b is rotated in the clockwise direction. In this case, in view of rotation directions of the manipulation part and the end tool, a rotation direction in which the user rotates the manipulation part 110b and a rotation direction of the end tool 120b according thereto are opposite to each other. As a result, the user may be confused with the manipulation direction, and as the operation of a joint is not intuitive, the user may make an error. Further, referring to FIG. 1(d), in performing a yaw motion, in a state in which the end tool 120b is formed in front of the rotation center 121b of the end tool, and the manipulation part 110b is formed at the rear of the rotation center 111b of the manipulation part, when the manipulation part 110b is rotated in the clockwise direction, the end tool 120b is rotated in the counterclockwise direction, and when the manipulation part 110b is rotated in the counterclockwise direction, the end tool 120b is rotated in the clockwise direction. In this case, in view of rotation directions of the manipulation part and the end tool, a rotation direction in which the user rotates the manipulation part 110b and a rotation direction of the end tool 120b according thereto are opposite to each other. As a result, the user may be confused with the manipulation direction, and as the operation of the joint is not intuitive, the user may make an error. In the user's pitch or yaw manipulation of the conventional surgical instrument, the user's manipulation direction and the end tool's operation direction do not match each other in view of one of the rotation direction and the left and right directions. This is because the configurations of the end tool and the manipulation part are different from each other in the joint configuration of the conventional surgical instrument. That is, this is because the manipulation part is formed at the rear of the rotation center of the manipulation part, while the end tool is formed in front of the rotation center of the end tool. In order to address the above problems, in a surgical instrument according to an embodiment of the present disclosure, which is illustrated in FIGS. 1(e) and 1(f), an end tool 120c is formed in front of a rotation center 121c of the end tool and a manipulation part 110c is also formed in front of a rotation center 111c of the manipulation part, so that the operations of the manipulation part 110c and the end tool 120c are intuitively matched with each other. In other words, unlike existing examples such as those shown in FIGS. 1(a), 1(b), 1(c), and 1(d), in which the manipulation part is close to a user with respect to the joint thereof (that is, away from the end tool), the surgical instrument according to an embodiment of the present disclosure, which is illustrated in FIGS. 1(e) and 1(f), is formed such that at least a portion of the manipulation part is closer (than a joint thereof) to the end tool with respect to the joint thereof at any one moment or more in a manipulation process.

In other words, in the conventional surgical instrument as illustrated in FIGS. 1(a), 1(b), 1(c), and 1(d), the manipulation part is formed at the rear of the rotation center thereof, while the end tool is located in front of the rotation center thereof, and thus the end tool is moved at a front side thereof with a rear side fixed through a motion of the manipulation part that is moved at a rear side thereof with a front side thereof fixed, which is not an intuitively matching structure. Accordingly, a mismatch may occur between the manipulation of the manipulation part and the motion of the end tool in view of the left and right directions or in view of the rotation direction, which may cause confusion to the user, and the manipulation of the manipulation part may be difficult to perform intuitively and quickly and may cause mistakes. In contrast, in the surgical instrument according to an embodiment of the present disclosure, since both the end tool and the manipulation part are moved with respect to the rotation center formed at the rear side thereof, it may be said that the motions are intuitively matched with each other in terms of structure. In other words, moving portions of the manipulation part are moved with respect to the rotation center formed at the rear side thereof just as moving portions of the end tool are moved with respect to the rotation center formed at the rear side thereof, and thus it may be said that the motions are intuitively matched with each other in terms of structure. This allows the user to intuitively and quickly perform a control in a direction toward the end tool, and a possibility of making a mistake may be significantly reduced. Hereinafter, a detailed mechanism enabling the above-described function will be described below.

<Surgical Instrument>

Figure 2:
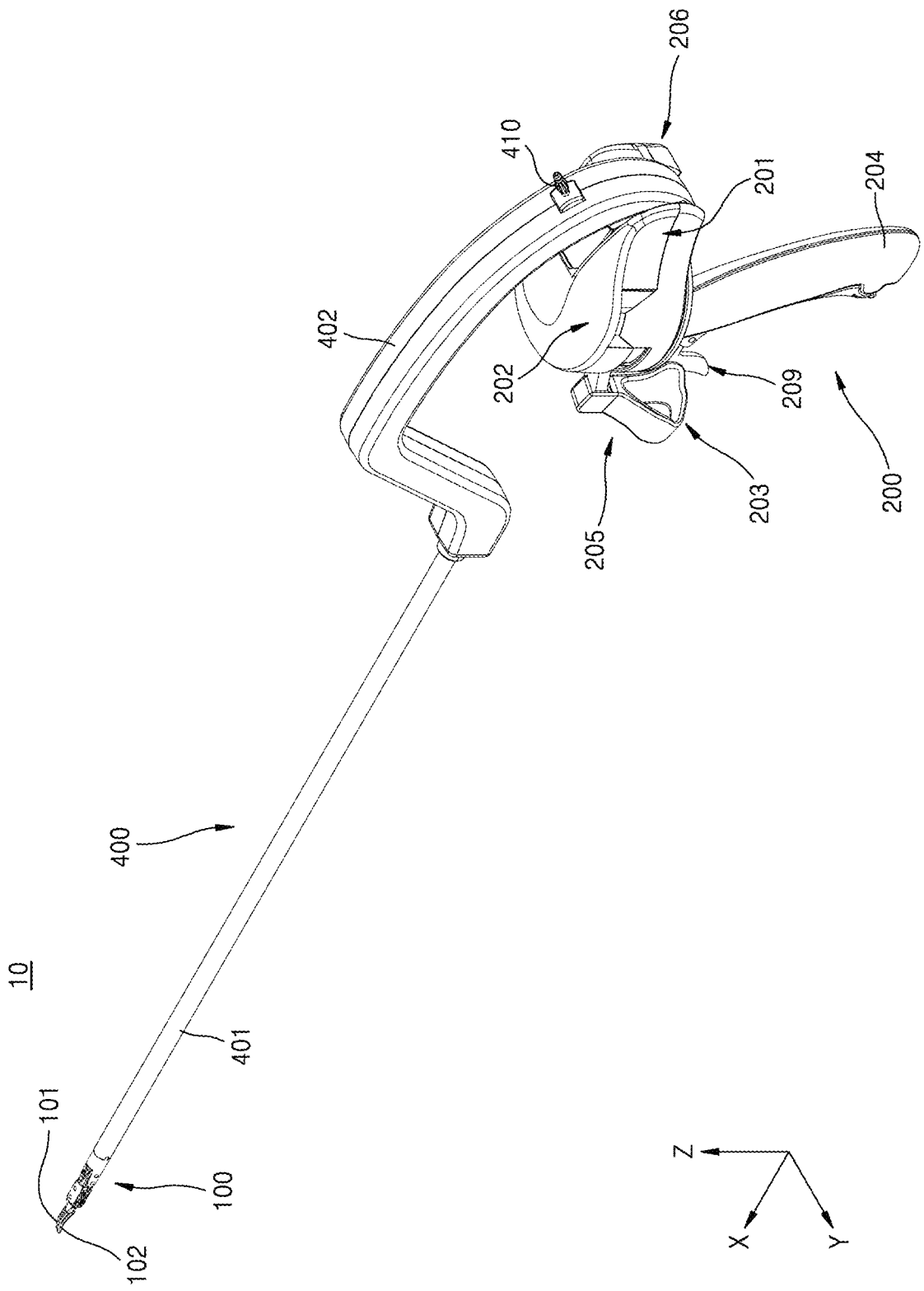
FIG. 2 is a perspective view illustrating a surgical instrument according to a first embodiment of the present disclosure.
Figure 3:
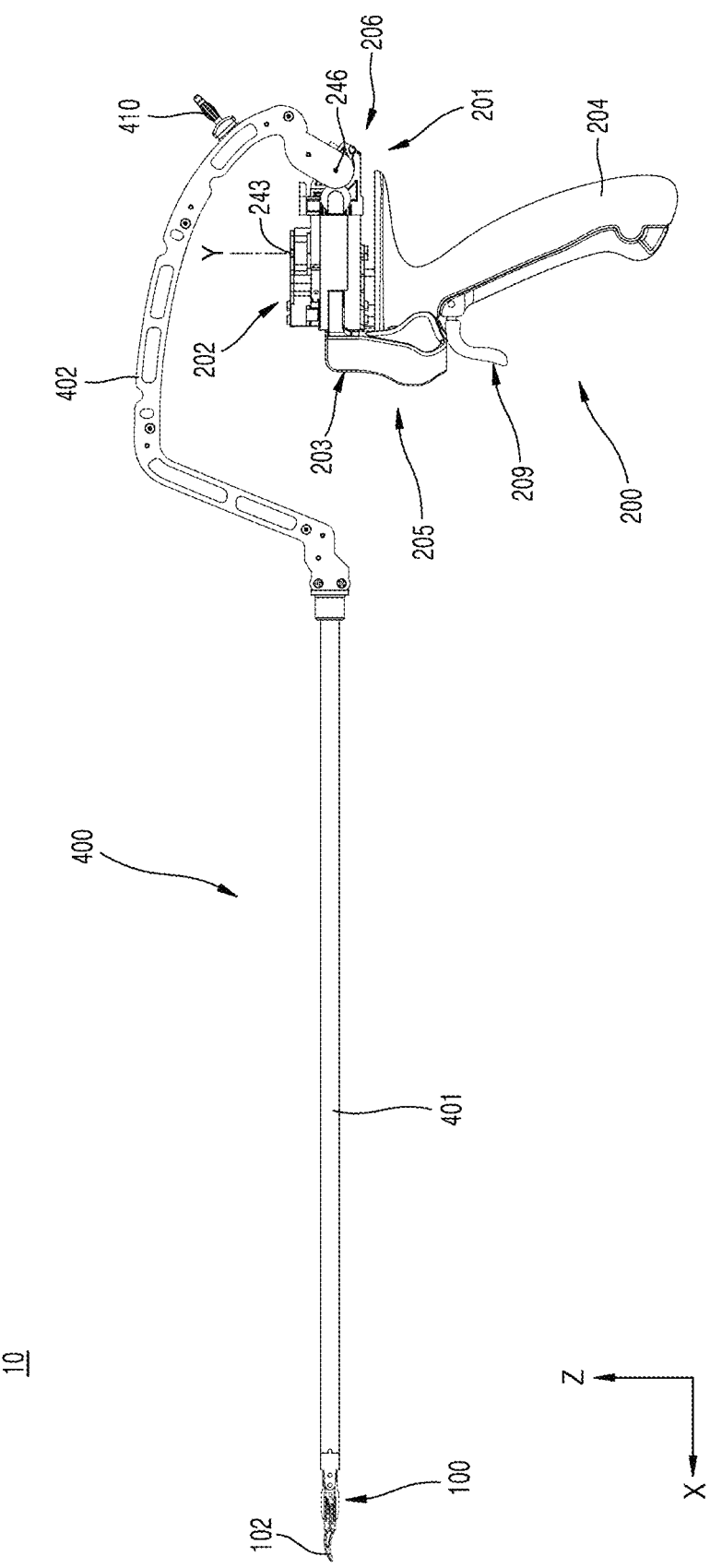
FIG. 3 is a side view of the surgical instrument of FIG. 2.
Figure 4:
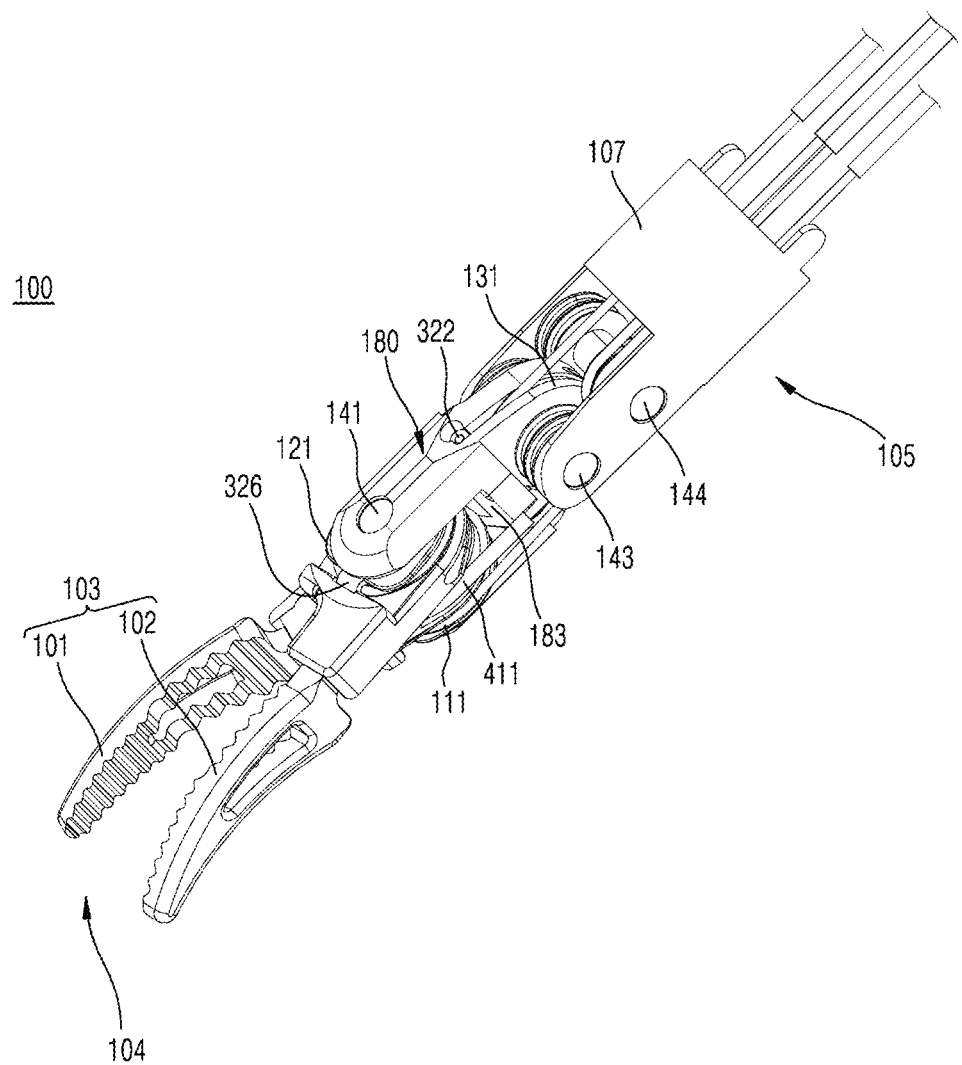
FIGS. 4 and 5 are perspective views illustrating an end tool of the surgical instrument of FIG. 2.
Figure 5:
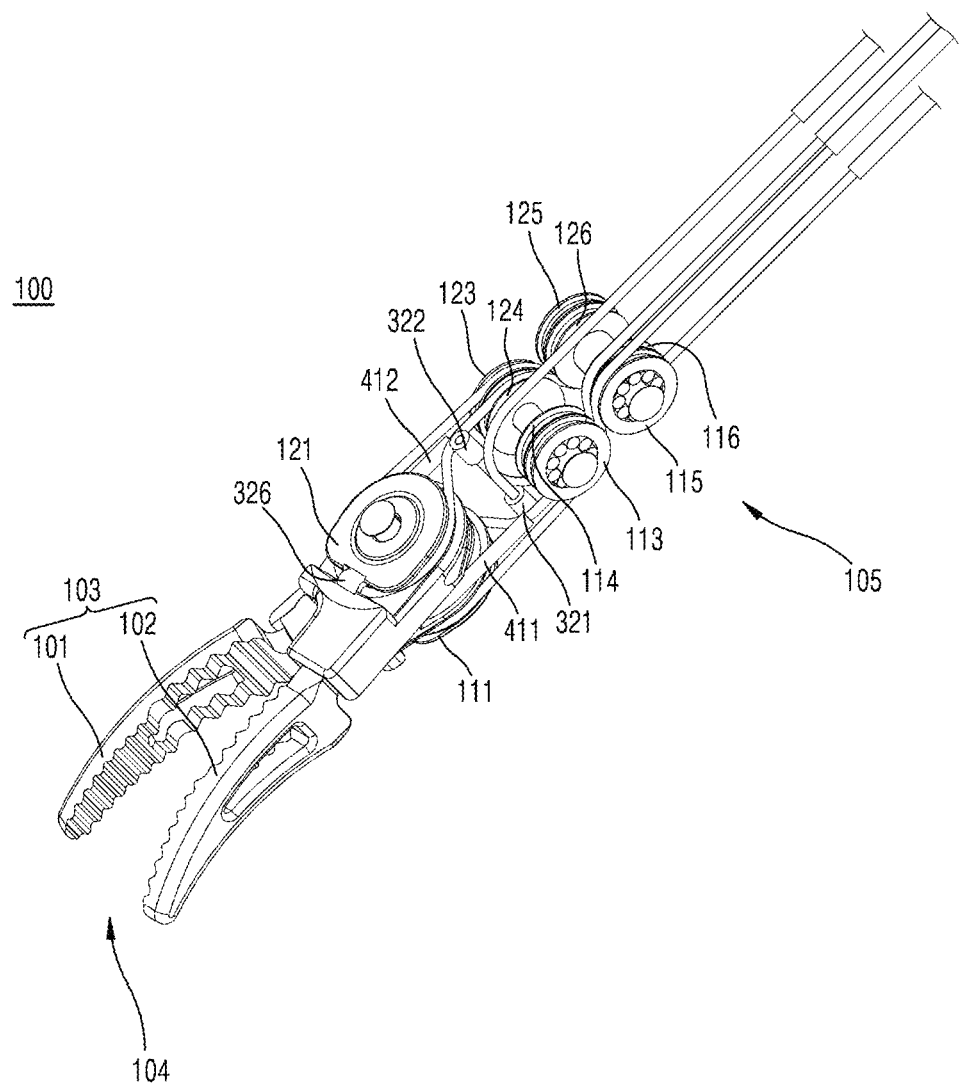
Figure 6:
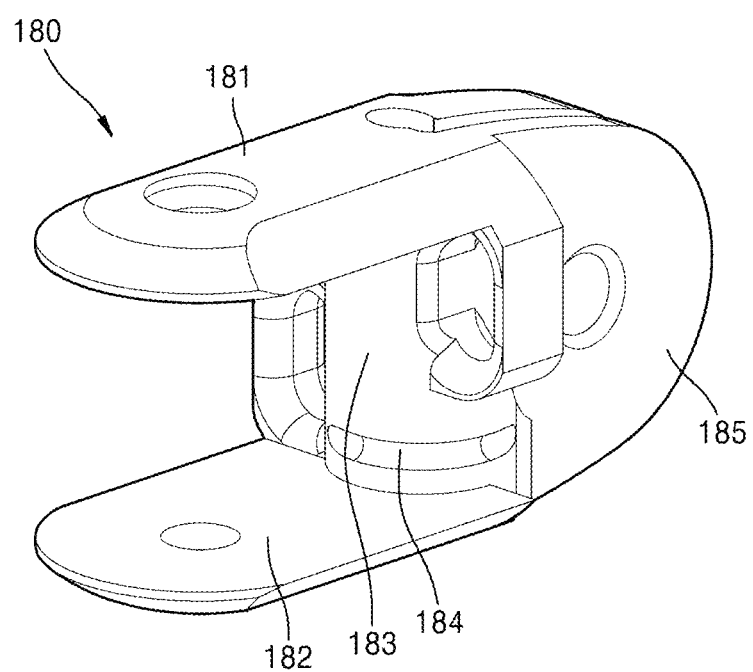
FIG. 6 is an enlarged perspective view illustrating the end tool hub of the surgical instrument of FIG. 4.
Figure 7:
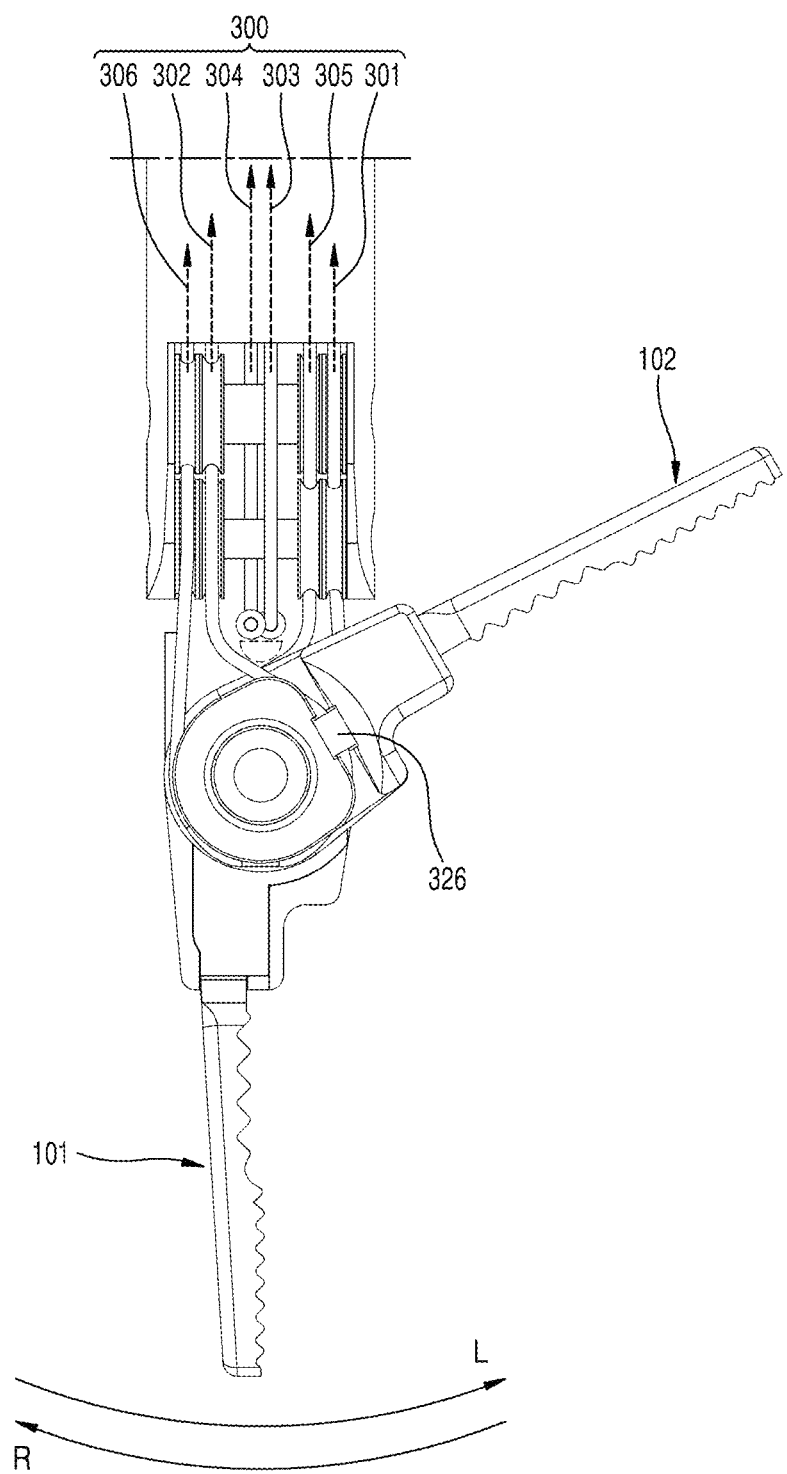
FIGS. 7 and 8 are plan views illustrating the end tool of the surgical instrument of FIG. 2.
Figure 8:
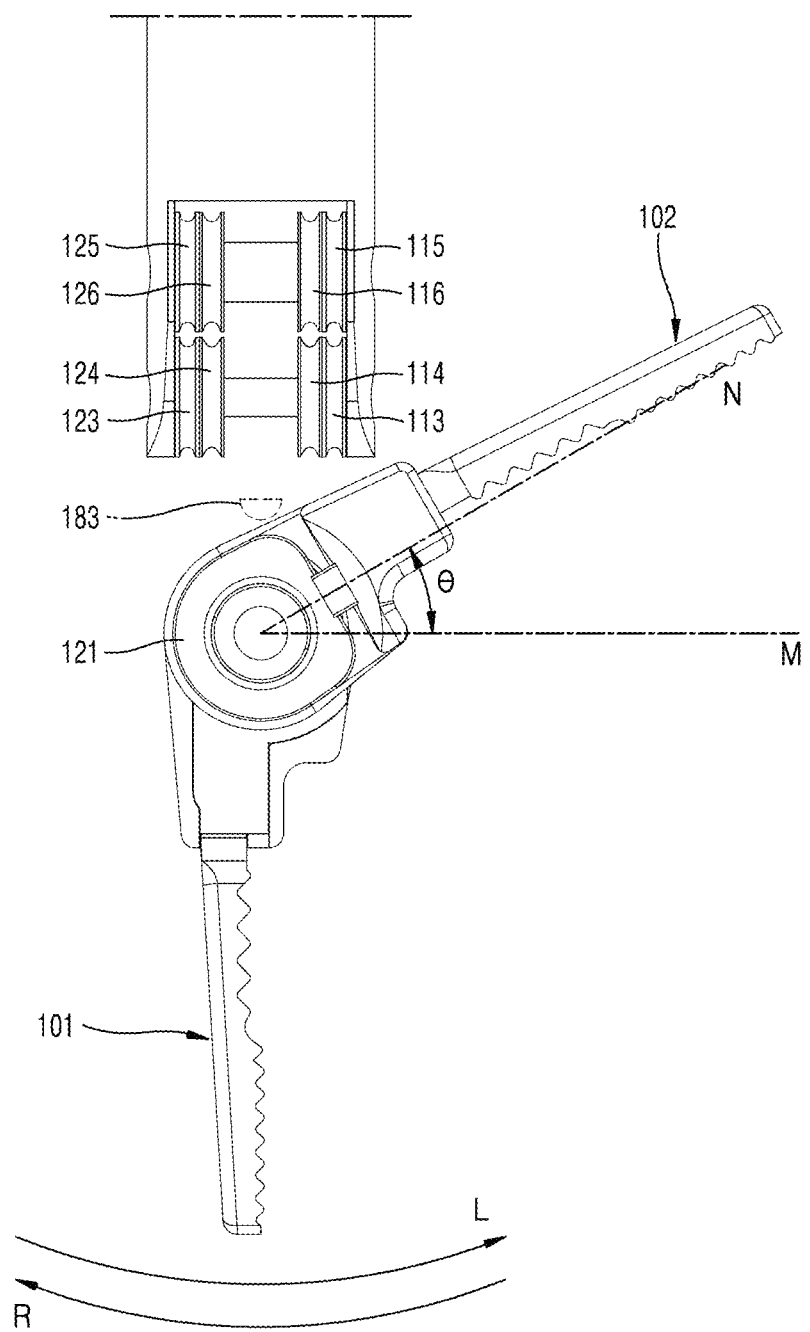
Figure 9:
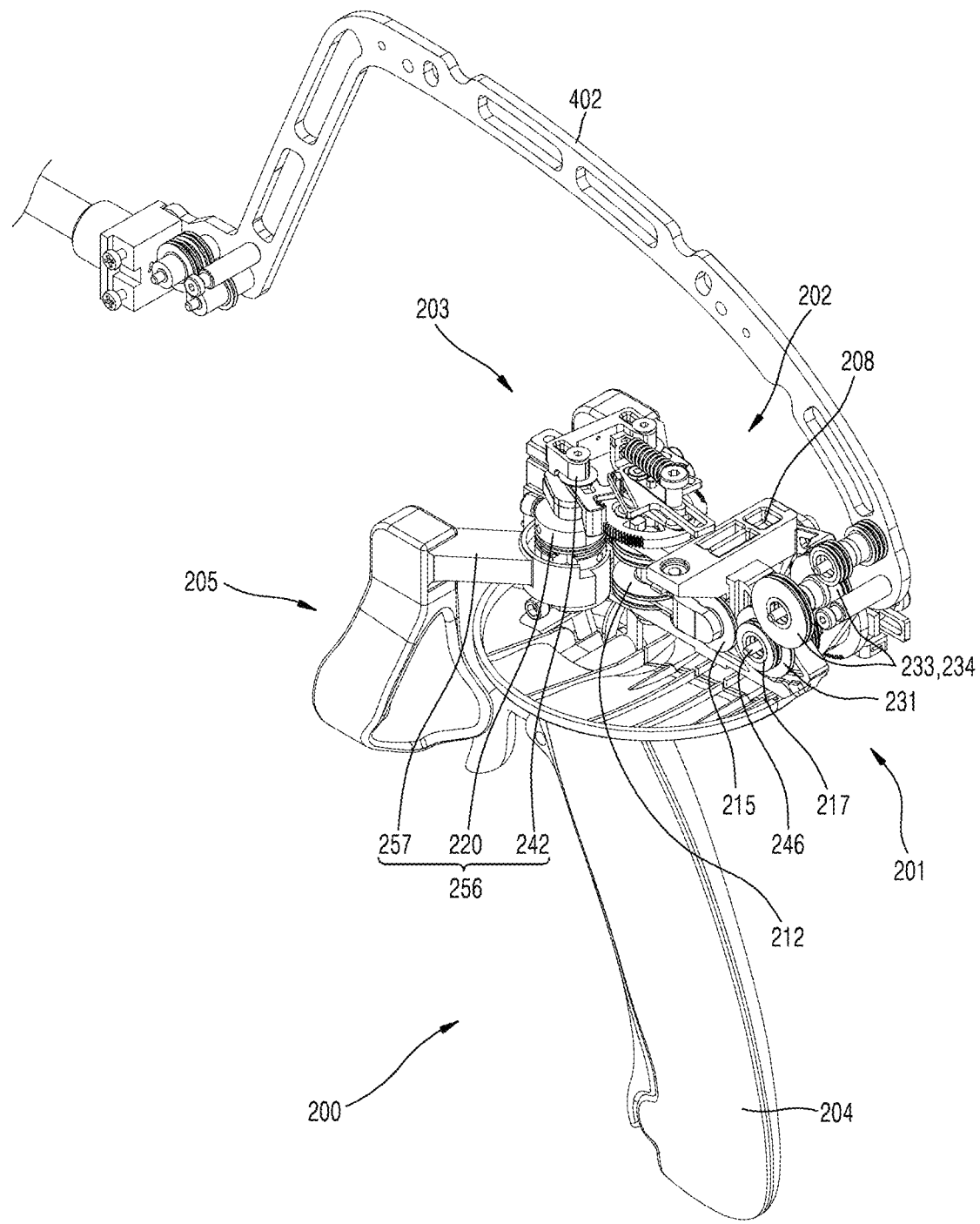
FIGS. 9 and 10 are perspective views illustrating a manipulation part of the surgical instrument of FIG. 2.
Figure 10:
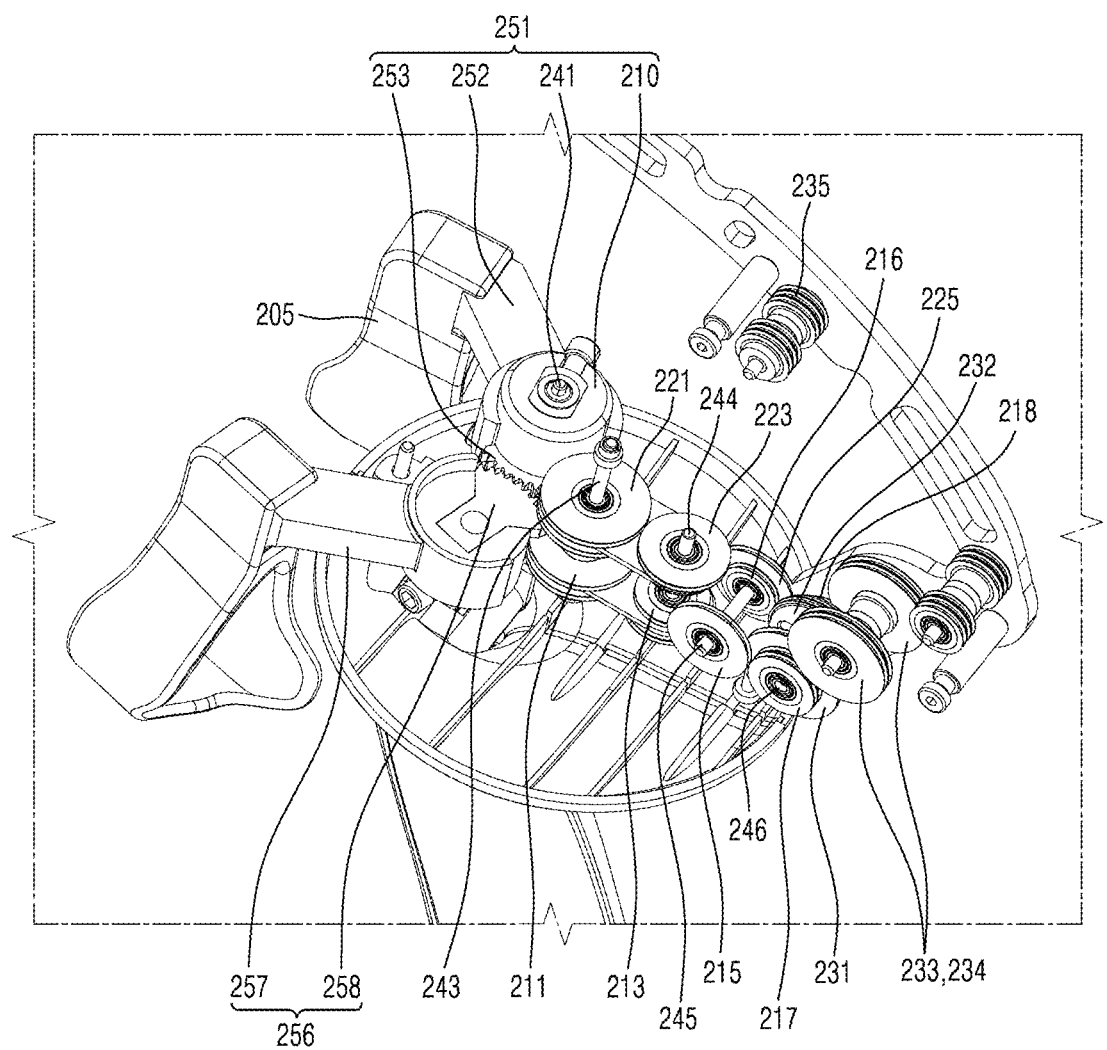
Figure 11:
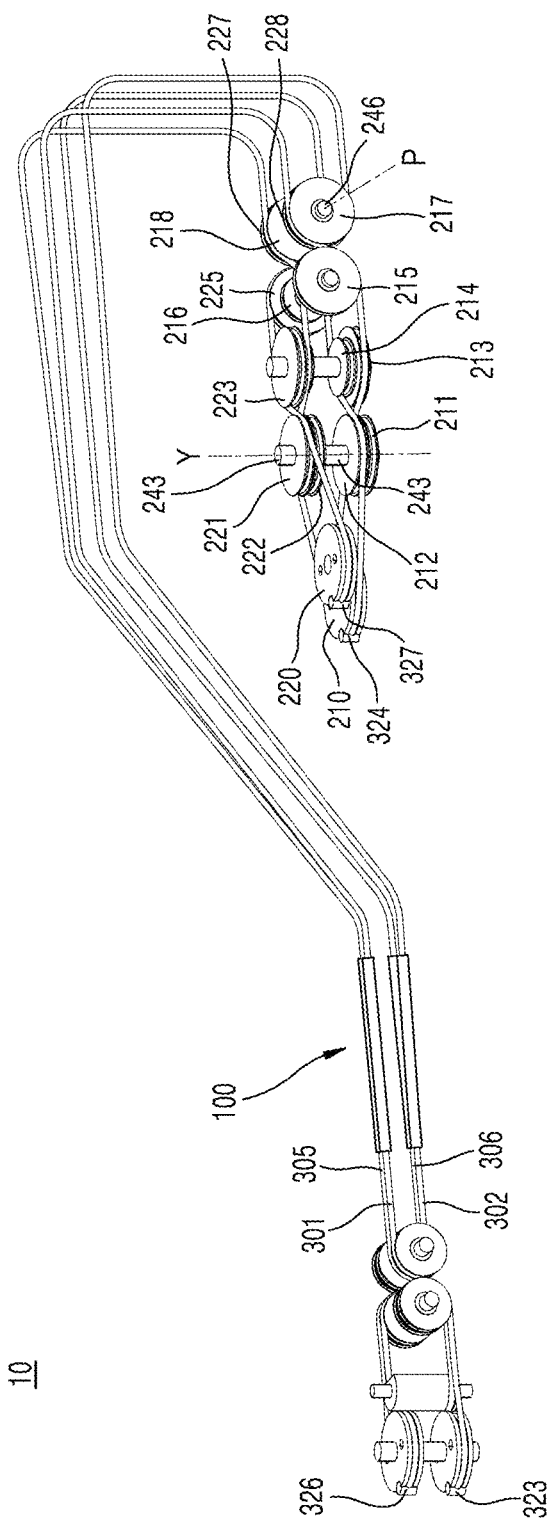
FIG. 11 is a view schematically illustrating only a configuration of pulleys and wires constituting joints of the surgical instrument illustrated in FIG. 2.

FIG. 2 is a perspective view illustrating a surgical instrument according to a first embodiment of the present disclosure. FIG. 3 is a side view of the surgical instrument of FIG. 2. FIGS. 4 and 5 are perspective views illustrating an end tool of the surgical instrument of FIG. 2. FIG. 6 is an enlarged perspective view illustrating the end tool hub of the surgical instrument of FIG. 4. FIGS. 7 and 8 are plan views illustrating the end tool of the surgical instrument of FIG. 2. FIGS. 9 and 10 are perspective views illustrating a manipulation part of the surgical instrument of FIG. 2. FIG. 11 is a view schematically illustrating only a configuration of pulleys and wires constituting joints of the surgical instrument illustrated in FIG. 2.

First, referring to FIGS. 2 and 3, a surgical instrument 10 according to a first embodiment of the present disclosure includes an end tool 100, a manipulation part 200, a power transmission part 300, and a connection part 400.

Here, the connection part 400 is formed in the shape of a hollow shaft, and one or more wires and electric wires may be accommodated therein. The manipulation part 200 is coupled to one end portion of the connection part 400, the end tool 100 is coupled to the other end portion thereof, and the connection part 400 may serve to connect the manipulation part 200 and the end tool 100. Here, the connection part 400 of the surgical instrument 10 according to the first embodiment of the present disclosure includes a straight part 401 and a bent part 402, wherein the straight part 401 is formed at a side coupled to the end tool 100, and the bent part 402 is formed at a side to which the manipulation part 200 is coupled. As such, since the end portion of the connection part 400 at the side of the manipulation part 200 is formed to be bent, a pitch manipulation part 201, a yaw manipulation part 202, and an actuation manipulation part 203 may be formed along an extension line of the end tool 100 or adjacent to the extension line. From another perspective, it may be said that the pitch manipulation part 201 and the yaw manipulation part 202 are at least partially accommodated in a concave portion formed by the bent part 402. Due to the above-described shape of the bent part 402, the shapes and motions of the manipulation part 200 and the end tool 100 may be further intuitively matched with each other.

Meanwhile, a plane on which the bent part 402 is formed may be substantially the same plane as a pitch plane, that is, an XZ plane of FIG. 2. As such, as the bent part 402 is formed on substantially the same plane as the XZ plane, interference with the manipulation part may be reduced. Of course, for intuitive motions of the end tool and the manipulation part, any form other than the XZ plane may be possible.

Meanwhile, a connector 410 may be formed on the bent part 402. The connector 410 may be connected to an external power source (not shown), and the connector 410 may also be connected to the pair of jaws 103 via an electric wire 411/412, and may transmit, to the pair of jaws 103, electric energy supplied from the external power source (not shown).

The manipulation part 200 is formed at the one end portion of the connection part 400 and provided as an interface to be directly controlled by a medical doctor, for example, a tongs shape, a stick shape, a lever shape, or the like, and when the medical doctor controls the manipulation part 200, the end tool 100, which is connected to the interface and inserted into the body of a surgical patient, performs a certain motion, thereby performing surgery. Here, the manipulation part 200 is illustrated in FIG. 2 as being formed in a handle shape that is rotatable while the finger is inserted therein, the concept of the present disclosure is not limited thereto, and various types of manipulation parts that are connected to the end tool 100 and manipulate the end tool 100 may be possible.

The end tool 100 is formed on the other end portion of the connection part 400, and performs necessary motions for surgery by being inserted into a surgical site. In an example of the end tool 100, as illustrated in FIG. 2, a pair of jaws 103 for performing a grip motion may be used. However, the concept of the present disclosure is not limited thereto, and various devices for performing surgery may be used as the end tool 100. For example, a configuration of a cantilever cautery may also be used as the end tool. The end tool 100 is connected to the manipulation part 200 by the power transmission part 300, and receives a driving force of the manipulation part 200 through the power transmission part 300 to perform a motion necessary for surgery, such as gripping, cutting, suturing, or the like.

Here, the end tool 100 of the surgical instrument 10 according to the first embodiment of the present disclosure is formed to be rotatable in at least one direction, for example, the end tool 100 may perform a pitch motion around a Y-axis of FIG. 2 and simultaneously perform a yaw motion and an actuation motion around a Z-axis of FIG. 2.

Here, each of the pitch, yaw, and actuation motions used in the present disclosure are defined as follows.

First, the pitch motion means a motion of the end tool 100 rotating in a vertical direction with respect to an extension direction of the connection part 400 (an X-axis direction of FIG. 2), that is, a motion rotating around the Y-axis of FIG. 2. In other words, the pitch motion means a motion of the end tool 100, which is formed to extend from the connection part 400 in the extension direction of the connection part 400 (the X-axis direction of FIG. 2), rotating vertically around the Y-axis with respect to the connection part 400.

Next, the yaw motion means a motion of the end tool 100 rotating in the left and right directions, that is, a motion rotating around the Z-axis of FIG. 2, with respect to the extension direction of the connection part 400 (the X-axis direction of FIG. 2). In other words, the yaw motion means a motion of the end tool 100, which extends from the connection part 400 in the extension direction of the connection part 400 (the X-axis direction of FIG. 2), rotating horizontally around the Z-axis with respect to the connection part 400. That is, the yaw motion means a motion of the two jaws 103, which are formed on the end tool 100, rotating around the Z-axis in the same direction.

Meanwhile, the actuation motion may mean a motion of the end tool 100 rotating around the same shaft of rotation as that of the yaw motion, while the two jaws 103 rotating in the opposite directions so as to be closed or opened. That is, the actuation motion means rotating motions of the two jaws 103, which are formed on the end tool 100, in the opposite directions around the Z-axis.

The power transmission part 300 may connect the manipulation part 200 to the end tool 100, transmit the driving force of the manipulation part 200 to the end tool 100, and include a plurality of wires, pulleys, links, sections, gears, or the like.

The end tool 100, the manipulation part 200, and the power transmission part 300 of the surgical instrument 10 of FIG. 2 will be described in detail later.

(Intuitive Driving)

Hereinafter, intuitive driving of the surgical instrument 10 of the present disclosure will be described.

First, while holding a first handle 204 with the palm of the hand, the user may rotate a first handle 204 around the Y-axis (i.e., a rotation shaft 246) to perform a pitch motion, and rotate the first handle 204 around the Z-axis (i.e., a rotation shaft 243) to perform a yaw motion. In addition, the user may perform an actuation motion by manipulating the actuation manipulation part 203 while inserting the thumb and the index finger into a first actuation extension part 252 and/or a second actuation extension part 257 in the form of a hand ring formed at one end portion of the actuation manipulation part 203.

Here, in the surgical instrument 10 according to the first embodiment of the present disclosure, when the manipulation part 200 is rotated in one direction with respect to the connection part 400, the end tool 100 is rotated in a direction that is intuitively the same as a manipulation direction of the manipulation part 200. In other words, when the first handle 204 of the manipulation part 200 is rotated in one direction, the end tool 100 is also rotated in a direction intuitively the same as the one direction, so that a pitch motion or a yaw motion is performed. Here, the phrase "intuitively the same direction" may be further explained as meaning that a direction of movement of the user's finger gripping the manipulation part 200 and a direction of movement of a distal end of the end tool 100 form substantially the same direction. Of course, "the same direction" as used herein may not be a perfectly matching direction on a three-dimensional coordinate, and may be understood to be equivalent to the extent that, for example, when the user's finger moves to the left, the distal end of the end tool 100 is moved to the left, and when the user's finger moves down, the end portion of the end tool 100 is moved down.

In addition, to this end, in the surgical instrument 10 according to the first embodiment of the present disclosure, the manipulation part 200 and the end tool 100 are formed in the same direction with respect to a plane perpendicular to the extension axis (X-axis) of the connection part 400. That is, when viewed based on a YZ plane of FIG. 2, the manipulation part 200 is formed to extend in a positive (+) X-axis direction, and the end tool 100 is also formed to extend in the positive (+) X-axis direction. In other words, it may be said that a formation direction of the end tool 100 on one end portion of the connection part 400 is the same as a formation direction of the manipulation part 200 on the other end portion of the connection part 400 on the basis of the YZ plane. Further, in other words, it may be said that the manipulation part 200 may be formed in a direction away from the body of a user holding the manipulation part 200, that is, in a direction in which the end tool 100 is formed. That is, in the parts such as the first handle 204, a first actuation manipulation part 251, a second actuation manipulation part 256, and the like, which are moved by the user's grip for actuation motion, yaw motion, and pitch motions, a corresponding portion that is moved for the motion is formed to extend in the positive (+) X-axis direction from the rotation center of a corresponding joint for the motion. In this manner, the manipulation part 200 may be configured in the same manner as the end tool 100 in which each moving portion is formed to extend in the positive (+) X-axis direction from the rotation center of a corresponding joint for the motion, and as described with reference to FIG. 1, the manipulation direction of the user may be identical to the operation direction of the end tool from the viewpoint of the rotation directions and the left and right directions. As a result, intuitively the same manipulation may be achieved.

In detail, in the case of the conventional surgical instrument, a direction in which a user manipulates the manipulation part is different from a direction in which the end tool is actually operated, that is, intuitively different from the direction in which the end tool is actually operated, and thus, a surgical operator may not easily intuitively manipulate the surgical instrument and may spend a long time to learn a skill of operating the end tool in desired directions, and in some cases, malfunctions may occur, which may cause damage to patients.

In order to address such problems, the surgical instrument 10 according to the first embodiment of the present disclosure is configured such that the manipulation direction of the manipulation part 200 and the operation direction of the end tool 100 are intuitively identical to each other. To this end, the manipulation part 200 is configured like the end tool 100, that is, in the manipulation part 200, portions that are actually moved for actuation, yaw, and pitch motions extend respectively from rotation centers of corresponding joints in the positive (+) X-axis direction.

Hereinafter, the end tool 100, the manipulation part 200, the power transmission part 300, and the like of the surgical instrument 10 of FIG. 2 will be described in more detail.

(Power Transmission Part)

Hereinafter, the power transmission part 300 of the surgical instrument 10 of FIG. 2 will be described in more detail.

Referring to FIGS. 2 to 11, and the like, the power transmission part 300 of the surgical instrument 10 according to an embodiment of the present disclosure may include a wire 301, a wire 302, a wire 303, a wire 304, a wire 305, and a wire 306.

Here, the wires 301 and 305 may be paired to serve as first jaw wires. The wires 302 and 306 may be paired to serve as second jaw wires. Here, the components encompassing the wires 301 and 305, which are first jaw wires, and the wires 302 and 306, which are second jaw wires, may be referred to as jaw wires. In addition, the wires 303 and 304 may be paired to serve as pitch wires.

Further, the power transmission part 300 of the surgical instrument 10 according to an embodiment of the present disclosure may include a coupling member 321, a coupling member 322, a coupling member 323, a coupling member 324, a coupling member 326, a coupling member 327 that are coupled to respective end portions of the wires to respectively couple the wires to the pulleys. Here, each of the coupling members may have various shapes as necessary, such as a ball shape, a tube shape, and the like.

Here, in the end tool 100 side, the coupling member 321 and the coupling member 322 may serve as a pitch wire-end tool coupling member, the coupling member 323 may serve as a first jaw wire-end tool coupling member, the coupling member 326 may serve as a second jaw wire-end tool coupling member.

Further, in the manipulation part 200 side, the coupling member 324 may serve as a first jaw wire-manipulation part coupling member, and the coupling member 327 may serve as a second jaw wire-manipulation part coupling member. In addition, although not shown in the drawings, a pitch wire-manipulation part coupling member may be further formed in the manipulation part 200 side.

The coupling relationship between the wires, the coupling members, and the respectively pulleys will be described in detail as follows.

First, the wires 301 and 305, which are first jaw wires, may be a single wire. The coupling member 323, which is a first jaw wire-end tool coupling member, is inserted at an intermediate point of the first jaw wire, which is a single wire, and the coupling member 323 is crimped and fixed, and then, both strands of the first jaw wire centered on the coupling member 323 may be referred to as the wire 301 and the wire 305, respectively.

Alternatively, the wires 301 and 305, which are first jaw wires, may also be formed as separate wires, and connected by the coupling member 323.

In addition, by coupling the coupling member 323 to a pulley 111, the wires 301 and 305 may be fixedly coupled to the pulley 111. This allows the pulley 111 to rotate as the wires 301 and 305 are pulled and released.

Meanwhile, the first jaw wire-manipulation part coupling member 324 may be coupled to end portions of the wires 301 and 305, which are opposite to one end portions to which the coupling member 323 is coupled.

In addition, by coupling the first jaw wire-manipulation part coupling member 324 to a pulley 210 as described above, the wires 301 and 305 may be fixedly coupled to the pulley 210 As a result, when the pulley 210 is rotated by a motor or a human force, the pulley 111 of the end tool 100 may be rotated as the wire 301 and the wire 305 are pulled and released.

In the same manner, each of the wires 302 and 306, which are second jaw wires, is coupled to the coupling member 326, which is a second jaw wire-end tool coupling member, and the second jaw wire-manipulation part coupling member 327. In addition, the coupling member 326 is coupled to a pulley 121, and the second jaw wire-manipulation part coupling member 327 is coupled to a pulley 220. As a result, when the pulley 220 is rotated by a motor or a human force, the pulley 121 of the end tool 100 may be rotated as the wire 302 and the wire 306 are pulled and released.

In the same manner, the wires 303 and 304, which are pitch wires, are respectively coupled to the coupling member 321 and the coupling member 322, which is a pitch wire-end tool coupling member, and the pitch wire-manipulation part coupling member (not shown). In addition, the coupling member 321 and the coupling member 322 are coupled to a pulley 131, and the pitch wire-manipulation part coupling member (not shown) is coupled to a pulley 231. As a result, when the pulley 231 is rotated by a motor or a human force, the pulley 131 of the end tool 100 may be rotated as the wire 303 and the wire 304 are pulled and released.

(End Tool)

Hereinafter, the end tool 100 of the surgical instrument 10 of FIG. 2 will be described in more detail.

FIGS. 4 and 5 are perspective views illustrating the end tool of the surgical instrument of FIG. 2, FIG. 6 is an enlarged perspective view illustrating the end tool hub of the surgical instrument of FIG. 4, and FIGS. 7 and 8 are plan views illustrating the end tool of the surgical instrument of FIG. 2.

Here, FIG. 4 illustrates a state in which the end tool hub 180 and the pitch hub 107 are coupled, and FIG. 5 illustrates a state in which the end tool hub 180 and the pitch hub 107 are removed. Also, FIG. 7 is a view mainly showing wires, and FIG. 8 is a view mainly sowing pulleys.

Referring to FIGS. 4 through 8, the end tool 100 according to a first embodiment of the present disclosure includes a pair of jaws, that is, a first jaw 101 and a second jaw 102 for performing a grip motion. Here, each of the first jaw 101 and the second jaw 102, or a component encompassing the first jaw 101 and the second jaw 102 may be referred to as a jaw 103.

In addition, the end tool 100 may include a pulley 111, a pulley 113, a pulley 114, a pulley 115, and a pulley 116 related to a rotational motion of the first jaw 101. Furthermore, the end tool 100 may include a pulley 121, a pulley 123, a pulley 124, a pulley 125, and a pulley 126 related to a rotational motion of the second jaw 102.

Here, pulleys facing each other are shown disposed in parallel to each other, but are not limited thereto, and the location and size of each pulley may vary to be appropriate for the configuration of the end tool.

Also, the end tool 100 according to the first embodiment of the present disclosure may include an end tool hub 180 and a pitch hub 107.

A rotation shaft 141, which will be described later, may be inserted through the end tool hub 180. The pulley 111 and the pulley 121 that are axially coupled to the rotation shaft 141, and at least portions of the first jaw 101 and the second jaw 102 that are coupled to the pulleys 111 and 121 may be accommodated in the end tool hub 180. Here, in one embodiment of the present disclosure, the end tool hub 180 is provided with a guide part 183 that functions as an auxiliary pulley. That is, the guide part 183 that guides the paths of the wire 305 and the wire 302 may be disposed in the end tool hub 180. The guide part 183 of the end tool hub 180 may change the paths of the wires by acting as a kind of auxiliary pulley. The guide part 183 of the end tool hub 180 that plays the role of the auxiliary pulley will be explained in more detail later.

Meanwhile, the pulley 131 that functions as an end tool pitch pulley may be disposed on one end portion of the end tool hub 180. As illustrated in FIG. 4, the pulley 131 may be formed integrally with the end tool hub 180. In this case, the pulley 131 may be disposed inside the end tool hub 180 in the form of a kind of guide channel to guide the paths of the wire 303 and the wire 304. Alternatively, the pulley 131 may be formed as a separate member from the end tool hub 180 and may be coupled to the end tool hub 180. The wire 303 and the wire 304 are coupled to the pulley 131, which acts as an end tool pitch pulley. The pulley 131 performs a pitch motion while rotating around the rotation shaft 143.

The rotation shaft 143 and a rotation shaft 144 may be inserted through the pitch hub 107, and the pitch hub 107 may be axially coupled to the end tool hub 180 and the pulley 131 by the rotation shaft 143. Accordingly, the end tool hub 180 and the pulley 131 may be formed to be pitch-rotated around the rotation shaft 143 with respect to the pitch hub 107.

In addition, the pitch hub 107 may accommodate therein at least portions of the pulley 113, pulley 114, pulley 123, and pulley 124 axially coupled to the rotation shaft 143. Also, the pitch hub 107 may accommodate therein at least portions of the pulley 115, pulley 116, pulley 125, and pulley 126 axially coupled to the rotation shaft 144.

In addition, the end tool 100 of the first embodiment of the present disclosure may include a rotation shaft 141, a rotation shaft 143, and a rotation shaft 144. As described above, the rotation shaft 141 may be inserted through the end tool hub 180, and the rotation shaft 143 and the rotation shaft 144 may be inserted through the pitch hub 107.

The rotation shaft 141, the rotation shaft 143, and the rotation shaft 144 may be disposed sequentially in a direction from a distal end 104 to a proximal end 105 of the end tool 100. Accordingly, starting from the distal end 104, the rotation shaft 141 may be referred to as a first pin, the rotation shaft 143 may be referred to as a third pin, and the rotation shaft 144 may be referred to as a fourth pin. In addition, the guide part 183 of the end tool hub 180 disposed between the rotation shaft 141 and the rotation shaft 143 may serve as a second pin.

Here, the rotation shaft 141 may function as an end tool jaw pulley rotation shaft, the rotation shaft 143 may function as an end tool pitch rotation shaft, and the rotation shaft 144 may function as an end tool pitch auxiliary rotation shaft of the end tool 100. Additionally, the guide part 183 of the end tool hub 180 may function as an end tool jaw auxiliary pulley rotation shaft.

One or more pulleys may be fitted to each of these rotation shafts 141, 143, and 144, which will be described in detail below.

The pulley 111 functions as an end tool first jaw pulley, and the pulley 121 functions as an end tool second jaw pulley. The pulley 111 may also be referred to as a first jaw pulley, and the pulley 121 may also be referred to as a second jaw pulley. These two components may be collectively referred to as an end tool jaw pulley.

The pulley 111 and the pulley 121, which are end tool jaw pulleys, are disposed to face each other and to be rotatable independently of each other around the rotation shaft 141, which is an end tool jaw pulley rotation shaft. Here, in the drawings, the pulley 111 and the pulley 121 rotate around one rotation shaft 141, but of course, each jaw pulley may be rotatable around a separate shaft. Here, the first jaw 101 may be fixedly coupled to the pulley 111 to rotate together with the pulley 111, and the second jaw 102 may be fixedly coupled to the pulley 121 to rotate together with the pulley 121. A yaw motion and an actuation motion of the end tool 100 are carried out, in response to the rotation of the pulley 111 and the pulley 121. That is, a yaw motion is performed when the pulley 111 and the pulley 121 rotate in the same direction around the rotation shaft 141, and an actuation motion is performed when the pulley 111 and the pulley 121 rotate in opposite directions around the rotation shaft 141.

Here, the first jaw 101 and the pulley 111 may be formed as separate members and coupled to each other, or the first jaw 101 and the pulley 111 may be formed as a one-body. Likewise, the second jaw 102 and the pulley 121 may be formed as separate members and coupled to each other, or the second jaw 102 and the pulley 121 may be formed as a one-body.

The guide part 183 of the end tool hub 180 may be formed on one side of the pulley 111 and the pulley 121, which are end tool jaw pulleys, and may serve as end tool jaw auxiliary pulleys. Specifically, the guide part 183 of the end tool hub 180 may be located on one side of the pulley 111 and the pulley 121. The guide part 183 of the end tool hub 180 will be explained in more detail later.

The pulley 113 and the pulley 114 may function as end tool first jaw pitch main pulleys, and the pulley 123 and the pulley 124 may function as end tool second jaw pitch main pulleys. These two components may also be collectively referred to as an end tool jaw pitch main pulley.

The pulley 115 and the pulley 116 may function as end tool first jaw pitch sub pulleys, and the pulley 125 and the pulley 126 may function as end tool second jaw pitch sub pulleys. These two components may also be collectively referred to as an end tool jaw pitch sub pulley.

Hereinafter, components related to the rotation of the pulley 111 will be described.

The pulley 113 and the pulley 114 function as end tool first jaw pitch main pulleys. In other words, the pulley 113 and the pulley 114 function as main rotation pulleys for the pitch motion of the first jaw 101. Here, the wire 301, which is a first jaw wire, is wound around the pulley 113, and the wire 305, which is a first jaw wire, is wound around the pulley 114.

The pulley 115 and the pulley 116 function as end tool first jaw pitch sub pulleys. In other words, the pulley 115 and the pulley 116 function as sub rotation pulleys for the pitch motion of the first jaw 101. Here, the wire 301, which is a first jaw wire, is wound around the pulley 115, and the wire 305, which is a first jaw wire, is wound around the pulley 116.

Here, the pulley 113 and the pulley 114 are disposed to face each other on one side of the pulley 111. Here, the pulley 113 and the pulley 114 are disposed to be rotatable independently of each other around the rotation shaft 143 that is an end tool pitch rotation shaft. Here, the pulley 115 and the pulley 116 are disposed to face each other on one side of the pulley 113 and one side of the pulley 114, respectively. Here, the pulley 115 and the J15 pulley 123 J25 are disposed to be rotatable independently of each other around the rotation shaft 144 that is an end tool pitch auxiliary rotation shaft. Here, in the drawings, it is illustrated that the pulley 113, the pulley 115, the pulley 114, and the pulley 116 are all formed to be rotatable around a Y-axis direction, but the concept of the present disclosure is not limited thereto, and the rotation shafts of the respective pulleys may be formed in various directions according to configurations thereof.

The wire 301, which is a first jaw wire, is sequentially wound to make contact with at least portions of the pulley 115, the pulley 113, and the pulley 111. In addition, the wire 305 connected to the wire 301 by the coupling member 323 is sequentially wound to make contact with at least portions of the pulley 111, the guide part 183, the pulley 114, and the pulley 116.

From another perspective, the wires 301 and 305, which are first jaw wires, are sequentially wound to make contact with at least portions of the pulley 115, the pulley 113, the pulley 111, the guide part 183, the pulley 114, and the pulley 116. The wire 301 and the wire 305 are formed to be movable along the above pulleys while rotating the pulleys.

Accordingly, when the wire 301 is pulled toward an arrow 301 of FIG. 7, the coupling member 323, to which the wire 301 is coupled, and the pulley 111 coupled to the coupling member 323 are rotated in a direction of an arrow L of FIG. 7. On the other hand, when the wire 305 is pulled toward an arrow 305 of FIG. 7, the coupling member 323, to which the wire 305 is coupled, and the pulley 111 coupled to the coupling member 323 are rotated in a direction of an arrow R of FIG. 7.

Hereinafter, components related to the rotation of the pulley 121 will be described.

The pulley 123 and the pulley 124 function as end tool second jaw pitch main pulleys. In other words, the pulley 123 and the pulley 124 function as main rotation pulleys for the pitch motion of the second jaw 102. Here, the wire 306, which is a second jaw wire, is wound around the pulley 123, and the wire 302, which is a second jaw wire, is wound around the pulley 124.

The pulley 125 and the pulley 126 function as end tool second jaw sub pulleys. In other words, the pulley 125 and the pulley 126 function as sub rotation pulleys for the pitch motion of the second jaw 102. Here, the wire 306, which is a second jaw wire, is wound around the pulley 125, and the wire 302, which is a second jaw wire, is wound around the pulley 126.

The pulley 123 and the pulley 124 are disposed to face each other on one side of the pulley 121. Here, the pulley 123 and the pulley 124 are disposed to be rotatable independently of each other around the rotation shaft 143 that is an end tool pitch rotation shaft. Here, the pulley 125 and the pulley 126 are disposed to face each other on one side of the pulley 123 and one side of the pulley 124, respectively. Here, the pulley 125 and the pulley 126 are disposed to be rotatable independently of each other around the rotation shaft 144 that is an end tool pitch auxiliary rotation shaft. Here, in the drawings, it is illustrated that the pulley 123, the pulley 125, the pulley 124, and the pulley 126 are all formed to be rotatable around the Y-axis direction, but the concept of the present disclosure is not limited thereto, and the rotation shafts of the respective pulleys may be formed in various directions according to configurations thereof.

The wire 306, which is a second jaw wire, is sequentially wound to make contact with at least portions of the pulley 125, the pulley 123, and the pulley 121. In addition, the wire 302 connected to the wire 306 by the coupling member 326 is sequentially wound to make contact with at least portions of the pulley 121, the guide part 183, the pulley 124, and the pulley 126.

From another perspective, the wires 306 and 302, which are second jaw wires, are sequentially wound to make contact with at least portions of the pulley 125, the pulley 123, the pulley 121, the guide part 183, the pulley 124, and the pulley 126. The wire 306 and the wire 302 are formed to be movable along the above pulleys while rotating the pulleys.

Accordingly, when the wire 306 is pulled toward an arrow 306 of FIG. 7, the coupling member 322, to which the wire 306 is coupled, and the pulley 121 coupled to the coupling member 323 are rotated in the direction of the arrow R of FIG. 7. On the other hand, when the wire 302 is pulled toward an arrow 302 of FIG. 7, the coupling member 326, to which the wire 302 is coupled, and the pulley 121 coupled to the coupling member 323 are rotated in the direction of the arrow L of FIG. 7.

Hereinafter, the end tool hub 180 according to one embodiment of the present disclosure will be described in more detail, and in particular, a description will be given, focusing on the guide part 183 of the end tool hub 180, which serves as an auxiliary pulley.

The end tool hub 180 includes a pair of jaw pulley coupling parts 181 and 182, a guide part 183, a guide groove 184, and a pitch pulley part 185.

Specifically, the pair of jaw pulley coupling parts 181 and 182 are formed to face each other to accommodate the pulley 111 and the pulley 121 therein. In addition, a through hole is formed through each of the jaw pulley coupling parts 181 and 182, and the rotation shaft 141 is inserted through the jaw pulley coupling parts 181 and 182 and the pulleys 111 and 121 to axially couple the pulley coupling parts 181 and 182 and the pulleys 111 and 121.

The pair of jaw pulley coupling parts 181 and 182 are connected by the guide part 183. That is, the pair of jaw pulley coupling parts 181 and 182 that are parallel to each other may be coupled to each other by the guide part 183, which is formed in a direction approximately perpendicular to the pair of jaw pulley coupling parts 181 and 182. Accordingly, the pair of jaw pulley coupling parts 181 and 182 may form a shape like "D" together with the guide part 183, such that the pulley 111 and the pulley 121 are accommodated.

To explain this from another perspective, it may be understood that the pair of jaw pulley coupling parts 181 and 182 extend in an X-axis direction from both end portions of the guide part 183 that is formed long in a Z-axis direction.

Here, the guide part 183 may be formed in a cylindrical shape with an approximately semicircular cross-section. This semicircular portion may be disposed to protrude toward the pulley 111 and the pulley 121. Expressing this from another perspective, it may be expressed that the guide part 183 protrudes toward a space defined by the pair of jaw pulley coupling parts 181 and 182 and the guide part 183. Expressing this from another perspective, it may be expressed that an area of the guide part 183, which is adjacent to the jaw pulley coupling parts 181 and 182, has a cross-section curved at a predetermined curvature.

Or, to express this from another perspective, it may also be said that the guide part 183 has the wire 305 and the wire 302 wound around its outer peripheral surface and thus functions as a kind of pulley member for guiding the paths of the wire 305 and the wire 302. However, here, it may be understood that the guide part 183 is not a member that rotates around a predetermined shaft like a pulley in the original sense but is fixed as a portion of the end tool hub 180, with a wire wound therearound, to similarly perform some of functions of a pulley for guiding the path of the wire.

Here, in the drawings, the guide part 183 is shown formed in a cylindrical shape with an approximately semicircular cross-section. That is, at least a portion of the cross-section of the guide part 183 on an XY plane is shown forming a predetermined arcuate shape. However, the concept of the present disclosure is not limited thereto, and the guide part 183 may be formed to have a cross-section with a predetermined curvature, such as an oval or parabola, or may be formed in the form of a polygonal pillar with edges rounded to a certain extent, to have various shapes and sizes suitable for guiding the paths of the wires 305 and 302.

Here, a guide groove 184 may be further formed in a portion of the guide part 183 that is in contact with the wire 305 and the wire 302, to better guide the paths of the wire 305 and the wire 302. The guide groove 184 may be formed in the form of a groove that is recessed to a certain extent from a protruded surface of the guide part 183.

Here, the drawings show that the guide groove 184 is formed in the entire arcuate surface of the guide part 183, but the concept of the present disclosure is not limited thereto. The guide groove 194 may alternatively be formed only in a portion of the arcuate surface of the guide part 183, if necessary.

By further forming the guide groove 184 in the guide part 183 in this way, unnecessary friction with the wires may be reduced, thereby improving the durability of the wires.

A pitch pulley part 185 may be further formed on the guide part 183 in a direction opposite to a direction that the jaw pulley coupling parts 181 and 182 are formed. The pitch pulley part 185 may be provided with a pulley 131 as a pitch pulley, around which the wires 303 and 304 as pitch wires are wound. However, here, it may be understood that the pulley 131 is not a member that rotates around a predetermined shaft like a pulley in the original sense but is fixed as a portion of the end tool hub 180, with a wire wound therearound, to similarly perform some of functions of a pulley for guiding the path of the wire. That is, the pulley 131 may be formed in the form of a kind of groove in the pitch pulley part 185 of the end tool hub 180, and may function as a guide channel of the wire 303 and the wire 304. Here, the pitch pulley part 185 may be formed on the XZ plane. In addition, a through hole through which the rotation shaft 143 can be inserted may be formed through the pitch pulley part 185.

Meanwhile, although not illustrated in the drawings, the pitch pulley part and the pitch pulley may be formed as separate members and coupled to each other, and the rotation shaft 143 may be formed to be inserted through the pitch pulley part and the pulley.

Hereinafter, the role and function of the guide part 183 will be described in more detail.

The guide part 183 may be in contact with the wire 305 and the wire 302 to change the disposition paths of the wire 305 and the wire 302 to a certain extent, thereby playing a role of expanding the radius of rotation of each of the first jaw 101 and the second jaw 102.

That is, when the auxiliary pulley or guide part 183 is not disposed, each of the pulley 111, which is the first jaw pulley, and the pulley 121, which is the second jaw pulley, is rotatable up to a right angle, but in one embodiment of the present disclosure, the maximum rotation angle of each pulley can increase by virtue of the guide part 183 additionally disposed in the end tool hub 180.

This enables a motion that two jaws of the end tool 100 must be apart from each other for an actuation motion in a state where the two jaws are yaw-rotated by 90°. In other words, with the configuration of the guide part 183 of the end tool hub 180, the range of yaw rotation enabling the actuation motion may be expanded.

Furthermore, without addition of a separate structure such as an auxiliary pulley, the guide part 183 may be formed in the existing end tool hub 180, resulting in expanding the rotation range without additional components and manufacturing processes.

In this way, without the additional structure for expanding the rotation angle, the number of components can be reduced and the manufacturing process can be simplified. Also, as the length of the end tool is shortened by the size of the auxiliary pulley, the length of the end tool upon performing the pitch motion can be shortened, which may more facilitate surgical operations to be performed in a narrow space.

This will be explained in more detail as follows.

The end tool 100 of the surgical instrument according to one embodiment of the present disclosure includes the guide part 183 that is disposed on an inner wall of the end tool hub 180 to change the path of the wire, thereby changing the disposition path of the wire without a separate structure. In this way, the guide part 183 is formed in the end tool hub 180 to change the disposition paths of the wire 305 and the wire 302 to a certain extent. Accordingly, a tangential direction of the wire 305 and the wire 302 may be changed, and thus the rotation angle of the coupling member 323 and the coupling member 326 for coupling the wires to the pulleys is increased.

That is, the coupling member 326 that couples the wire 302 to the pulley 121 is rotatable until it is located on a common internal tangent of the pulley 121 and the guide part 183. Likewise, the coupling member (see 323 in FIG. 11) that couples the wire 305 to the pulley 111 is rotatable until it is located on a common internal tangent of the pulley 111 and the guide part 183. This may increase the rotation angle of the coupling member (see 323 in FIG. 11).

To explain this from another perspective, the wire 301 and the wire 305 wound around the pulley 111 by the guide part 183 are disposed on one side based on a plane that is perpendicular to the Y axis and passes through the X axis. Simultaneously, the wire 302 and the wire 306 wound around the pulley 121 by the guide part 183 are disposed on another side based on a plane that is perpendicular to the Y axis and passes through the X axis.

In other words, the pulleys 113 and 114 are disposed on one side based on the plane that is perpendicular to the Y axis and passes through the X axis, and the pulleys 123 and 124 are disposed on another side based on the plane that is perpendicular to the Y axis and passes through the X axis.

In other words, the wire 305 is located on the internal tangent of the pulley 111 and the guide part 183, and the rotation angle of the pulley 111 is increased by the guide part 183. Furthermore, the wire 302 is located on the internal tangent of the pulley 121 and the guide part 183, and the rotation angle of the pulley 121 is increased by the guide part 183.

Compared to a surgical instrument with a separate auxiliary pulley, the length of the end tool may be shortened in the surgical instrument according to the embodiment of the present disclosure, in which an auxiliary pulley is not disposed and the guide part 183 is disposed on the inner wall of the end tool hub 180 to change the path of the wire. As the length of the end tool is shorted, the operator's manipulation may become easier when performing a surgery in a narrow surgical space within the human body, and the side effects of the surgery may be reduced.

In this way, according to the present disclosure, the radius of rotation of the pulley 111 as the first jaw pulley and the pulley 121 as the second jaw pulley can be widened, thereby obtaining an effect of increasing a yaw-motion range in which a normal opening and closing actuation motion is performed.

Hereinafter, the pitch motion according to the present disclosure will be described in more detail.

Meanwhile, when the wire 301 is pulled toward an arrow 301 of FIG. 7 and simultaneously the wire 305 is pulled toward an arrow 305 of FIG. 7 (i.e., when both strands of the first jaw wire are pulled), the pulley 111, to which the wire 301 and the wire 305 are fixedly coupled, and the end tool hub 180, to which the pulley 111 is coupled, are rotated together in a counterclockwise direction around the rotation shaft 143, because the wire 301 and the wire 305, as illustrated in FIG. 5, are wound around lower portions of the pulley 113 and the pulley 114 rotatable around the rotation shaft 143, which is an end tool pitch rotation shaft. Accordingly, the end tool 100 performs a pitch motion while rotating downward. In this case, since the second jaw 102 and the wires 302 and 306 fixedly coupled to the second jaw 102 are wound around upper portions of the pulleys 123 and 124 rotatable around the rotation shaft 143, the wire 302 and the wire 306 are unwound in the opposite directions of 302 and 306, respectively.

In contrast, when the wire 302 is pulled toward an arrow 302 of FIG. 7 and simultaneously the wire 306 is pulled toward an arrow 306 of FIG. 7, the pulley 121, to which the wire 302 and the wire 306 are fixedly coupled, and the end tool hub 180, to which the pulley 121 is coupled, are rotated together in a clockwise direction around the rotation shaft 143, because the wire 302 and the wire 306, as illustrated in FIG. 5, are wound around upper portions of the pulley 123 and the pulley 124 rotatable around the rotation shaft 143, which is an end tool pitch rotation shaft. Accordingly, the end tool 100 performs a pitch motion while rotating upward. In this case, since the first jaw 101 and the wires 301 and 305 fixedly coupled to the first jaw 101 are wound around lower portions of the pulleys 113 and 114 rotatable around the rotation shaft 143, the wire 302 and the wire 306 are moved in the opposite directions of 301 and 305, respectively.

Meanwhile, the end tool 100 of the surgical instrument 10 according to the present disclosure may further include the pulley 131, which is an end tool pitch pulley, and the manipulation part 200 may further include a pulley 231 and a pulley 232, which are manipulation part pitch pulleys. The power transmission part 300 may further include a wire 303 and a wire 304 that are pitch wires. In detail, the pulley 131 of the end tool 100 may be rotatable around the rotation shaft 143, which is an end tool pitch rotation shaft, and may be integrally formed with the end tool hub 180 (or fixedly coupled to the end tool hub 180). In addition, the wire 303 and the wire 304 may serve to connect the pulley 131 of the end tool 100 to the pulley 231 and the pulley 232 of the manipulation part 200.

Accordingly, when the pulley 231 and the pulley 232 of the manipulation part 200 rotate, the rotation of the pulley 231 and the pulley 232 is transmitted to the pulley 131 of the end tool 100 through the wire 303 and the wire 304, so that the pulley 131 is rotated together. Consequently, the end tool 100 performs a pitch motion while rotating.

That is, as the surgical instrument 10 according to the first embodiment of the present disclosure includes the pulley 131 of the end tool 100, the pulleys 231 and 232 of the manipulation part 200, and the wires 303 and 304 of the power transmission part 300, to transmit a driving force for a pitch motion, the driving force for the pitch motion of the manipulation part 200 may be more completely transmitted to the end tool 100, thereby improving motion reliability.

Here, the diameters of the pulley 113, the pulley 114, the pulley 123, and the pulley 124, which are end tool jaw pitch main pulleys, and the diameter of the pulley 131, which is an end tool pitch pulley, may be the same as or different from each other. In this case, a ratio of the diameter of the end tool pitch pulley to the diameter of the end tool jaw pitch main pulley may be the same as a ratio of the diameter of the manipulation part pitch main pulley to the diameter of the manipulation part pitch pulley of the manipulation part 200, which will be described later.

(Manipulation Part)

FIGS. 9 and 10 are perspective views illustrating the manipulation part of the surgical instrument of FIG. 2. FIG. 11 is a view schematically illustrating only a configuration of pulleys and wires constituting joints of the surgical instrument illustrated in FIG. 2.

Referring to FIGS. 2 to 11, the manipulation part 200 of the surgical instrument 10 according to the first embodiment of the present disclosure includes a first handle 204 that a user can grip, the actuation manipulation part 203 configured to control an actuation motion of the end tool 100, the yaw manipulation part 202 configured to control a yaw motion of the end tool 100, and the pitch manipulation part 201 configured to control a pitch motion of the end tool 100.

The manipulation part 200 may include the pulley 210, a pulley 211, a pulley 212, a pulley 213, a pulley 214, a pulley 215, a pulley 216, a pulley 217, and a pulley 218 that are related to a rotational motion of the first jaw 101. In addition, the manipulation part 200 may include the pulley 220, a pulley 221, a pulley 222, a pulley 223, a pulley 224, a pulley 225, a pulley 226, a pulley 227, and a pulley 228 that are related to a rotational motion of the second jaw 102. In addition, the manipulation part 200 may include the pulley 231, the pulley 232, a pulley 233, and a pulley 234 that are related to a pitch motion thereof. In addition, the manipulation part 200 may include a pulley 235, which is a relay pulley disposed at some places along the bent part 402 of the connection part 400.

Here, the pulleys facing each other are illustrated in the drawings as being formed parallel to each other, but the concept of the present disclosure is not limited thereto, and each of the pulleys may be variously formed with a position and a size suitable for the configuration of the manipulation part.

Further, the manipulation part 200 of the first embodiment of the present disclosure may include a rotation shaft 241, a rotation shaft 242, the rotation shaft 243, a rotation shaft 244, a rotation shaft 245, and the rotation shaft 246. Here, the rotation shaft 241 may function as a manipulation part first jaw actuation rotation shaft, and the rotation shaft 242 may function as a manipulation part second jaw actuation rotation shaft. In addition, the rotation shaft 243 may function as a manipulation part yaw main rotation shaft, and the rotation shaft 244 may function as a manipulation part yaw sub-rotation shaft. In addition, the rotation shaft 245 may function as a manipulation part pitch sub-rotation shaft, and the rotation shaft 246 may function as a manipulation part pitch main rotation shaft.

The rotation shaft 241/rotation shaft 242, the rotation shaft 243, the rotation shaft 244, the rotation shaft 245, and the rotation shaft 246 may be sequentially disposed from a distal end 205 of the manipulation part 200 toward a proximal end 206.

Each of the rotation shafts 241, 242, 243, 244, 245, and 246 may be fitted into one or more pulleys, which will be described in detail later.

The pulley 210 functions as a manipulation part first jaw actuation pulley, the pulley 220 functions as a manipulation part second jaw actuation pulley, and these components may also be collectively referred to as a manipulation part actuation pulley.

The pulley 211 and the pulley 212 function as manipulation part first jaw yaw main pulleys, the pulley 221 and the pulley 222 function as manipulation part second jaw yaw main pulleys, and these components may also be collectively referred to as a manipulation part yaw main pulley.

The pulley 213 and the pulley 214 function as manipulation part first jaw yaw sub-pulleys, the pulley 223 and the pulley 224 function as manipulation part second jaw yaw sub-pulleys, and these components may also be collectively referred to as a manipulation part yaw sub-pulley.

The pulley 215 and the pulley 216 function as manipulation part first jaw pitch sub-pulleys, the pulley 225 and the pulley 226 function as manipulation part second jaw pitch sub-pulleys, and these components may also be collectively referred to as a manipulation part pitch sub-pulley.

The pulley 217 and the pulley 218 function as manipulation part first jaw pitch main pulleys, and the pulley 227 and the pulley 228 function as manipulation part second jaw pitch main pulleys, and these components may also be collectively referred to as the manipulation part pitch main pulley.

The pulley 231 and the pulley 232 function as manipulation part pitch wire main pulleys, and the pulley 233 and the pulley 234 function as manipulation part pitch wire sub-pulleys.

The above components are categorized from the perspective of the manipulation part for each motion (pitch/yaw/actuation) as follows.

The pitch manipulation part 201 configured to control a pitch motion of the end tool 100 may include the pulley 215, the pulley 216, the pulley 217, the pulley 218, the pulley 225, the pulley 226, the pulley 227, the pulley 228, the pulley 231, the pulley 232, the pulley 234, and the pulley 235. In addition, the pitch manipulation part 201 may include the rotation shaft 245 and the rotation shaft 246. In addition, the pitch manipulation part 201 may further include a pitch frame 208.

The yaw manipulation part 202 configured to control a yaw motion of the end tool 100 may include the pulley 211, the pulley 212, the pulley 213, the pulley 214, the pulley 221, the pulley 222, the pulley 223, and the pulley 224. In addition, the yaw manipulation part 202 may include the rotation shaft 243 and the rotation shaft 244. In addition, the yaw manipulation part 202 may further include a yaw frame 207.

The actuation manipulation part 203 configured to control an actuation motion of the end tool 100 may include the pulley 210, the pulley 220, the rotation shaft 241, and the rotation shaft 242. In addition, the actuation manipulation part 203 may further include the first actuation manipulation part 251 and the second actuation manipulation part 256.

Hereinafter, each component of the manipulation part 200 will be described in more detail. The first handle 204 may be formed to be gripped by a user with the hand, and in particular, may be formed to be grasped by the user by wrapping the first handle 204 with his/her palm. In addition, the actuation manipulation part 203 and the yaw manipulation part 202 are formed on the first handle 204, and the pitch manipulation part 201 is formed on one side of the yaw manipulation part 202. In addition, the other end portion of the pitch manipulation part 201 is connected to the bent part 402 of the connection part 400.

The actuation manipulation part 203 includes the first actuation manipulation part 251 and the second actuation manipulation part 256. The first actuation manipulation part 251 includes the rotation shaft 241, the pulley 210, the first actuation extension part 252, and a first actuation gear 253. The second actuation manipulation part 256 includes the rotation shaft 242, the pulley 220, the second actuation extension part 257, and a second actuation gear 258. Here, end portions of the first actuation extension part 252 and the second actuation extension part 257 are formed in the shape of a hand ring, which may act as a second handle.

Here, the rotation shaft 241 and the rotation shaft 242, which are actuation rotation axes, may be formed to form a predetermined angle with an XY plane on which the connection part 400 is formed. For example, the rotation shaft 241 and the rotation shaft 242 may be formed in a direction parallel to the Z-axis, and in this state, when the pitch manipulation part 201 or the yaw manipulation part 202 is rotated, the coordinate system of the actuation manipulation part 203 may change relatively. Of course, the concept of the present disclosure is not limited thereto, and the rotation shaft 241 and the rotation shaft 242 may be formed in various directions so as to be suitable for a structure of the hand of the user gripping the actuation manipulation part 203 according to an ergonomic design.

Meanwhile, the pulley 210, the first actuation extension part 252, and the first actuation gear 253 are fixedly coupled to each other to be rotatable together around the rotation shaft 241. Here, the pulley 210 may be configured to be a single pulley or two pulleys fixedly coupled to each other.

Similarly, the pulley 220, the second actuation extension part 257, and the second actuation gear 258 are fixedly coupled to each other to be rotatable together around the rotation shaft 242. Here, the pulley 220 may be configured to be a single pulley or two pulleys fixedly coupled to each other.

Here, the first actuation gear 253 and the second actuation gear 258 are formed to be engaged with each other such that, when any one gear is rotated in one direction, the other gear is rotated together in a direction opposite to the one direction.

The yaw manipulation part 202 may include the rotation shaft 243, the pulleys 211 and 212, which are manipulation part first jaw yaw main pulleys, the pulleys 221 and 222, which are manipulation part second jaw yaw main pulleys, and the yaw frame 207. In addition, the yaw manipulation part 202 may further include the pulleys 213 and 214, which are manipulation part first jaw yaw sub-pulleys formed on one side of the pulleys 211 and 212, and the pulleys 223 and 224 that are manipulation part second jaw yaw sub-pulleys formed on one side of the pulleys 221 and 222. Here, the pulleys 213 and 214 and the pulleys 223 and 224 may be coupled to the pitch frame 208 to be described later.

Here, it is illustrated in the drawings that the yaw manipulation part 202 includes the pulleys 211 and 212 and the pulleys 221 and 222, wherein the pulleys 211 and 212 and the pulleys 221 and 222 are each provided with two pulleys formed to face each other and independently rotatable, but the concept of the present disclosure is not limited thereto. That is, one or more pulleys having the same diameter or different diameters may be provided according to the configuration of the yaw manipulation part 202.

In detail, the rotation shaft 243, which is a manipulation part yaw main rotation shaft, is formed on one side of the actuation manipulation part 203 on the first handle 204. At this time, the first handle 204 is formed to be rotatable around the rotation shaft 243.

Here, the rotation shaft 243 may be formed to form a predetermined angle with the XY plane on which the connection part 400 is formed. For example, the rotation shaft 243 may be formed in a direction parallel to the Z-axis, and in this state, when the pitch manipulation part 201 is rotated, the coordinate system of the rotation shaft 243 may change relatively as described above. Of course, the concept of the present disclosure is not limited thereto, and the rotation shaft 243 may be formed in various directions so as to be suitable for a structure of the hand of the user gripping the manipulation part 200 according to an ergonomic design.

Meanwhile, the pulleys 211 and 212 and the pulleys 221 and 222 are coupled to the rotation shaft 243 so as to be rotatable around the rotation shaft 243. In addition, the wire 301 or the wire 305, which is a first jaw wire, is wound around the pulleys 211 and 212, and the wire 302 or the wire 306, which is a second jaw wire, may be wound around the pulleys 221 and 222. In this case, the pulleys 211 and 212 and the pulleys 221 and 222 may each be configured as two pulleys formed to face each other and independently rotatable. Accordingly, a wire being wound and a wire being released may be wound around respective separate pulleys so that the wires may perform motions without interference with each other.

The yaw frame 207 rigidly connects the first handle 204, the rotation shaft 241, the rotation shaft 242, and the rotation shaft 243, so that the first handle 204, the yaw manipulation part 202, and the actuation manipulation part 203 are integrally yaw-rotated around the rotation shaft 243.

The pitch manipulation part 201 may include the rotation shaft 246, the pulley 217 and the pulley 218, which are manipulation part first jaw pitch main pulleys, the pulleys 227 and 228, which are manipulation part second jaw pitch main pulleys, and the pitch frame 208. In addition, the pitch manipulation part 201 may further include the rotation shaft 245, the pulleys 215 and 216, which are manipulation part first jaw pitch sub-pulleys formed on one side of the pulley 217 and the pulley 218, and the pulleys 225 and 226, which are manipulation part second jaw pitch sub-pulleys formed on one side of the pulley 227 and the pulley 228. The pitch manipulation part 201 may be connected to the bent part 402 of the connection part 400 through the rotation shaft 246.

In detail, the pitch frame 208 is a base frame of the pitch manipulation part 201, and the rotation shaft 243 is rotatably coupled to one end portion thereof. That is, the yaw frame 207 is formed to be rotatable around the rotation shaft 243 with respect to the pitch frame 208.

As described above, since the yaw frame 207 connects the first handle 204, the rotation shaft 243, the rotation shaft 241, and the rotation shaft 242, and the yaw frame 207 is also axially coupled to the pitch frame 208, when the pitch frame 208 is pitch-rotated around the rotation shaft 246, the yaw frame 207 connected to the pitch frame 208, the first handle 204, the rotation shaft 241, the rotation shaft 242, and the rotation shaft 243 are pitch-rotated together. That is, when the pitch manipulation part 201 is rotated around the rotation shaft 246, the actuation manipulation part 203 and the yaw manipulation part 202 are rotated together with the pitch manipulation part 201. In other words, when a user pitch-rotates the first handle 204 around the rotation shaft 246, the actuation manipulation part 203, the yaw manipulation part 202, and the pitch manipulation part 201 are moved together.

The pulleys 217 and 218 and the pulleys 227 and 228 are coupled to the rotation shaft 246 so as to be rotatable around the rotation shaft 246 of the pitch frame 208.

Here, the pulley 217 and the pulley 218 may be formed to face each other so as to be independently rotatable. Accordingly, a wire being wound and a wire being released may be wound around respective separate pulleys so that the wires may perform motions without interference with each other. Similarly, the pulley 227 and the pulley 228 may also be formed to face each other so as to be independently rotatable. Accordingly, a wire being wound and a wire being released may be wound around respective separate pulleys so that the wires may perform motions without interference with each other.

Next, a motion of each of the wires 303 and 304, which are pitch wires, is described as follows.

The pulley 131, which is an end tool pitch pulley, is fixedly coupled to the end tool hub 180 in the end tool 100, and the pulley 231 and the pulley 232, which are manipulation part pitch pulleys, are fixedly coupled to the pitch frame 208 in the manipulation part 200. In addition, these pulleys are connected to each other by the wires 303 and 304, which are pitch wires, so that a pitch motion of the end tool 100 may be performed more easily according to the pitch manipulation of the manipulation part 200. Here, the wire 303 is fixedly coupled to the pitch frame 208 via the pulley 231 and the pulley 233, and the wire 304 is fixedly coupled to the pitch frame 208 via the pulley 232 and the pulley 234. That is, the pitch frame 208 and the pulleys 231 and 232 are rotated together around the rotation shaft 246 by the pitch rotation of the manipulation part 200, and as a result, the wires 303 and 304 are also moved, and thus, a driving force of additional pitch rotation may be transmitted separately from the pitch motion of the end tool by the wire 301, the wire 302, the wire 305, and the wire 306, which are jaw wires.

A connection relationship of each of the first handle 204, the pitch manipulation part 201, the yaw manipulation part 202, and the actuation manipulation part 203 is summarized as follows. The rotation shafts 241 and 242, the rotation shaft 243, the rotation shaft 244, the rotation shaft 245, and the rotation shaft 246 may be formed on the first handle 204. In this case, since the rotation shafts 241 and 242 are directly formed on the first handle 204, the first handle 204 and the actuation manipulation part 203 may be directly connected to each other. Meanwhile, since the rotation shaft 243 is directly formed on the first handle 204, the first handle 204 and the yaw manipulation part 202 may be directly connected to each other. On the other hand, since the pitch manipulation part 201 is formed on one side of the yaw manipulation part 202 so as to be connected to the yaw manipulation part 202, the pitch manipulation part 201 is not directly connected to the first handle 204, and the pitch manipulation part 201 and the first handle 204 may be formed to be indirectly connected to each other via the yaw manipulation part 202.

Continuing to refer to the drawings, in the surgical instrument 10 according to the first embodiment of the present disclosure, the pitch manipulation part 201 and the end tool 100 may be formed on the same or parallel axis (X-axis). That is, the rotation shaft 246 of the pitch manipulation part 201 is formed at one end portion of the bent part 402 of the connection part 400, and the end tool 100 is formed at the other end portion of the connection part 400.

In addition, one or more relay pulleys 235 configured to change or guide paths of the wires may be disposed at some places along the connection part 400, particularly in the bent part 402. As at least some of the wires are wound around the relay pulleys 235 to guide the paths of the wires, these wires may be disposed along a bent shape of the bent part 402.

Here, in the drawings, it is illustrated that the connection part 400 is formed to be curved with a predetermined curvature by having the bent part 402, but the concept of the present disclosure is not limited thereto, and the connection part 400 may be formed linearly or to be bent one or more times as necessary, and even in this case, it may be said that the pitch manipulation part 201 and the end tool 100 are formed on substantially the same axis or parallel axes. In addition, although FIG. 3 illustrates that each of the pitch manipulation part 201 and the end tool 100 is formed on an axis parallel to the X-axis, the concept of the present disclosure is not limited thereto, and the pitch manipulation part 201 and the end tool 100 may be formed on different axes.

(Actuation, Yaw, and Pitch Motions)

Actuation, yaw, and pitch motions in the present embodiment will be described as follows.

First, the actuation motion will be described below.

In a state in which a user inserts his/her index finger in the hand ring formed on the first actuation extension part 252 and his/her thumb in the hand ring formed on the second actuation extension part 257, when the user rotates the actuation rotation parts 252 and 257 using one or both of his/her index finger and thumb, the pulley 210 and the first actuation gear 253 fixedly coupled to the first actuation extension part 252 are rotated around the rotation shaft 241, and the pulley 220 and the second actuation gear 258 fixedly coupled to the second actuation extension part 257 are rotated around the rotation shaft 242. At this time, the pulley 210 and the pulley 220 are rotated in opposite directions, and thus the wires 301 and 305 fixedly coupled to the pulley 210 at one end portion thereof and the wires 302 and 306 fixedly coupled to the pulley 220 at one end portion thereof are also moved in opposite directions. In addition, a rotating force is transmitted to the end tool 100 through the power transmission part 300, and two jaws 103 of the end tool 100 perform an actuation motion.

Here, as described above, the actuation motion refers to a motion in which the two jaws 101 and 102 are splayed or closed while being rotated in opposite directions. That is, when the actuation rotation parts 252 and 257 of the actuation manipulation part 203 are rotated in directions close to each other, the first jaw 101 is rotated in the counterclockwise direction, and the second jaw 102 is rotated in the clockwise direction, thereby closing the end tool 100. That is, when the actuation rotation parts 252 and 257 of the actuation manipulation part 203 are rotated in directions away from each other, the first jaw 101 is rotated in the counterclockwise direction, and the second jaw 102 is rotated in the clockwise direction, thereby opening the end tool 100.

In the present embodiment, for the actuation manipulation described above, the first actuation extension part 252 and the second actuation extension part 257 are provided to configure the second handle and manipulated by gripping the second handle with two fingers. However, for the actuation manipulation in which the two jaws of the end tool 100 are opened or closed, the actuation manipulation part 203 may be configured in a manner different from the above-described manner, such as configuring the two actuation pulleys (the pulley 210 and the pulley 220) to act in opposition to each other with an actuation rotation part.

Next, the yaw motion will be described below.

When a user rotates the first handle 204 around the rotation shaft 243 while holding the first handle 204, the actuation manipulation part 203 and the yaw manipulation part 202 are yaw-rotated around the rotation shaft 243. That is, when the pulley 210 of the first actuation manipulation part 251 to which the wires 301 and 305 are fixedly coupled is rotated around the rotation shaft 243, the wires 301 and 305 wound around the pulleys 211 and 212 are moved. Similarly, when the pulley 220 of the second actuation manipulation part 256, to which the wires 302 and 306 are fixedly coupled, is rotated around the rotation shaft 243, the wires 302 and 306 wound around the pulleys 221 and 222 are moved. At this time, the wires 301 and 305 connected to the first jaw 101 and the wires 302 and 306 connected to the second jaw 102 are wound around the pulleys 211 and 212 and the pulleys 221 and 222, so that the first jaw 101 and the second jaw 102 are rotated in the same direction during yaw rotation. In addition, a rotating force is transmitted to the end tool 100 through the power transmission part 300, and thus a yaw motion in which two jaws 103 of the end tool 100 are rotated in the same direction is performed.

At this time, since the yaw frame 207 connects the first handle 204, the rotation shaft 241, the rotation shaft 242, and the rotation shaft 243, the first handle 204, the yaw manipulation part 202, and the actuation manipulation part 203 are rotated together around the rotation shaft 243.

Next, the pitch motion will be described below.

When a user rotates the first handle 204 around the rotation shaft 246 while holding the first handle 204, the actuation manipulation part 203, the yaw manipulation part 202, and the pitch manipulation part 201 are pitch-rotated around the rotation shaft 246. That is, when the pulley 210 of the first actuation manipulation part 251 to which the wires 301 and 305 are fixedly coupled is rotated around the rotation shaft 246, the wires 301 and 305 wound around the pulley 217 and the pulley 218 are moved. Similarly, when the pulley 220 of the second actuation manipulation part 256, to which the wires 302 and 306 are fixedly coupled, is rotated around the rotation shaft 246, the wires 302 and 306 wound around the pulley 227 and the pulley 228 are moved. At this time, as described with reference to FIG. 5, in order to allow the first jaw 101 and the second jaw 102 to pitch-rotate, the wires 301 and 305, which are first jaw wires, are moved in the same direction and respectively wound around the pulley 217 and the pulley 218, which are manipulation part pitch main pulleys, and the wires 302 and 306, which are second jaw wires, are moved in the same direction and respectively wound around the pulley 227 and the pulley 228, which are manipulation part pitch main pulleys. In addition, a rotating force is transmitted to the end tool 100 through the power transmission part 300, and two jaws 103 of the end tool 100 perform a pitch motion.

At this time, since the pitch frame 208 is connected to the yaw frame 207, and the yaw frame 207 connects the first handle 204, the rotation shaft 241, the rotation shaft 242, and the rotation shaft 243, when the pitch frame 208 is rotated around the rotation shaft 246, the yaw frame 207, the first handle 204, the rotation shaft 241, the rotation shaft 242, and the rotation shaft 243 connected to the pitch frame 208 are rotated together. That is, when the pitch manipulation part 201 is rotated around the rotation shaft 246, the actuation manipulation part 203 and the yaw manipulation part 202 are rotated together with the pitch manipulation part 201.

In summary, in the surgical instrument 10 according to an embodiment of the present disclosure, the pulleys are formed on respective joint points (an actuation joint, a yaw joint, and a pitch joint), the wires (the first jaw wire or the second jaw wire) are wound around the pulleys, the rotational manipulations (actuation rotation, yaw rotation, and pitch rotation) of the manipulation part cause the movement of each wire, which in turn induces the desired motion of the end tool 100. Furthermore, the auxiliary pulley may be formed on one side of each of the pulleys, and the wire may not be wound several times around one pulley due to the auxiliary pulley.

FIG. 11 is a view schematically illustrating only a configuration of pulleys and wires constituting joints of the surgical instrument 10 according to an embodiment of the present disclosure illustrated in FIG. 2. In FIG. 11, the relay pulleys for changing paths of the wires and not related to the operation of joints are omitted.

Referring to FIG. 11, the manipulation part 200 may include the pulley 210, the pulley 211, the pulley 212, the pulley 213, the pulley 214, the pulley 215, the pulley 216, the pulley 217, and the pulley 218 that are related to a rotational motion of the first jaw 101.

In addition, the manipulation part 200 may include the pulley 220, the pulley 221, the pulley 222, the pulley 223, the pulley 224, the pulley 225, the pulley 226, the pulley 227, and the pulley 228 that are related to a rotational motion of the second jaw 102 (the arrangement and structure of each of the pulleys of the manipulation part 200 are the same in principle as the arrangement and structure of each of the pulleys of the end tool 100, and thus specific designations of some reference numerals are omitted in the drawings).

The pulleys 211 and 212 and the pulleys 221 and 222 may be formed to be rotatable independently of each other around the same shaft, that is the rotation shaft 243. In this case, the pulleys 211 and 212 and the pulleys 221 and 222 may each be formed as two pulleys formed to face each other and formed to be independently rotatable.

The pulleys 213 and 214 and the pulleys 223 and 224 may be formed to be rotatable independently of each other around the same shaft, that is the rotation shaft 244. Here, the pulleys 213 and 214 may be formed as two pulleys formed to face each other and formed to be independently rotatable, and in this case, the two pulleys may be formed to have different diameters. Similarly, the pulleys 223 and 224 may be formed as two pulleys formed to face each other and formed to be independently rotatable, and in this case, the two pulleys may be formed to have different diameters.

The pulleys 215 and 216 and the pulleys 225 and 226 may be formed to be rotatable independently of each other around the same shaft, that is the rotation shaft 245. In this case, the pulleys 215 and 216 may be formed to have different diameters. In addition, the pulleys 225 and 226 may be formed to have different diameters.

The pulleys 217 and 218 and the pulleys 227 and 228 may be formed to be rotatable independently of each other around the same shaft, that is the rotation shaft 246.

The wire 301 is wound around the pulley 210 after sequentially passing through the pulley 217, the pulley 215, the pulley 213, and the pulley 211 of the manipulation part 200, and then is coupled to the pulley 210 by the coupling member 324. Meanwhile, the wire 305 sequentially passes through the pulley 218, the pulley 216, the pulley 214, and the pulley 212 of the manipulation part 200 and is coupled to the pulley 210 by the coupling member 324. Thus, when the pulley 210 is rotated, the wires 301 and 305 are wound around or released from the pulley 210, and accordingly, the first jaw 101 is rotated.

The wire 306 is wound around the pulley 220 after sequentially passing through the pulley 227, the pulley 225, the pulley 223, and the pulley 221 of the manipulation part 200, and then is coupled to the pulley 220 by the coupling member 327. Meanwhile, the wire 302 sequentially passes through the pulley 228, the pulley 226, the pulley 224, and the pulley 222 of the manipulation part 200 and is coupled to the pulley 220 by the coupling member 327. Thus, when the pulley 220 is rotated, the wire 302 and the wire 306 are wound around or released from the pulley 220, and accordingly, the second jaw 102 is rotated.

Thus, the actuation, yaw, and pitch manipulations are manipulatable independent of each other.

As described with reference to FIG. 1, the actuation manipulation part 203, the yaw manipulation part 202, and the pitch manipulation part 201 are configured such that the respective rotation shafts are located at the rear thereof to be identical to the joint configuration of the end tool, so that a user may intuitively perform matching manipulations.

In particular, in the surgical instrument 10 according to an embodiment of the present disclosure, the pulleys are formed on respective joint points (an actuation joint, a yaw joint, and a pitch joint), the wires (the first jaw wire or the second jaw wire) are formed to be wound around the pulleys, the rotational manipulations (actuation rotation, yaw rotation, and pitch rotation) of the manipulation part cause the movement of each wire, which in turn induces the desired motion of the end tool 100. Furthermore, the auxiliary pulleys may be formed on one side of the respective pulleys, and these auxiliary pulleys may prevent the wire from being wound on one pulley multiple times, so that the wires wound on the pulley do not come into contact with each other, and paths of the wire being wound around the pulley and the wire being released from the pulley are safely formed, so that safety and efficiency in the transmission of driving force of a wire may be improved.

Meanwhile, as described above, the yaw manipulation part 202 and the actuation manipulation part 203 are directly formed on the first handle 204. Thus, when the first handle 204 is rotated around the rotation shaft 246, the yaw manipulation part 202 and the actuation manipulation part 203 are also rotated together with the first handle 204. Accordingly, the coordinate systems of the yaw manipulation part 202 and the actuation manipulation part 203 are not fixed, but are continuously changed relative to the rotation of the first handle 204. That is, in FIG. 2 or the like, the yaw manipulation part 202 and the actuation manipulation part 203 are illustrated as being parallel to the z-axis. However, when the first handle 204 is rotated, the yaw manipulation part 202 and the actuation manipulation part 203 are not parallel to the Z-axis any longer. That is, the coordinate systems of the yaw manipulation part 202 and the actuation manipulation part 203 are changed according to the rotation of the first handle 204. However, in the present specification, for convenience of description, unless described otherwise, the coordinate systems of the yaw manipulation part 202 and the actuation manipulation part 203 are described on the basis of a state in which the first handle 204 is located perpendicular to the connection part 400 as illustrated in FIG. 2.

(Locking Device)

Hereinafter, locking devices 260 and 270 of the surgical instrument 10 according to one embodiment of the present disclosure will be described in more detail.

Figure 12:
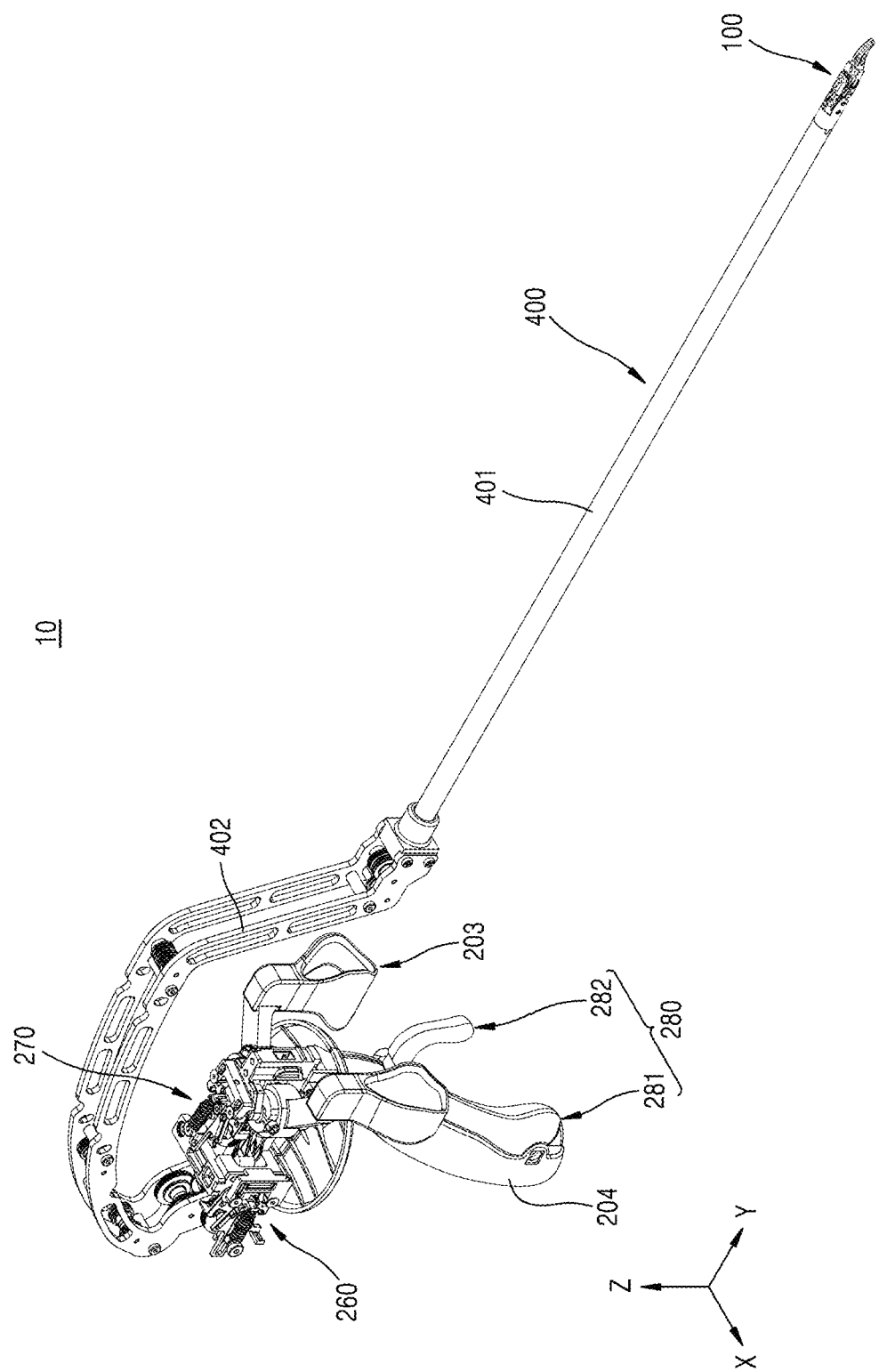
FIG. 12 is a perspective view illustrating a locked state of the surgical instrument illustrated in FIG. 2.
Figure 13:
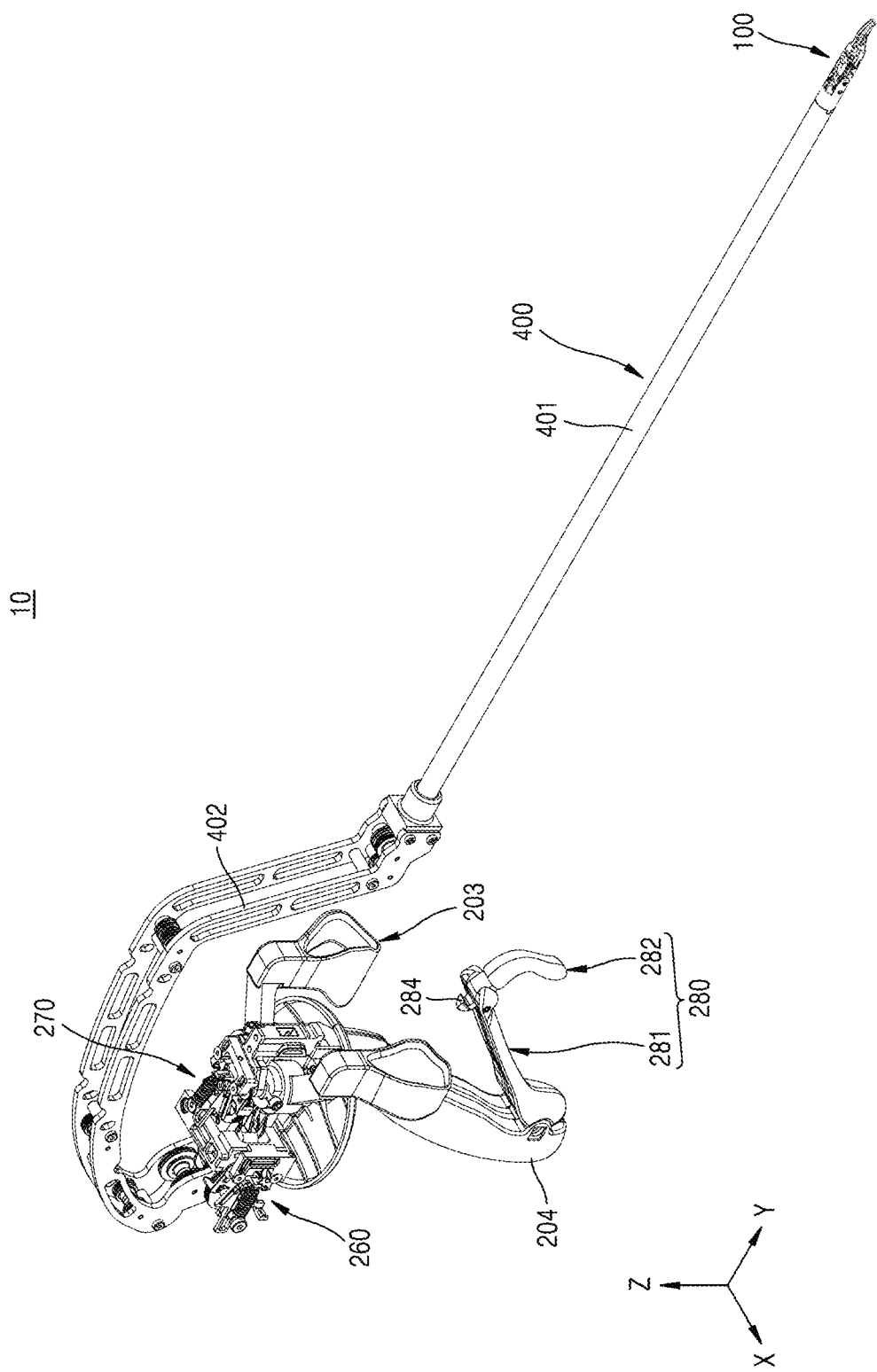
FIG. 13 is a perspective view illustrating an unlocked state of the surgical instrument illustrated in FIG. 2.
Figure 14:
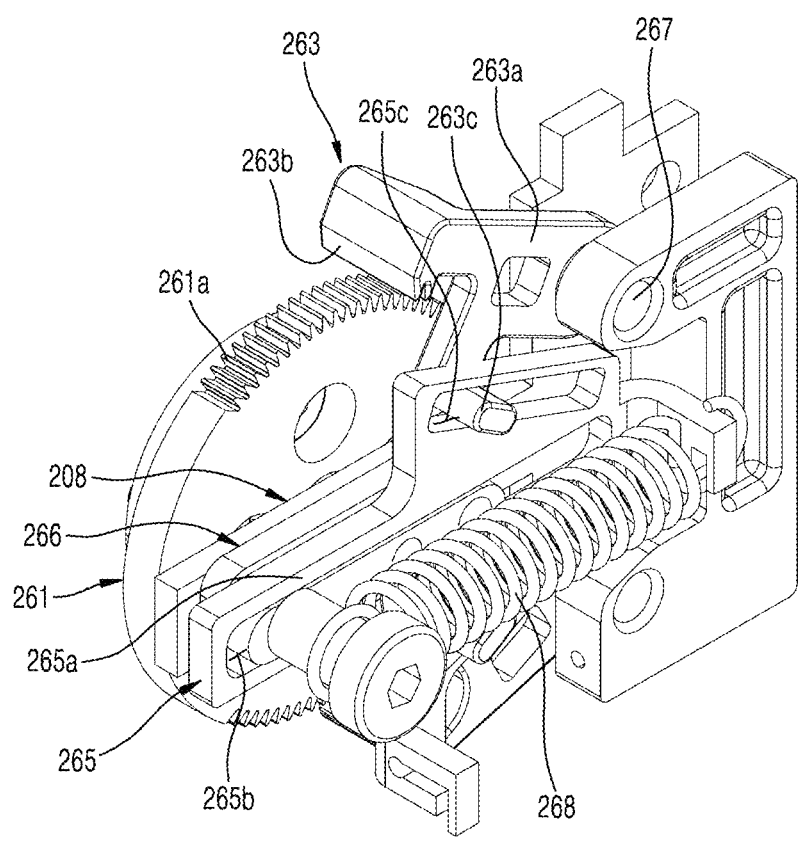
FIG. 14 is an assembled perspective view illustrating a locking device of the surgical instrument illustrated in FIG. 12.
Figure 15:
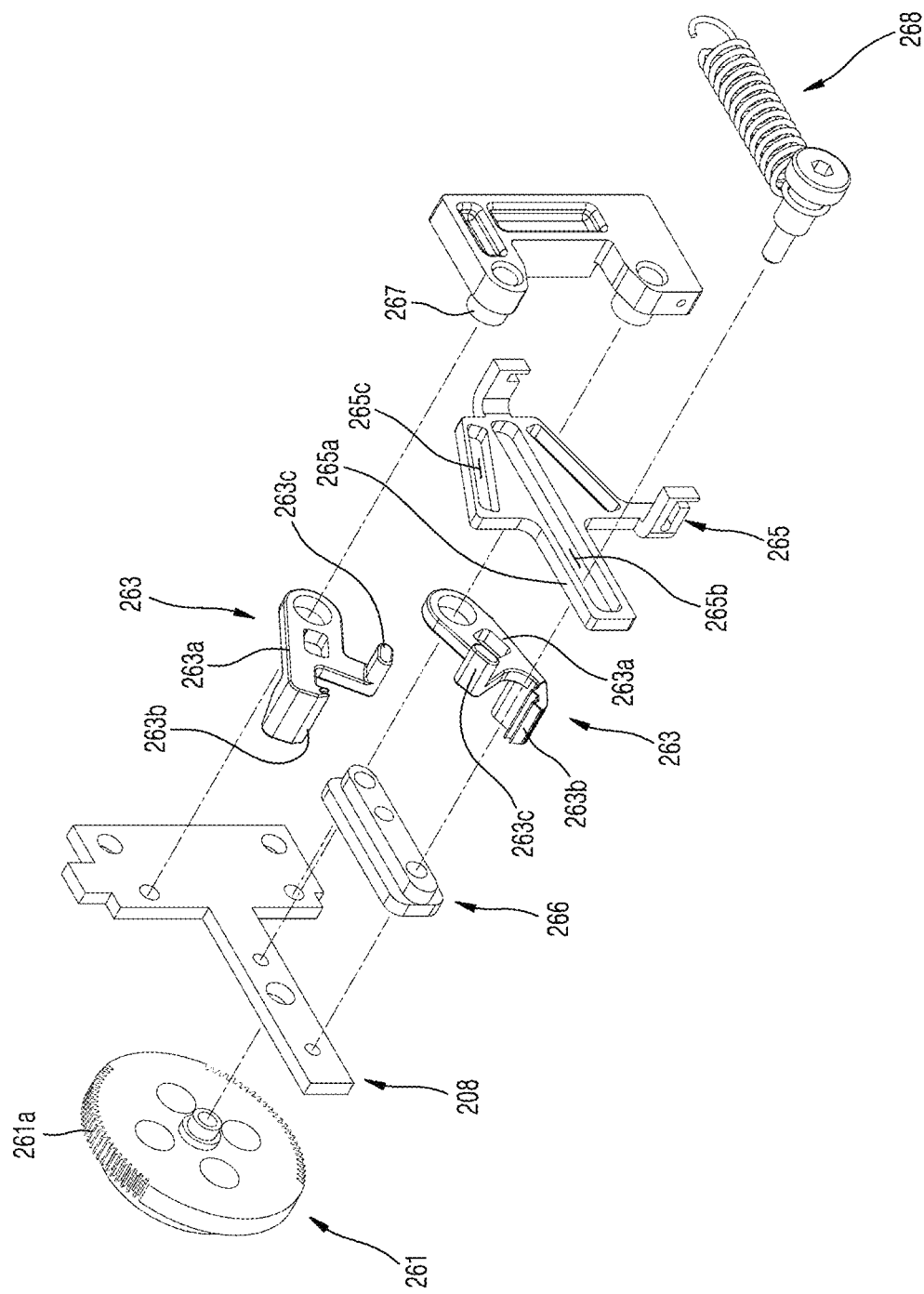
FIG. 15 is an exploded perspective view illustrating the locking device of the surgical instrument illustrated in FIG. 12.
Figure 16:
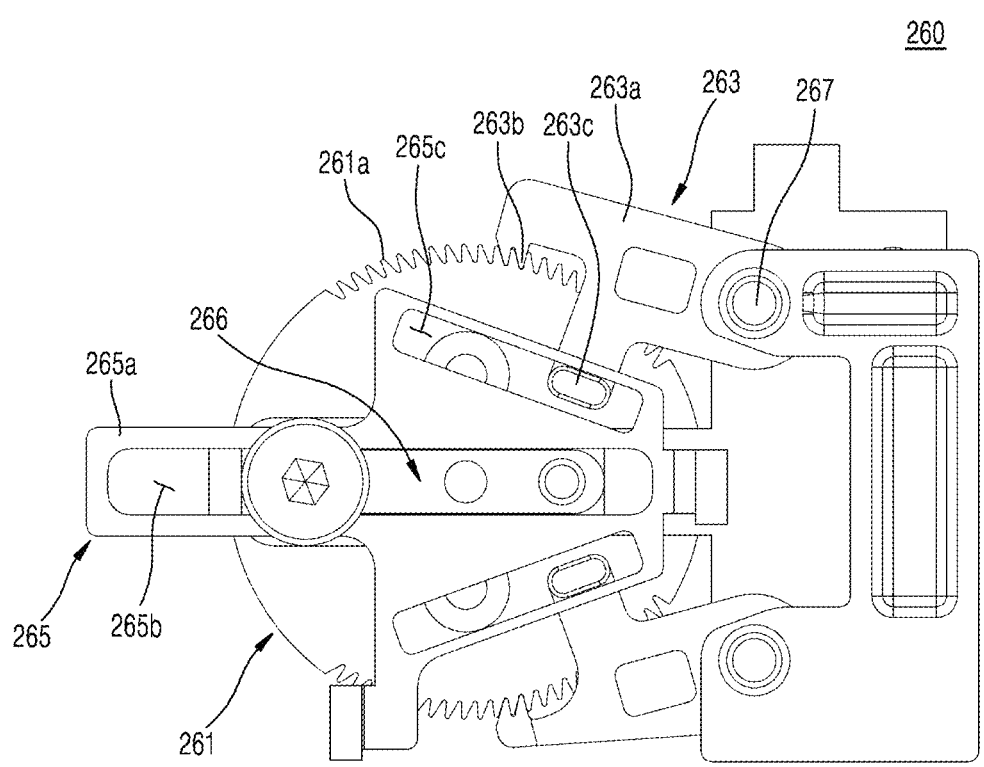
FIGS. 16 and 17 are plan views illustrating a locked state of the locking device of the surgical instrument of FIG. 14.
Figure 17:
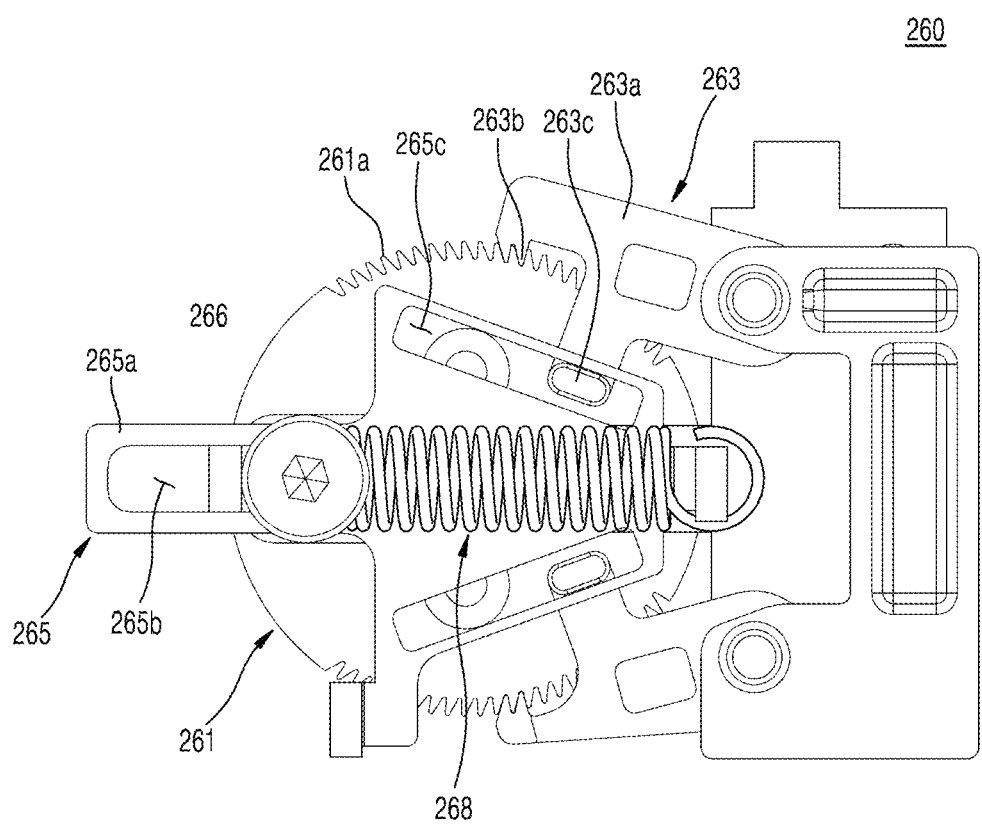
Figure 18:
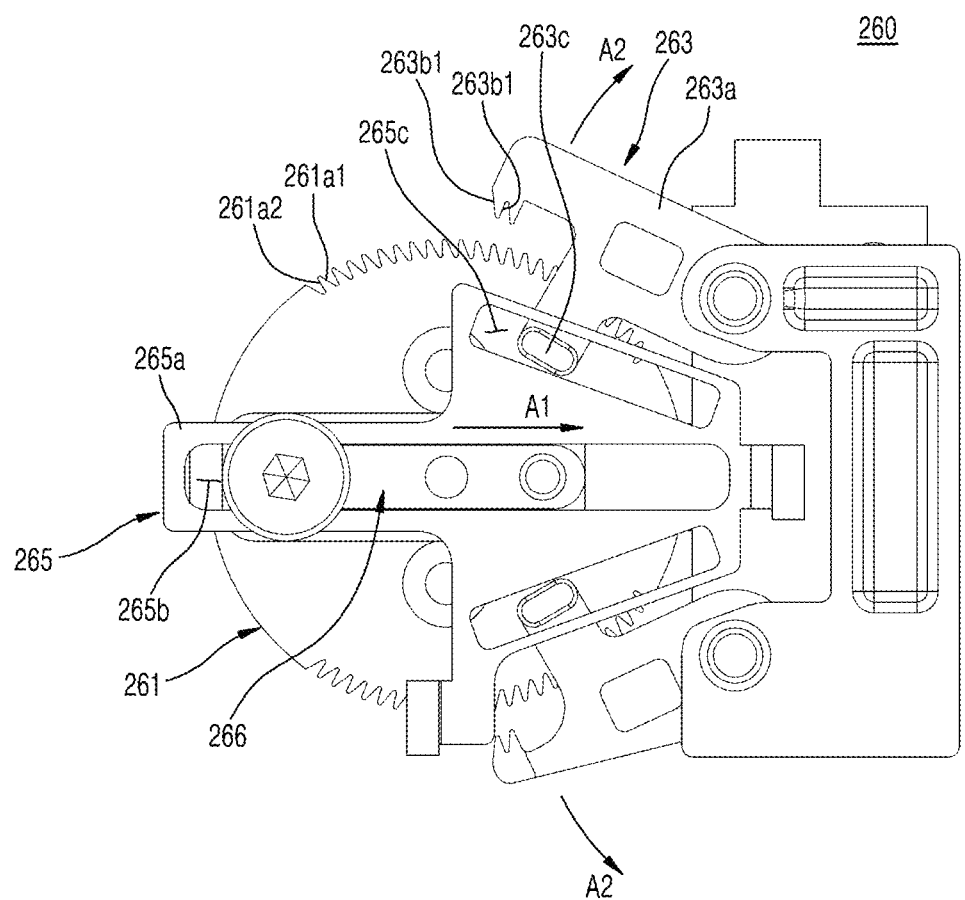
FIGS. 18 and 19 are plan views illustrating an unlocked state of the locking device of the surgical instrument of FIG. 14.
Figure 19:
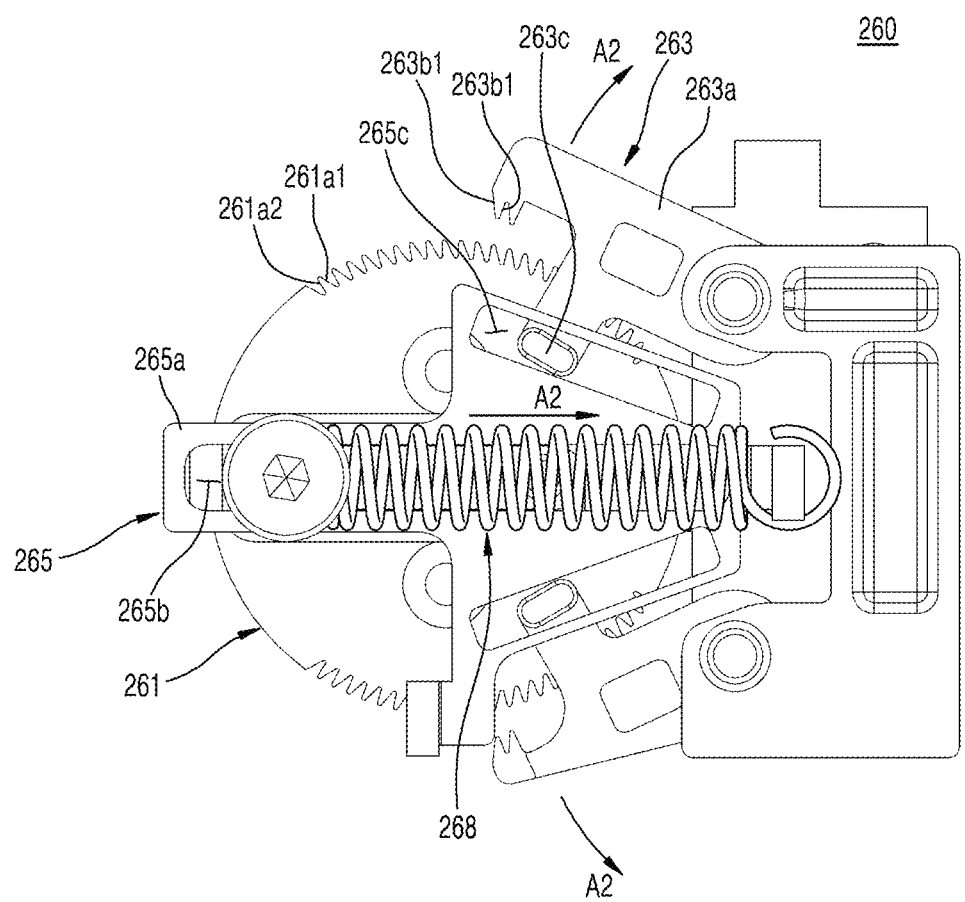
Figure 20:
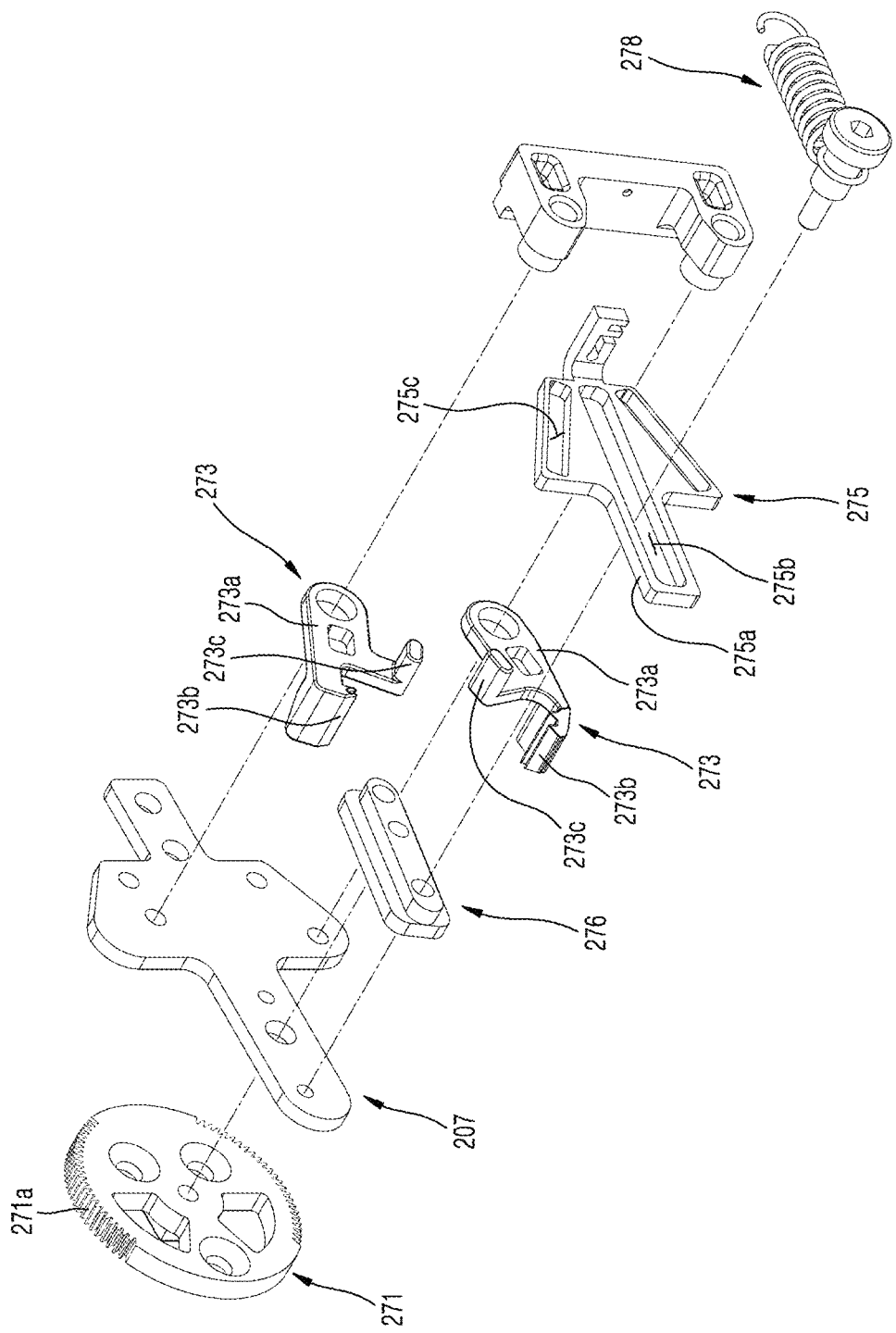
FIG. 20 is an exploded perspective view illustrating the locking device of the surgical instrument illustrated in FIG. 2.
Figure 21:
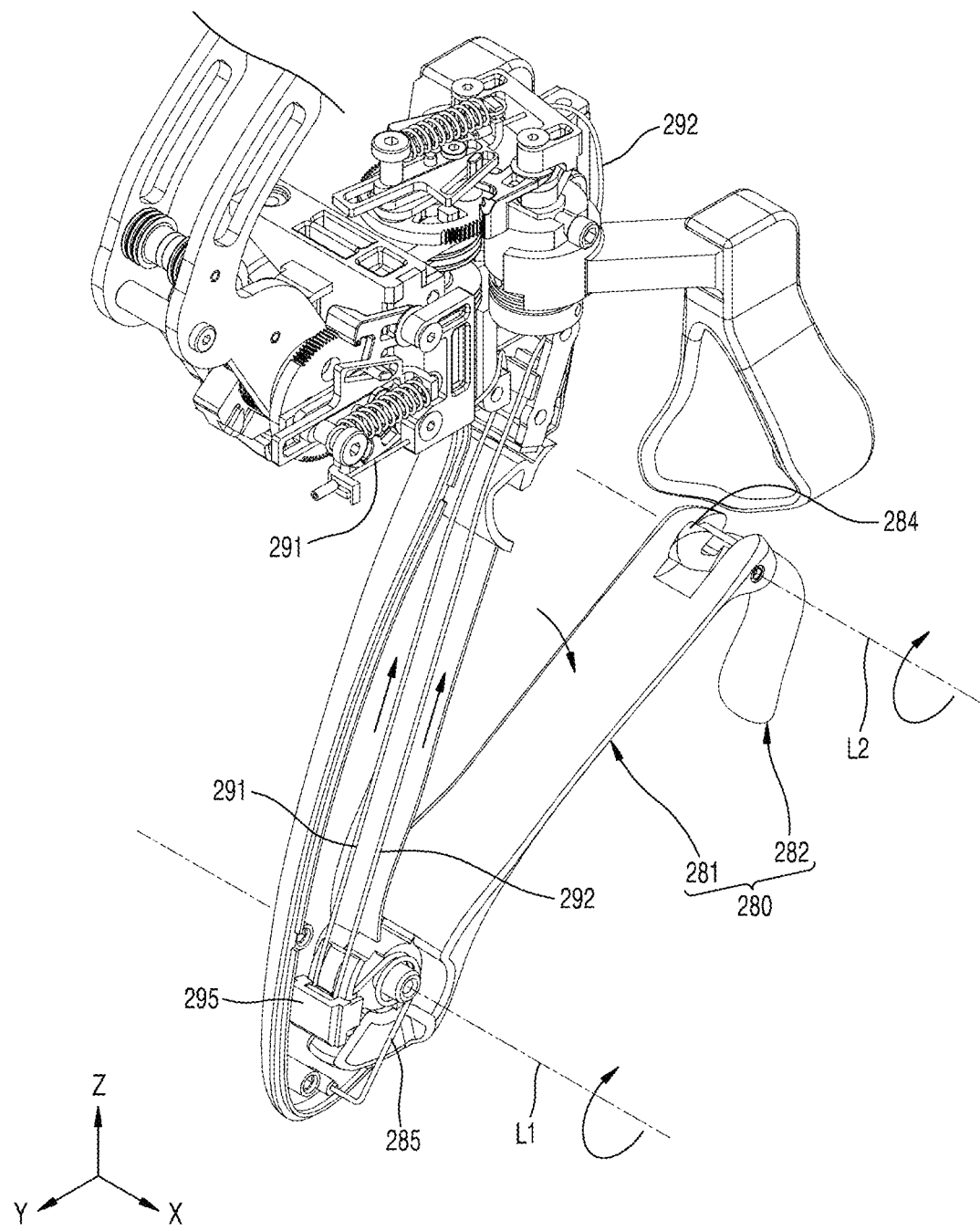
FIG. 21 is a perspective view illustrating a locked state of a lever part of the surgical instrument illustrated in FIG. 2.
Figure 22:
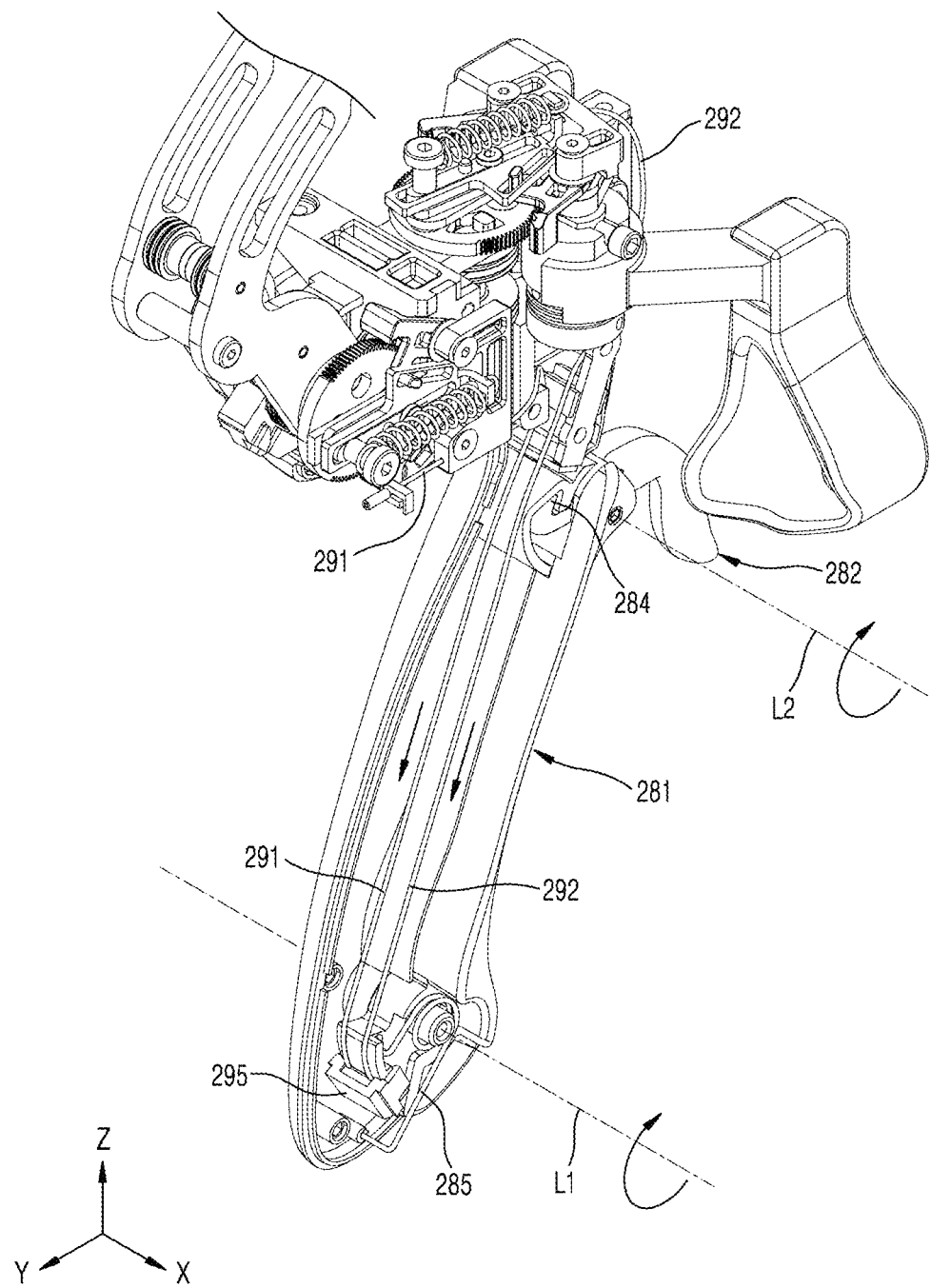
FIG. 22 is a perspective view illustrating an unlocked state of the lever part of the surgical instrument illustrated in FIG. 2.
Figure 23:
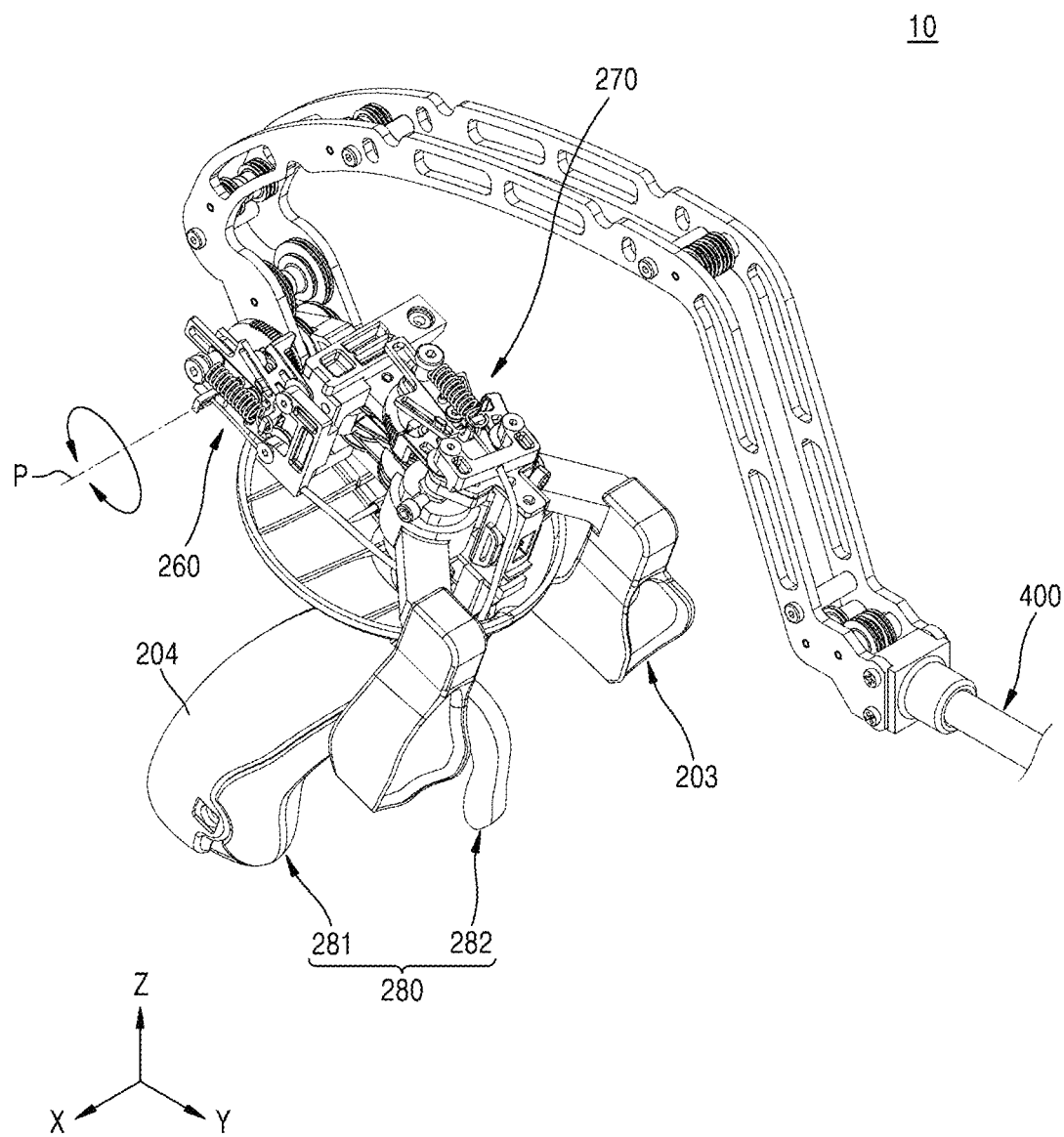
FIGS. 23 and 24 are perspective views illustrating a pitch motion of the surgical instrument illustrated in FIG. 2.
Figure 24:
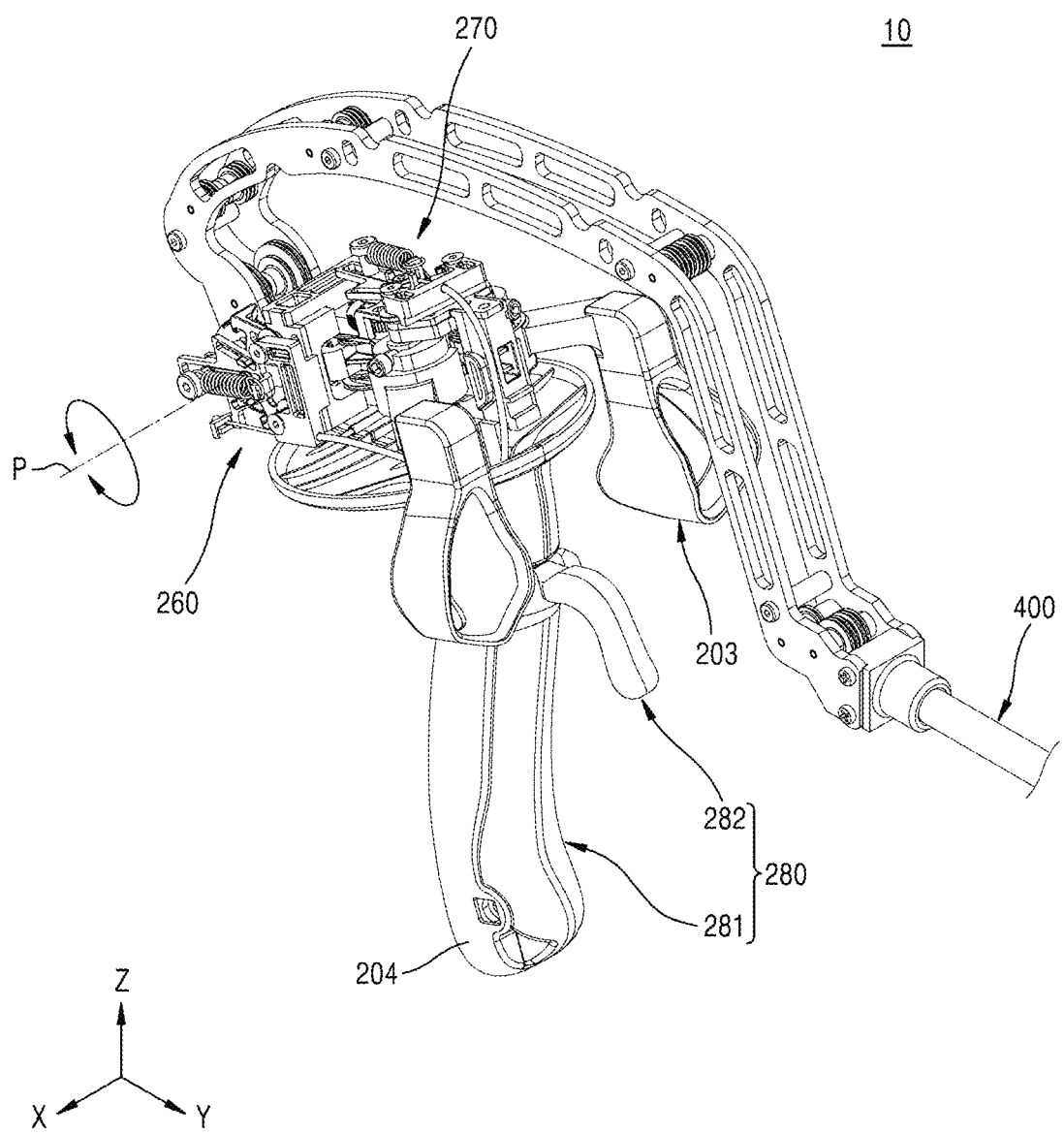
Figure 25:
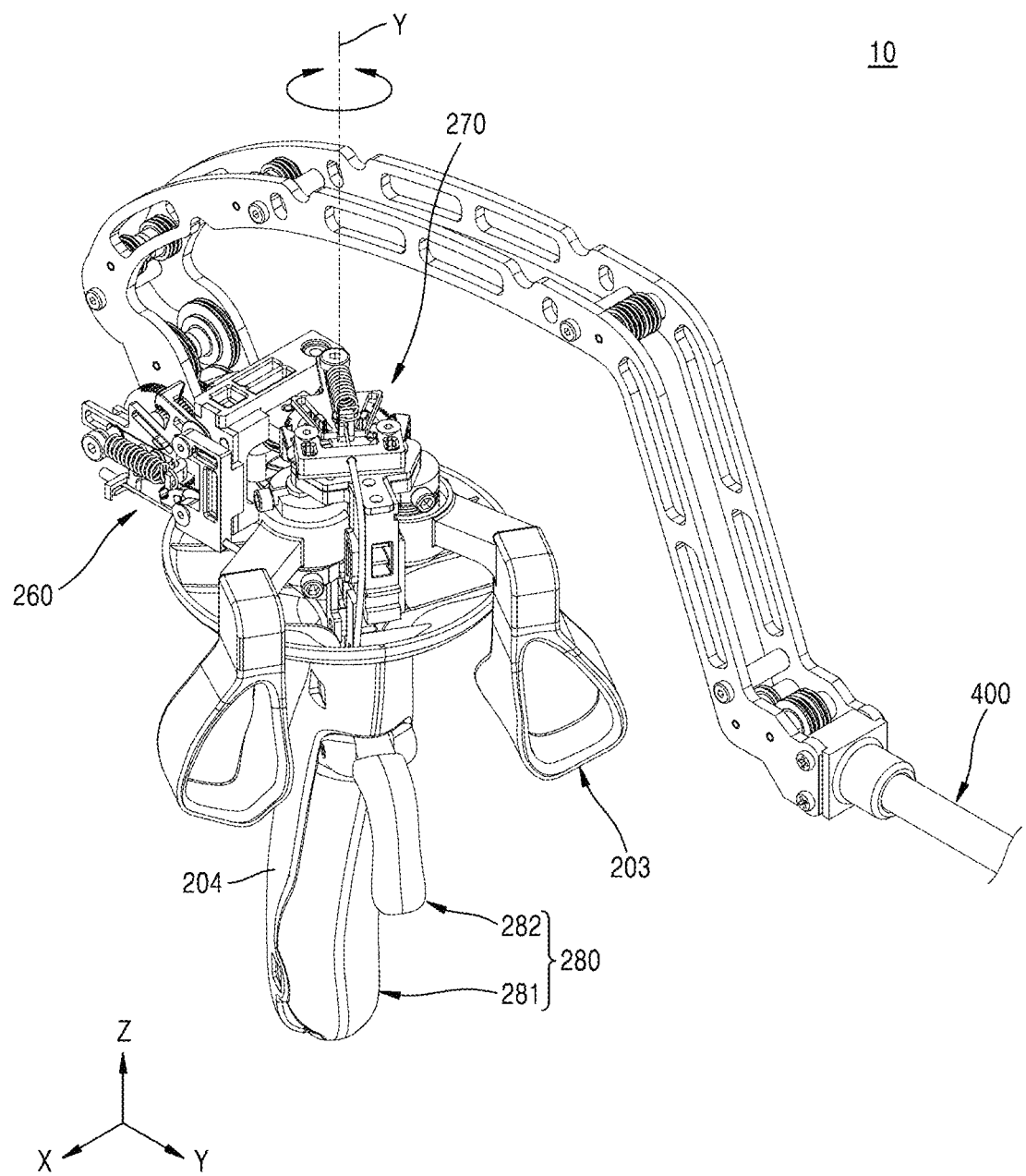
FIGS. 25 and 26 are perspective views illustrating a yaw motion of the surgical instrument illustrated in FIG. 2.
Figure 26:
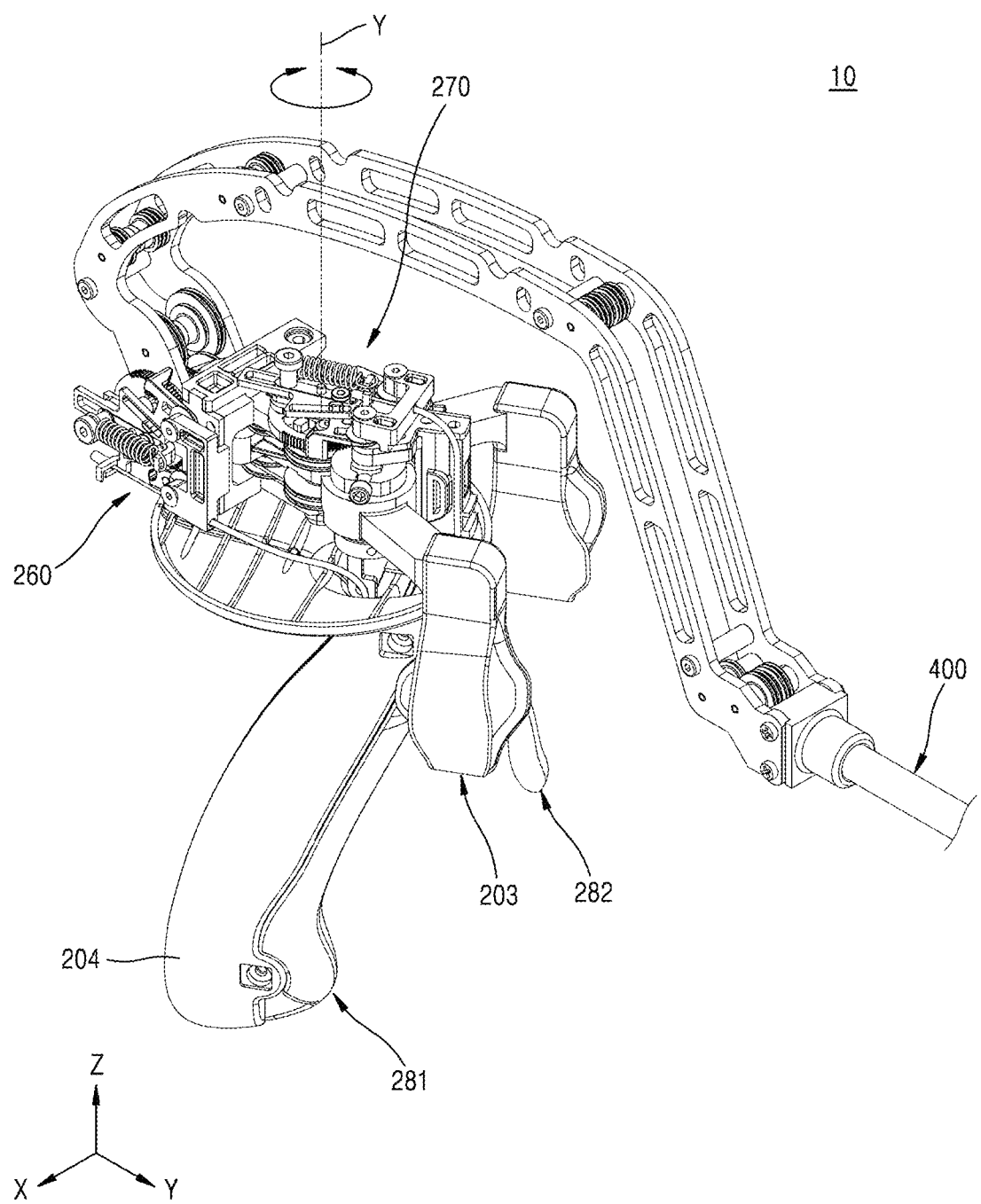

FIG. 12 is a perspective view illustrating a locked state of the surgical instrument illustrated in FIG. 2, and FIG. 13 is a perspective view illustrating an unlocked state of the surgical instrument illustrated in FIG. 2. FIG. 14 is an assembled perspective view illustrating the locking device of the surgical instrument illustrated in FIG. 12, and FIG. 15 is an exploded perspective view illustrating the locking device of the surgical instrument illustrated in FIG. 12. FIGS. 16 and 17 are plan views illustrating the locked state of the locking device of the surgical instrument illustrated in FIG. 14. FIGS. 18 and 19 are plan views illustrating the unlocked state of the locking device of the surgical instrument illustrated in FIG. 14. Here, FIGS. 16 and 18 are views from which an elastic member is omitted. FIG. 20 is an exploded perspective view illustrating the locking device of the surgical instrument illustrated in FIG. 2. FIG. 21 is a perspective view illustrating a locked state of a lever part of the surgical instrument illustrated in FIG. 2, and FIG. 22 is a perspective view illustrating an unlocked state of the lever part of the surgical instrument illustrated in FIG. 2. Here, for convenience of explanation, some components are omitted in some drawings.

Referring to FIGS. 12 through 22, the surgical instrument 10 according to one embodiment of the present disclosure includes a locking device 260 that is configured to lock/unlock a pitch motion, and a locking device 270 that is configured to lock/unlock a yaw motion. In the present disclosure, the user may control the locking devices 260 and 270 through a locking manipulation part 280 to control relative motion among the connection part 400, the pitch manipulation part 201, the yaw manipulation part 202.

As described above, in the present disclosure, the pitch motion of the manipulation part 200 refers to a relative rotation of the pitch manipulation part 201 with respect to the connection part 400, more specifically, a relative rotational motion of the yaw frame 207 with respect to the bent part 402. Here, the pitch manipulation part 201 including the yaw frame 207, the yaw manipulation part 202 connected to the yaw frame 207, the actuation manipulation part 203, and the first handle 204 perform the pitch motion while rotating around the rotation shaft 246. Here, when the movement of the pitch manipulation part 201 is restricted by the locking member 270, the pitch motion of the end tool (see 100 in FIG. 2, etc.) is also restricted.

Also, as described above, in the present disclosure, the yaw motion of the manipulation part 200 refers to a relative rotation of the yaw manipulation part 202 with respect to the pitch manipulation part 201, more specifically, a relative rotational motion of the yaw frame 207 with respect to the yaw frame 207. Here, the yaw manipulation part 202 including the yaw frame 207, the first handle 204 coupled to the yaw frame 207, the actuation manipulation part 203 perform a yaw motion while rotating around the rotation shaft 243. Here, when the movement of the yaw manipulation part 202 is restricted by the locking member 260, the yaw motion of the end tool (see 100 in FIG. 2, etc.) is also restricted.

Hereinafter, the locking device 260, which is responsible for locking/unlocking the pitch motion, will be described in more detail.

The locking device 260 may include a locking body part 261, a locking part 263, and a locking control part 265. The locking device 260 serves to lock or unlock the pitch motion of the pitch manipulation part 202.

First, although not illustrated in detail in the drawings, the locking body part 261 may be fixedly coupled to the bent part 402 of the connection part 400. Accordingly, the locking body part 261 may be rotatable together with the bent part 402 of the connection part 400.

One end portion of the bent part 402 and the locking body part 261 are axially coupled to the yaw frame 207 by the rotation shaft 246. Thus, the yaw frame 207 is rotatable relative to the bent part 402 (and the locking body part 261).

Meanwhile, the locking part 263 may be coupled to the yaw frame 207.

In other words, the locking body part 261 is fixedly coupled to the bent part 402 of the connection part 400, and the locking part 263 is coupled to the yaw frame 207. Accordingly, when the locking part 263 is coupled to the locking body part 261, the yaw frame 207 is locked not to be rotatable relative to the bent part 402 and the locking body part 261. On the other hand, when the locking part 263 is spaced apart from the locking body part 261, the yaw frame 207 is unlocked to be rotatable relative to the bent part 402 and the locking body part 261. This will be explained in more detail as follows.

In detail, the locking body part 261 is fixedly coupled to the bent part 402 of the connection part 400. Here, the locking body part 261 may be formed substantially in the form of a disk, and have a plurality of first coupling parts 261a formed in a gear shape on an outer circumferential surface thereof. Therefore, the locking body part 261 may be formed as a whole in a gear shape. The locking body part 261 is fixedly coupled to one end portion of the bent part 402 of the connection part 400. Accordingly, when the rotation of the locking body part 261 is restricted by the locking part 263 and the locking control part 265, the rotation of the connection part 400 fixedly coupled to the locking body part 261 is restricted, thereby locking the pitch motion.

The locking part 263 is coupled to the yaw frame 207. In detail, the locking part 263 is axially coupled to be rotatable with respect to the yaw frame 207. Here, the locking part 263 is formed to be spaced apart from and/or coupled to the first coupling part 261a of the locking body part 261. The locking part 263 may include a body part 263a formed in the shape of a bar to be rotatable around a locking rotation shaft 267 that is fixedly coupled to the yaw frame 207, a second coupling part 263b formed on one end portion of the body part 263a and engaged with the first coupling part 261a, and a contact part 263c brought into contact with the locking control part 265 to be explained later.

Here, the second coupling part 263b may be formed in the shape of a hook so as to be engaged with at least one of the gear of the first coupling part 261a.

Here, the second coupling part 263b may include a first surface 263b1 and a second surface 263b2. The first surface 263b1 may be formed to have a predetermined angle and a gentle inclination, and the second surface 263b2 may be formed vertically or almost vertically. Likewise, the first coupling part 261a of the locking body part 261 may include a first surface 261a1 and a second surface 261a2. The first surface 261a1 may be formed to have a predetermined angle and a gentle inclination, and the second surface 261a2 may be formed vertically or almost vertically. In this case, the inclined first surface 263b1 of the second coupling part 263b and the inclined first surface 261a1 of the first coupling part 261a may be disposed to face each other (that is, to be in contact with each other).

The locking control part 265 is formed to be movable relative to the locking body part 261 and the locking part 263, to control whether the locking body part 261 and the locking part 263 are coupled to/spaced apart from each other depending its position.

The locking control part 265 may include a body part 265a, a guide part 265b, and a pressing part 265c. In detail, the body part 265a of the locking control part 265 may be formed in the shape of a bar to perform a reciprocating linear motion with respect to the locking body part 261. The guide part 265b may be formed in the body part 265a of the locking control part 265 to guide a movement path of the locking control part 265a. The guide part 265b may be formed in the shape of an elongated hole, and one or more guide pins 266 fixedly coupled to the yaw frame 207 may be inserted into the guide part 265b. Accordingly, the locking control part 265 may perform a reciprocating linear motion with respect to the locking body part 261 by virtue of the guide part 265b and the guide pins 266. Here, the drawings illustrate that the guide part 265b is formed in the shape of a hole and the guide pin 266 is formed in the shape of a pin, but the concept of the present disclosure is not limited thereto. The guide part may alternatively be formed in various shapes to guide the linear motion of the locking control part 265, for example, a protrusion may be formed on the locking control part 265 and a guide groove may be formed in the locking body part 261 or the yaw frame 207.

The pressing part 265c may protrude to a certain extent from both surfaces of the locking control part 265 to be in contact with the contact part 263c of the locking part 263. Here, the pressing part 265c is formed to gradually protrude toward the distal end 205 of the manipulation part 200, and thus may be formed substantially in an arrow shape.

Figure 27:
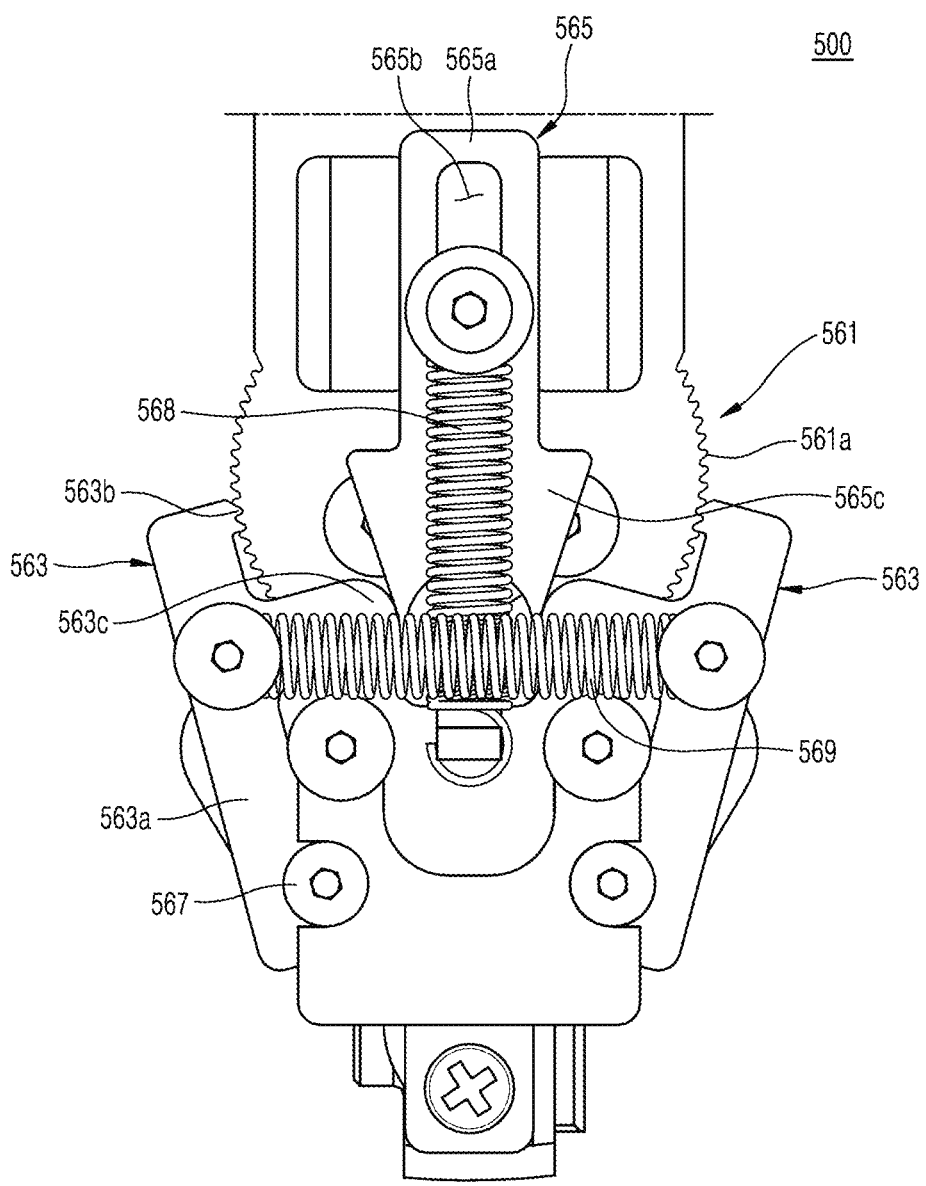
FIG. 27 is a plan view illustrating a locked state of a locking device according to another embodiment of the present disclosure.
Figure 28:
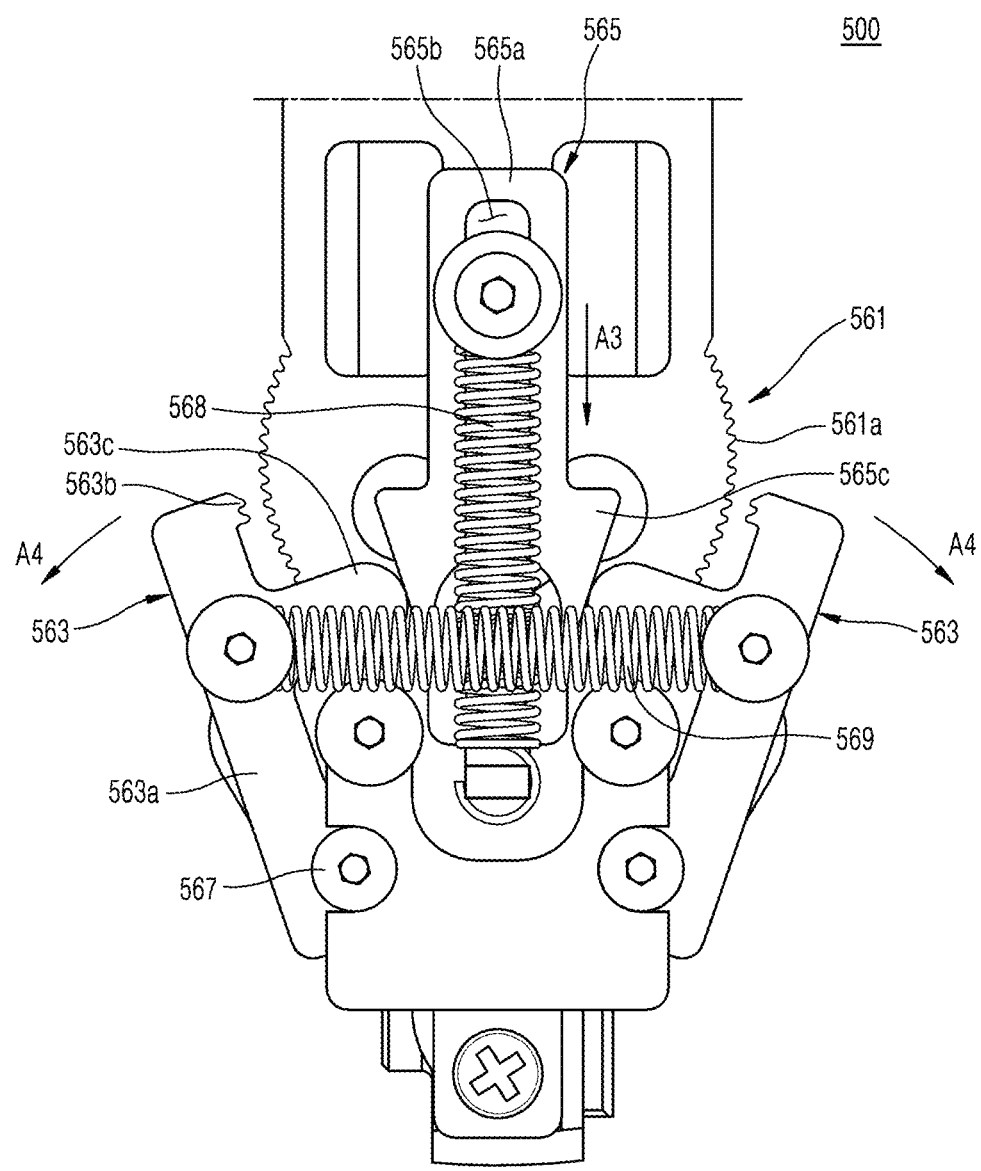
FIG. 28 is a plan view illustrating an unlocked state of the locking device according to another embodiment of the present disclosure.

In the drawings, the pressing part 265c is formed in the shape of a hole, and the contact part 263c of the locking part 263 is inserted into the hole-shaped pressing part 265c, so that the contact part 263c is pressed by an inner edge surface of the pressing part 265c. However, the concept of the present disclosure is not limited thereto. Alternatively, as illustrated in FIGS. 27 and 28, the pressing part (see 565c in FIG. 27) may protrude as a whole from the body part (see 565a in FIG. 27), and the contact part (see 563c in FIG. 27) may be pressed by an outer peripheral surface of the pressing part (565c in FIG. 27).

Regardless of the shape, the pressing part 265c may be formed to be inclined by a certain degree with respect to the guide pin 266 or the guide part 265b, which is a central axis of movement. In other words, it may also be expressed that a width becomes thicker in one direction along the guide pin 266. In other words, in view of one direction as a moving direction of the locking control part 265, it may also be said that the width of the locking control part increases along the one direction. Accordingly, when the locking control part 265 moves in any one direction, the pressing part 265c of the locking control part 265 may press the contact part 263c of the locking part 263, such that the locking part 263 is spaced apart from the locking body part 261.

In other words, in the state illustrated in FIG. 16, as the locking control part 265 moves in a direction of an arrow A1 of FIG. 18, the locking control part 265 may push the contact part 263c of the locking part 263, such that the locking part 263 rotates in a direction of an arrow A2 of FIG. 18. And, as the locking part 263 rotates in the direction of the arrow A2, the second coupling part 263b of the locking part 263 may be spaced apart from the first coupling part 261a of the locking body part 261, such that the locking part 263 is unlocked.

In contrary, in the state illustrated in FIG. 18, when the locking control part 265 moves in an opposite direction to the arrow A1 of FIG. 18, the locking part 263 may rotate in an opposite direction to the arrow A2 of FIG. 18. And, as the locking part 263 rotates in the opposite direction of the arrow A2, the second coupling part 263b of the locking part 263 may be coupled to be in contact with the first coupling part 261a of the locking body part 261, such that the locking part 263 is locked.

Here, since the locking control part 265 is coupled to a first locking wire 291, which will be described later, the locking control part 265 may be moved in any one direction as the first locking wire 291 is moved by rotation of a first locking lever part 281.

Meanwhile, an elastic member 268 may be further disposed between the locking part 263 and the locking control part 265. For example, the elastic member 268 may be formed in the form of a coil spring. One side of the elastic member 268 may be coupled to the locking control part 265 side and the other side may be fixedly coupled to the yaw frame 207 side. In this instance, the elastic member 268 may be configured as a tension spring, and may apply a predetermined elastic force so that the locking control part 265 moves in the direction opposite to the arrow A1 of FIG. 18.

Therefore, if there is no intervention by another member, the locking control part 265 is basically positioned, as illustrated in FIG. 16, by the elastic force applied by the elastic member 268. This state is a state in which the locking control part 265 applies the minimum force to the locking part 263. In this state, the locking body part 261 and the locking part 263 are coupled to each other, thus to be in a locked state. In other words, it may be seen that the locking part 263 is basically receiving force from the elastic member 268 to be in the locked state.

Meanwhile, when the first locking wire 291 pulls the locking control part 265 in the direction of the arrow A1 of FIG. 18 as the locking manipulation part 280 to be explained later is operated, the locking member 260 is in the state as illustrated in FIG. 18. In this state, the locking control part 265 pushes the locking part 263 as much as possible, so that the locking part 263 is spaced apart as much as possible from the locking body part 261. In this state, since the locking body part 261 and the locking part 263 are not in contact with/coupled to each other, the locking device 260 is in the unlocked state.

Meanwhile, even in this state, the elastic member 268 is applying elastic force in the direction opposite to the arrow A1, and therefore, when force pulling the first locking wire 291 is released, the locking control part 265 returns to the position of FIG. 16 by the elastic force. Accordingly, the locking device 260 is switched back to the locked state.

Hereinafter, the locking device 270, which is responsible for locking/unlocking the yaw motion, will be described in more detail.

The locking device 270 may include a locking body part 271, a locking part 273, and a locking control part 275. The locking device 270 serves to lock or unlock the yaw motion of the yaw manipulation part 202.

First, although not illustrated in detail in the drawings, the locking body part 271 may be fixedly coupled to a pitch frame 208. Accordingly, the locking body part 271 may be rotatable together with the pitch frame 208.

The locking body part 271 is axially coupled to the yaw frame 207 by the rotation shaft 243. Thus, the yaw frame 207 is rotatable relative to the pitch frame 208.

Meanwhile, the locking part 273 may be coupled to the yaw frame 207.

In other words, the locking body part 271 is fixedly coupled to the pitch frame 208, and the locking part 273 is coupled to the yaw frame 207. Accordingly, when the locking part 273 is coupled to the locking body part 271, the yaw frame 207 is not rotatable relative to the pitch frame 208, so as to be in the locked state. On the other hand, when the locking part 273 is spaced apart from the locking body part 261, the yaw frame 207 is rotatable relative to the pitch frame 208 so as to be in an unlocked state. This will be explained in more detail as follows.

In detail, the locking body part 271 is fixedly coupled to the pitch frame 208. Here, the locking body part 271 may be formed substantially in the form of a disk, and have a plurality of first coupling part 271a formed in a gear shape on an outer circumferential surface thereof. Therefore, the locking body part 261 may be formed as a whole in a gear shape. The locking body part 271 is fixedly coupled to the pitch frame 208. Accordingly, when the rotation of the locking body part 271 is restricted by the locking part 273 and the locking control part 275, the rotation of the pitch frame 208 fixedly coupled to the locking body part 271 is restricted, thereby locking the yaw motion.

The locking part 273 is coupled to the yaw frame 207. In detail, the locking part 273 is axially coupled to be rotatable with respect to the yaw frame 207. Here, the locking part 273 is formed to be spaced apart from and/or coupled to the first coupling part 271a of the locking body part 271. The locking part 273 may include a body part 273a formed in the shape of a bar to be rotatable around a locking rotation shaft 277 that is fixedly coupled to the yaw frame 207, a second coupling part 273b formed on one end portion of the body part 273a and engaged with the first coupling part 271a, and a contact part 273c brought into contact with the locking control part 275 to be explained later.

Here, the second coupling part 273*b* may be formed in the shape of a hook so as to be engaged with at least one of the gear of the first coupling part 271*a*.

Here, the second coupling part 273*b* may include a first surface 273*b*1 and a second surface 273*b*2. The first surface 273*b*1 may be formed to have a predetermined angle and a gentle inclination, and the second surface 273*b*2 may be formed vertically or almost vertically. Likewise, the first coupling part 271*a* of the locking body part 271 may include a first surface 271*a*l and a second surface 271*a*2. The first surface 271*a*l may be formed to have a predetermined angle and a gentle inclination, and the second surface 271*a*2 may be formed vertically or almost vertically. In this case, the inclined first surface 273*b*1 of the second coupling part 273*b* and the inclined first surface 271*a*l of the first coupling part 271*a* may be disposed to face each other (that is, to be in contact with each other).

The locking control part 275 is formed to be movable relative to the locking body part 271 and the locking part 273, to control whether the locking body part 271 and the locking part 273 are coupled to/spaced apart from each other depending its position.

The locking control part 275 may include a body part 275*a*, a guide part 275*b*, and a pressing part 275*c*. In detail, the body part 275*a* of the locking control part 275 may be formed in the shape of a bar to perform a reciprocating linear motion with respect to the locking body part 271. The guide part 275*b* may be formed on the body part 275*a* of the locking control part 275 to guide a movement path of the locking control part 265. The guide part 275*b* may be formed in the shape of an elongated hole, and one or more guide pins 276 fixedly coupled to the yaw frame 207 may be inserted into the guide part 275*b*. Accordingly, the locking control part 275 may perform a reciprocating linear motion with respect to the locking body part 271 by virtue of the guide part 275*b* and the guide pins 276. Here, the drawings illustrate that the guide part 275*b* is formed in the shape of a hole and the guide pin 276 is formed in the shape of a pin, but the concept of the present disclosure is not limited thereto. The guide part may alternatively be formed in various shapes to guide the linear motion of the locking control part 275, for example, a protrusion may be formed on the locking control part 275 and a guide groove may be formed in the locking body part 271 or the yaw frame 207.

The pressing part 275*c* may protrude to a certain extent from both surfaces of the locking control part 275 to be in contact with the contact part 273*c* of the locking part 273. Here, the pressing part 275*c* is formed to gradually protrude toward the distal end 205 of the manipulation part 200, and thus may be formed in a substantially arrow shape.

In the drawings, the pressing part 275*c* is formed in the shape of a hole, and the contact part 273*c* of the locking part 273 is inserted into the hole-shaped pressing part 275*c*, so that the contact part 273*c* is pressed by an inner edge surface of the pressing part 275*c*. However, the concept of the present disclosure is not limited thereto. Alternatively, as illustrated in FIGS. 27 and 28, the pressing part (see 565*c* in FIG. 27) may protrude as a whole from the body part (see 565*a* in FIG. 27), and the contact part (see 563*c* in FIG. 27) may be pressed by an outer peripheral surface of the pressing part (565*c* in FIG. 27).

Regardless of the shape, the pressing part 275*c* may be formed to be inclined by a certain degree with respect to the guide pin 276 or the guide part 275*b*, which is a central axis of movement. In other words, it may also be expressed that a width becomes thicker in one direction along the guide pin 276. Accordingly, when the locking control part 275 moves in any one direction, the pressing part 275*c* of the locking control part 275 may press the contact part 273*c* of the locking part 273, such that the locking part 273 is spaced apart from the locking body part 271.

Here, since the locking control part 275 is coupled to a second locking wire 292, which will be described later, the locking control part 275 may be moved in any one direction as the second locking wire 292 is moved by rotation of a first locking lever part 281.

Meanwhile, an elastic member 278 may be further disposed between the locking part 273 and the locking control part 275. For example, the elastic member 278 may be formed in the form of a coil spring. One side of the elastic member 268 may be coupled to the locking control part 275 side and the other side may be fixedly coupled to the yaw frame 207 side. In this instance, the elastic member 278 may be configured as a tension spring, and may apply a predetermined elastic force so that the locking control part 275 moves in one direction.

Since the operation of the locking member 270 is almost similar to the operation of the locking member 260, the specific operation of the locking member 270 will be omitted.

Hereinafter, the locking manipulation part 280 will be described in more detail.

The locking manipulation part 280 may include a first locking lever part 281, a second locking lever part 282, a first locking wire 291, and a second locking wire 292. Additionally, the locking manipulation part 280 may further include a locking wire holder 295.

In the present disclosure, the relative rotational motion among the pitch manipulation part 201, the yaw manipulation part 202, and the bent part 402 is controlled by the movement of the first locking wire 291 and the second locking wire 292 by the manipulation of the locking manipulation part 280, but the concept of the present disclosure is not limited thereto, and various modified examples of controlling a relative linear motion in a sliding manner or a button-pushing manner may also be made.

In present disclosure, a locking wire refers to the first locking wire 291 and the second locking wire 292.

First, the lock manipulation part 280 may be at least partially accommodated in the first handle 204, and may play a role of controlling the locking and unlocking operations of the locking devices 260 and 270. Here, the first handle 204 may have a hollow portion formed therein to provide a movement path for the first locking wire 291, the second locking wire 292, etc.

A first end portion of the first locking lever part 281 is rotatably coupled to an end portion of the first handle 204. That is, the first locking lever part 281 is formed to be rotatable with respect to the first handle 204 around a rotation shaft L1. Here, an elastic member 285 may be fitted onto the rotation shaft L1 of the first locking lever part 281, to apply a predetermined elastic force, such that the first locking lever part 281 rotates relative to the first handle 204 in a clockwise direction when viewed in FIG. 21.

Meanwhile, a locking wire holder 295 may be formed within the first locking lever part 281 to be rotatable around the rotation shaft L1 together with the first locking lever part 281. Also, the first locking wire 291 and the second locking wire 292 may be fixedly coupled to the locking wire holder 295. Therefore, when the first locking lever part 281 rotates with respect to the first handle 204 around the rotation shaft L1, the locking wire holder 295 may also rotate together with the first locking lever part 281, so as to pull or release the first locking wire 291 and the second locking wire 292.

Meanwhile, the second locking lever part 282 is rotatably coupled to a second end portion of the first locking lever part 281. Here, the second locking lever part 282 may be detachably coupled to the first handle 204.

To this end, the second locking lever part 282 may be formed in a shape similar to 'L' bent approximately by 90°, and a hook part 284 may be formed on one end portion, to which the first handle 204 is coupled, of both end portions of the second locking lever part 282. In addition, a stop recess 204a in which the hook part 284 is seated may be formed in the first handle 204, and a stopping part 204b on which the hook part 284 is caught may protrude from one side of the stop recess 204a.

Here, an elastic member (not illustrated) may be fitted onto a rotation shaft L2 of the second locking lever part 282, to apply a predetermined elastic force, such that the second locking lever part 282 rotates relative to the first locking lever part 281 in the clockwise direction when viewed in FIG. 21.

The first locking wire 291 may be formed so that one end portion thereof is coupled with the locking member 260 and the other end portion is coupled with the locking wire holder 295. The second locking wire 292 may be formed so that one end portion thereof is coupled with the locking member 270 and the other end portion is coupled with the locking wire holder 295.

Hereinafter, the operation of the locking manipulation part 280 will be described in more detail.

FIG. 22 is a diagram illustrating the unlocked state.

In the unlocked state, the hook part 284 of the second locking lever part 282 is coupled to the stopping part 204b of the first handle 204, thereby enabling the second locking lever part 282 and the first locking lever part 281 connected thereto to be coupled in close contact with the first handle 204.

In this state, because the elastic member (not illustrated) disposed on the rotation shaft L2 of the second locking lever part 282 applies a predetermined elastic force to rotate the second locking lever part 282 in the clockwise direction when viewed in FIG. 21, the hook part 284 of the second locking lever part 282 is maintained in the coupled state with the stopping part 204b of the first handle 204.

In this situation where the first locking lever part 281 is coupled to the first handle 204, the user may rotate the first locking lever part 281 around the rotation shaft L1 of the first locking lever part 281 to be separated from the first handle 204. In this instance, the user may simply push a predetermined bent part of the second locking lever part 282 by using a finger, to release the second locking lever part 282 from the first handle 204 and to make the first locking lever part 281 spaced apart from the first handle 204.

Specifically, the hook part 71 of the second locking lever part 282 may be released from the stopping part 52 by rotating the second locking lever part 282 relative to the first locking lever part 281. Accordingly, the first locking lever part 281 may be detached from the first handle 204 by an elastic restoring force of a lever spring 65, which is connected to the first locking lever part 281, so as to be spaced apart from the first handle 204.

Mode of Disclosure

Second Embodiment

FIG. 27 is a plan view illustrating a locked state of a locking device according to another embodiment of the present disclosure, and FIG. 28 is a plan view illustrating an unlocked state of the locking device according to another embodiment of the present disclosure.

Referring to FIGS. 12, 27, and 28, a locking device 560 may include a locking body part 561, a locking part 563, and a locking control part 565. The locking device 560 serves to lock or unlock the pitch motion of the pitch manipulation part 202.

First, although not illustrated in detail in the drawings, the locking body part 561 may be fixedly coupled to the bent part 402 of the connection part 400. Accordingly, the locking body part 561 may be rotatable together with the bent part 402 of the connection part 400.

One end portion of the bent part 402 and the locking body part 561 are axially coupled to a yaw frame 507 by a rotation shaft 546. Thus, the yaw frame 507 is rotatable relative to the bent part 402 (and the locking body part 561).

Meanwhile, the locking part 563 may be coupled to the yaw frame 507.

In other words, the locking body part 561 is fixedly coupled to the bent part 402 of the connection part 400, and the locking part 563 is coupled to the yaw frame 507. Accordingly, when the locking part 563 is coupled to the locking body part 561, the yaw frame 507 is in a locked state not to be rotatable relative to the bent part 402 and the locking body part 561. On the other hand, when the locking part 563 is spaced apart from the locking body part 561, the yaw frame 507 is unlocked to be rotatable relative to the bent part 402 and the locking body part 561. This will be explained in more detail as follows.

In detail, the locking body part 561 is fixedly coupled to the bent part 402 of the connection part 400. Here, the locking body part 561 may be formed substantially in the form of a disk, and have a plurality of first coupling parts 561a formed in a gear shape on an outer circumferential surface thereof. Therefore, the locking body part 261 may be formed as a whole in a gear shape. The locking body part 561 is fixedly coupled to one end portion of the bent part 402 of the connection part 400. Accordingly, when the rotation of the locking body part 561 is restricted by the locking part 563 and the locking control part 565, the rotation of the connection part 400 fixedly coupled to the locking body part 561 is restricted, thereby locking the pitch motion.

The locking part 563 is coupled to the yaw frame 507. In detail, the locking part 563 is axially coupled to be rotatable with respect to the yaw frame 507. Here, the locking part 563 is formed to be spaced apart from and/or coupled to the first coupling part 561a of the locking body part 561. The locking part 563 may include a body part 563a formed in the shape of a bar to be rotatable around a locking rotation shaft 567 that is fixedly coupled to the yaw frame 507, a second coupling part 563b formed on one end portion of the body part 563a and engaged with the first coupling part 561a, and a contact part 563c brought into contact with the locking control part 565 to be explained later.

Here, the second coupling part 563b may be formed in the shape of a hook so as to be engaged with at least one of the gear of the first coupling part 561a.

Here, the second coupling part 563b may include a first surface 563b1 and a second surface 563b2. The first surface 563b1 may be formed to have a predetermined angle and a gentle inclination, and the second surface 563b2 may be formed vertically or almost vertically. Likewise, the first coupling part 561a of the locking body part 561 may include a first surface 561a1 and a second surface 561a2. The first surface 561a1 may be formed to have a predetermined angle and a gentle inclination, and the second surface 561a2 may be formed vertically or almost vertically. In this case, the inclined first surface 563*b*1 of the second coupling part 563*b* and the inclined first surface 561*a*1 of the first coupling part 561*a* may be disposed to face each other (that is, to be in contact with each other).

The locking control part 565 is formed to be movable relative to the locking body part 561 and the locking part 563, to control whether the locking body part 561 and the locking part 563 are coupled to/spaced apart from each other depending its position.

The locking control part 565 may include a body part 565*a*, a guide part 565*b*, and a pressing part 565*c*. In detail, the body part 565*a* of the locking control part 565 may be formed in the shape of a bar to perform a reciprocating linear motion with respect to the locking body part 561. The guide part 565*b* may be formed on the body part 565*a* of the locking control part 565 to guide a movement path of the locking control part 565. The guide part 565*b* may be formed in the shape of an elongated hole, and one or more guide pins 566 fixedly coupled to the yaw frame 507 may be inserted into the guide part 565*b*. Accordingly, the locking control part 565 may perform a reciprocating linear motion with respect to the locking body part 561 by virtue of the guide part 565*b* and the guide pins 566. Here, the drawings illustrate that the guide part 565*b* is formed in the shape of a hole and the guide pin 566 is formed in the shape of a pin, but the concept of the present disclosure is not limited thereto. The guide part may alternatively be formed in various shapes to guide the linear motion of the locking control part 565, for example, a protrusion may be formed on the locking control part 565 and a guide groove may be formed in the locking body part 561 or the yaw frame 507.

The pressing part 565*c* may protrude to a certain extent from both surfaces of the locking control part 565 to be in contact with the contact part 563*c* of the locking part 563. Here, the pressing part 565*c* is formed to gradually protrude toward the distal end 505 of the manipulation part 500, and thus may be formed substantially in an arrow shape. Here, the pressing part 565*c* may protrude from the body part 565*a* as a whole, and the contact part 563*c* may be pressed by an outer peripheral surface of the pressing part 565*c*.

Regardless of the shape, the pressing part 565*c* may be formed to be inclined by a certain degree with respect to the guide pin 566 or the guide part 565*b*, which is a central axis of movement. In other words, it may also be expressed that a width becomes thicker in one direction along the guide pin 566. Accordingly, when the locking control part 565 moves in any one direction, the pressing part 565*c* of the locking control part 565 may press the contact part 563*c* of the locking part 563, such that the locking part 563 is spaced apart from the locking body part 561.

Meanwhile, a first elastic member 568 may be further disposed on the locking control part 565. The elastic member 568 may apply a predetermined elastic force so that the locking control part 565 moves in a direction opposite to an arrow A3 of FIG. 18. Here, the first elastic member 568 may be configured as a compression spring.

Meanwhile, a second elastic member 569 may be further disposed on the locking part 563. The elastic member 569 may apply a predetermined elastic force so that a pair of locking parts 563 rotate in a direction of being close toward each other (i.e., a direction opposite to an arrow A4). (For example, when viewed in FIG. 27, the elastic force may be applied such that the locking part 563 on the left rotates clockwise, while the locking part 563 on the right rotate counterclockwise.)

Therefore, without the intervention of the locking control part 565, it may be explained that the locking part 563 is basically receiving force in a direction that it approaches the first coupling part 561*a* of the locking body part 561. In other words, it may be seen that the locking part 563 is basically receiving force from the second elastic member 569 to be in the locked state.

Here, the second elastic member 569 may be configured as a compression spring, and may apply a predetermined elastic force so that the locking part 563 rotates in a predetermined direction. Or, the second elastic member 569 may be configured as a torsion spring.

Therefore, if there is no intervention by another member, the locking control part 565 is basically positioned, as illustrated in FIG. 27, by the elastic force applied by the first elastic member 568 and the second elastic member 569. This state is a state in which the locking control part 565 applies the minimum force to the locking part 563. In this state, the locking body part 561 and the locking part 563 are coupled to each other, thus to be in a locked state. In other words, it may be seen that the locking part 563 is basically receiving force from the first elastic member 568 and the second elastic member 569 to be in the locked state.

In this state, when the locking control part 565 moves in a direction of an arrow A3 due to an external force, the locking control part 565 rotates the locking part 563 in a direction of an arrow A4 during its movement, and thus the locking part 563 is spaced apart from the locking body part 561, so as to be unlocked.

As such, the present disclosure has been described with reference to an embodiment shown in the drawings, but it will be understood that this is merely exemplary, and those of ordinary skill in the art will understand that various modifications and variations of the embodiments are possible therefrom. Accordingly, the true technical protection scope of the present disclosure should be defined by the technical spirit of the appended claims.

INDUSTRIAL APPLICABILITY

The present disclosure relates to a surgical instrument, and more particularly, may be used to a surgical instrument that is operable manually or automatically to be used in laparoscopic surgery or other various surgeries, wherein the surgical instrument includes a locking device that may lock and/or unlock at least one motion.

The invention claimed is:

1. A surgical instrument comprising: an end tool having one or more jaws and rotatable in two or more directions;
 a manipulation part to control rotation of the end tool in the two or more directions;
 a power transmission part including one or more jaw wires connected to the manipulation part to transmit rotation of the manipulation part to the jaws; and
 a connection part extending in a first direction (X-axis), and having one end portion coupled to the end tool and another end coupled to the manipulation part, such that the manipulation part and the end tool are connected to each other,
 wherein the manipulation part comprises:
 a pitch manipulation part to control a pitch motion of the end tool; and
 a locking member formed to be coupled to the pitch manipulation part, to lock or unlock a pitch motion of the pitch manipulation part according to whether the locking member is coupled to the pitch manipulation part, wherein the locking member comprises:
a locking body part fixedly coupled to the pitch manipulation part, and a locking part formed to be coupled to the locking body part; and
a locking control part to control a position of the locking part so that the locking part is located at any one of a first position or a second position,
wherein the locking control part is configured to perform a linear reciprocating motion with respect to the locking body part, and
wherein in the one direction that the locking control part moves, a width of the locking control part increases along the one direction.

2. The surgical instrument of claim 1, wherein
the locking part is coupled to the locking body part when the locking part is located at the first position, to restrict movement of the locking body part, and
the locking part is spaced apart from the locking body part when the locking part is located at the second position, to allow rotation of the locking body part.

3. The surgical instrument of claim 2, wherein
the locking control part presses the locking part while moving in one direction, such that the locking part moves in a direction of being spaced apart from the locking body part.

4. The surgical instrument of claim 3, wherein
while the locking control part moves in the one direction, the locking control part presses the locking part in such a direction that the locking part is away from the locking body part.

5. The surgical instrument of claim 2, wherein
a first elastic member is interposed between the locking control part and the locking body part to apply a predetermined elastic force to the locking control part so that the locking part is located at any one of the first position or the second position.

6. The surgical instrument of claim 1, wherein
the pitch manipulation part is axially coupled to the connection part, and the locking member controls whether the pitch manipulation part rotates with respect to the connection part.

7. A surgical instrument comprising: an end tool having one or more jaws and rotatable in two or more directions;
a manipulation part to control rotation of the end tool in the two or more directions;
a power transmission part including one or more jaw wires connected to the manipulation part to transmit rotation of the manipulation part to the jaws; and
a connection part extending in a first direction (X-axis), and having one end portion coupled to the end tool and another end coupled to the manipulation part, such that the manipulation part and the end tool are connected to each other,
wherein the manipulation part comprises:
a yaw manipulation part to control a yaw motion of the end tool; and
a locking member formed to be coupled to the yaw manipulation part, to lock or unlock a yaw motion of the yaw manipulation part according to whether the locking member is coupled to the yaw manipulation part,
wherein the locking member comprises:
a locking body part fixedly coupled to the yaw manipulation part, and a locking part formed to be coupled to the locking body part; and
a locking control part to control a position of the locking part so that the locking part is located at any one of a first position or a second position,
wherein the locking control part is configured to perform a linear reciprocating motion with respect to the locking body part, and
wherein in the one direction that the locking control part moves, a width of the locking control part increases along the one direction.

8. The surgical instrument of claim 7, wherein
the locking part is coupled to the locking body part when the locking part is located at the first position, to restrict movement of the locking body part, and
the locking part is spaced apart from the locking body part when the locking part is located at the second position, to allow rotation of the locking body part.

9. The surgical instrument of claim 8, wherein
the locking control part presses the locking part while moving in one direction, such that the locking part moves in such a direction that the locking part is spaced apart from the locking body part.

10. The surgical instrument of claim 9, wherein
while the locking control part moves in the one direction, the locking control part presses the locking part in such a direction that the locking part is away from the locking body part.

11. The surgical instrument of claim 8, wherein
a first elastic member is interposed between the locking control part and the locking body part to apply a predetermined elastic force to the locking control part so that the locking part is located at any one of the first position or the second position.

12. The surgical instrument of claim 7, wherein
the locking body part is formed in a gear shape including a plurality of first coupling parts, and
the locking part is formed in a hook shape to be coupled to one of the plurality of first coupling parts.

13. The surgical instrument of claim 7, wherein
the manipulation part further comprises a pitch manipulation part to control a pitch motion of the end tool,
the yaw manipulation part is axially coupled to the pitch manipulation part, and the locking member controls whether the yaw manipulation part rotates with respect to the pitch manipulation part.

14. A surgical instrument comprising: an end tool having one or more jaws and rotatable in two or more directions;
a manipulation part to control rotation of the end tool in the two or more directions;
a power transmission part including one or more jaw wires connected to the manipulation part to transmit rotation of the manipulation part to the jaws; and
a connection part extending in a first direction (X-axis), and having one end portion coupled to the end tool and another end coupled to the manipulation part, such that the manipulation part and the end tool are connected to each other,
wherein the manipulation part comprises:
a pitch manipulation part to control a pitch motion of the end tool; and
a locking member formed to be coupled to the pitch manipulation part, to lock or unlock a pitch motion of the pitch manipulation part according to whether the locking member is coupled to the pitch manipulation part, wherein the locking member comprises a locking body part fixedly coupled to the pitch manipulation part, and a locking part formed to be coupled to the locking body part, wherein the locking body part comprises a first coupling part formed in a gear shape, and the locking part comprises a second coupling part formed in a hook shape, the second coupling part configured to be coupled to the first coupling part.

* * * * *